(12) United States Patent
Osborne et al.

(10) Patent No.: US 11,801,360 B2
(45) Date of Patent: Oct. 31, 2023

(54) CONNECTIONS FOR HUMIDIFICATION SYSTEM

(71) Applicant: Fisher & Paykel Healthcare Limited, Auckland (NZ)

(72) Inventors: Hamish Adrian Osborne, Auckland (NZ); Gavin Walsh Millar, Auckland (NZ); Stephen David Evans, Auckland (NZ); Bruce Gordon Holyoake, Auckland (NZ); James William Stanton, Auckland (NZ); David Leon McCauley, Auckland (NZ); Gareth Thomas McDermott, Auckland (NZ); Nicholas James Michael McKenna, Auckland (NZ); Myfanwy Jane Antica Norton, Auckland (NZ); Adrian John Elsworth, Auckland (NZ); Michael John Andresen, Auckland (NZ); Jonathan Andrew George Lambert, Auckland (NZ); Sandeep Singh Gurm, Auckland (NZ); Tessa Hazel Paris, Auckland (NZ); Joseph Nathaniel Griffiths, Auckland (NZ); Ping Si, Auckland (NZ); Christopher Gareth Sims, Auckland (NZ); Elmo Benson Stoks, Auckland (NZ); Dexter Chi Lun Cheung, Auckland (NZ); Peter Alan Seekup, Auckland (NZ); Po-Yen Liu, Auckland (NZ); Richard Edward Lang, Auckland (NZ); Paul James Tonkin, Auckland (NZ); Ian Lee Wai Kwan, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 906 days.

(21) Appl. No.: 16/271,027

(22) Filed: Feb. 8, 2019

(65) Prior Publication Data

US 2019/0255278 A1    Aug. 22, 2019

Related U.S. Application Data

(63) Continuation of application No. 15/021,673, filed as application No. PCT/NZ2014/000201 on Sep. 15, 2014, now Pat. No. 10,245,407.

(Continued)

(51) Int. Cl.
*A61M 16/16*    (2006.01)
*A61M 16/08*    (2006.01)
(Continued)

(52) U.S. Cl.
CPC .......... *A61M 16/16* (2013.01); *A61M 16/024* (2017.08); *A61M 16/0816* (2013.01);
(Continued)

(58) Field of Classification Search
CPC ...... A61M 16/16–168; A61M 39/1011; A61M 39/10; A61M 2039/1005; F16L 25/01; H01R 13/005; H01R 13/6658; A47L 9/246
(Continued)

(56) References Cited

U.S. PATENT DOCUMENTS

| 1,085,833 A | 2/1914 | Wilson |
| 1,154,259 A | 9/1915 | Light |

(Continued)

FOREIGN PATENT DOCUMENTS

| AU | 667538 | 3/1996 |
| AU | 726022 | 10/2000 |

(Continued)

OTHER PUBLICATIONS

Chinese Examination Report for Application No. 201580038988.3 dated Aug. 30, 2018.
(Continued)

*Primary Examiner* — Justine R Yu
*Assistant Examiner* — Alexander Morales
(74) *Attorney, Agent, or Firm* — Knobbe Martens Olson & Bear, LLP

(57) ABSTRACT

A humidification system can include a heater base, a humidification chamber, and a breathing circuit. A cartridge can be
(Continued)

removably coupled to the heater base. The cartridge can include various sensors, probes, sensor wire connectors, heater wire connectors, and/or other features. The cartridge can include features configured to mate with corresponding features on the humidification chamber and the heater base. The cartridge includes a memory, such as an EEPROM, or other suitable storage device. When the cartridge is installed on the heater base, the memory is electrically connected to a processor and/or memory of the heater base. Various models of cartridges can be produced for use with different humidification chambers, breathing circuits, and/or therapies. A connector can be configured to couple an inspiratory conduit to an outlet port of the humidification chamber. The connector can provide a pneumatic connection to the outlet port and an electrical connection to the cartridge.

44 Claims, 45 Drawing Sheets

Related U.S. Application Data

(60) Provisional application No. 62/032,462, filed on Aug. 1, 2014, provisional application No. 62/024,969, filed on Jul. 15, 2014, provisional application No. 61/919,485, filed on Dec. 20, 2013, provisional application No. 61/877,566, filed on Sep. 13, 2013, provisional application No. 61/877,784, filed on Sep. 13, 2013, provisional application No. 61/877,736, filed on Sep. 13, 2013, provisional application No. 61/877,622, filed on Sep. 13, 2013.

(51) Int. Cl.
*A61M 16/10* (2006.01)
*A61M 16/00* (2006.01)

(52) U.S. Cl.
CPC ...... *A61M 16/0875* (2013.01); *A61M 16/109* (2014.02); *A61M 16/1095* (2014.02); *A61M 16/0833* (2014.02); *A61M 16/108* (2014.02); *A61M 16/1085* (2014.02); *A61M 16/161* (2014.02); *A61M 2016/0027* (2013.01); *A61M 2016/0039* (2013.01); *A61M 2016/1025* (2013.01); *A61M 2205/3368* (2013.01); *A61M 2205/3389* (2013.01); *A61M 2205/505* (2013.01); *A61M 2205/52* (2013.01); *A61M 2205/6018* (2013.01); *A61M 2205/6027* (2013.01); *A61M 2205/6045* (2013.01); *A61M 2205/70* (2013.01); *A61M 2209/086* (2013.01)

(58) Field of Classification Search
USPC ............. 128/206.24, 206.16, 201.17, 200.18
See application file for complete search history.

(56) References Cited

U.S. PATENT DOCUMENTS

| | | | |
|---|---|---|---|
| 2,073,335 A | 3/1937 | Connell | |
| 2,510,125 A | 6/1950 | Meakin | |
| 2,516,864 A | 8/1950 | Gilmore et al. | |
| 2,745,074 A | 1/1951 | Darling | |
| 2,590,797 A | 3/1952 | Siciliano | |
| 2,621,875 A | 12/1952 | Darling | |
| 2,634,311 A | 4/1953 | Darling | |
| 3,117,596 A | 1/1964 | Kahn | |
| 3,163,707 A | 12/1964 | Darling | |
| 3,283,580 A | 11/1966 | Jacob et al. | |
| 3,394,954 A | 7/1968 | Sarns | |
| 3,404,684 A | 10/1968 | Brewer et al. | |
| 3,485,237 A | 12/1969 | Bedford | |
| 3,495,628 A | 2/1970 | Boender | |
| 3,582,094 A | 6/1971 | Whittaker | |
| 3,588,859 A | 6/1971 | Petree | |
| 3,623,511 A | 11/1971 | Levin | |
| 3,638,926 A | 2/1972 | Melville et al. | |
| 3,659,604 A | 5/1972 | Melville et al. | |
| 3,703,892 A | 11/1972 | Meyers | |
| 3,777,298 A | 12/1973 | Newman | |
| 3,806,102 A | 4/1974 | Valenta et al. | |
| 3,903,742 A | 9/1975 | Colton | |
| 3,945,378 A | 3/1976 | Paluch | |
| 3,954,920 A | 5/1976 | Heath | |
| 3,987,133 A | 10/1976 | Andra | |
| 3,990,727 A | 11/1976 | Gallagher | |
| 4,010,748 A | 3/1977 | Dobritz | |
| 4,028,444 A | 6/1977 | Brown | |
| 4,038,519 A | 7/1977 | Foucras | |
| 4,060,576 A | 11/1977 | Grant | |
| 4,098,853 A | 7/1978 | Brown et al. | |
| 4,111,197 A | 9/1978 | Warncke et al. | |
| 4,139,762 A | 2/1979 | Pohrer et al. | |
| 4,152,379 A | 5/1979 | Suhr | |
| 4,160,466 A | 7/1979 | Jousson | |
| 4,172,709 A | 10/1979 | Kippel et al. | |
| 4,183,248 A | 1/1980 | West | |
| 4,192,836 A | 3/1980 | Bartscher | |
| 4,301,200 A | 11/1981 | Langenfeld et al. | |
| 4,333,451 A | 6/1982 | Paluch | |
| 4,417,574 A | 11/1983 | Taloon et al. | |
| 4,428,403 A | 1/1984 | Lee | |
| 4,463,593 A | 8/1984 | Parker | |
| 4,473,923 A | 10/1984 | Neroni et al. | |
| 4,529,867 A | 7/1985 | Velnosky et al. | |
| 4,531,551 A | 7/1985 | Eichelberger et al. | |
| 4,533,115 A * | 8/1985 | Lissau ................... | B60T 17/043 137/381 |
| 4,545,290 A | 10/1985 | Lieberman | |
| 4,558,708 A | 12/1985 | Labuda et al. | |
| 4,564,748 A | 1/1986 | Gupton | |
| 4,588,425 A | 5/1986 | Usry et al. | |
| 4,599,895 A | 7/1986 | Wiseman | |
| 4,621,632 A | 11/1986 | Bartels et al. | |
| 4,676,237 A | 6/1987 | Wood et al. | |
| 4,686,354 A | 8/1987 | Makin | |
| 4,708,831 A | 11/1987 | Elsworth et al. | |
| 4,714,078 A | 12/1987 | Paluch | |
| 4,753,758 A | 6/1988 | Miller | |
| 4,774,032 A | 9/1988 | Coates et al. | |
| 4,809,698 A | 3/1989 | Kogo | |
| 4,813,280 A | 3/1989 | Miller, Jr. et al. | |
| 4,830,515 A | 5/1989 | Cortes | |
| 4,844,512 A | 7/1989 | Gahwiler | |
| 4,942,877 A | 7/1990 | Sakai et al. | |
| 4,944,310 A | 7/1990 | Sullivan | |
| 4,967,744 A | 11/1990 | Chua | |
| 5,017,875 A | 5/1991 | Hori | |
| 5,027,811 A | 7/1991 | Tuxill | |
| 5,031,612 A | 7/1991 | Clementi | |
| 5,038,773 A | 8/1991 | Norlien | |
| 5,054,819 A | 10/1991 | Grunwald | |
| 5,058,588 A | 10/1991 | Kaestle | |
| 5,060,506 A | 10/1991 | Douglas | |
| 5,062,145 A | 10/1991 | Zwaan | |
| 5,109,471 A | 4/1992 | Lang | |
| 5,117,819 A | 6/1992 | Servidio et al. | |
| 5,127,442 A | 7/1992 | Blomqvist | |
| 5,134,996 A | 8/1992 | Bell | |
| 5,143,060 A | 9/1992 | Smith | |
| 5,148,801 A | 9/1992 | Douwens et al. | |
| 5,181,858 A * | 1/1993 | Matz ................... | H01R 13/6658 439/188 |
| 5,209,225 A | 5/1993 | Glenn | |
| 5,213,138 A | 5/1993 | Presz, Jr. | |
| 5,213,376 A | 5/1993 | Szabo | |
| 5,233,996 A | 8/1993 | Coleman et al. | |
| 5,303,701 A | 4/1994 | Heins et al. | |
| RE34,599 E | 5/1994 | Suszynski et al. | |
| 5,342,126 A | 8/1994 | Heston | |

(56) References Cited

U.S. PATENT DOCUMENTS

| | | | |
|---|---|---|---|
| 5,357,948 | A | 10/1994 | Eilentropp |
| 5,367,604 | A | 11/1994 | Murray |
| 5,392,770 | A | 2/1995 | Clawson et al. |
| 5,396,884 | A | 3/1995 | Bagwell et al. |
| 5,454,061 | A | 9/1995 | Carlson |
| 5,454,479 | A | 10/1995 | Kraus |
| 5,483,616 | A | 1/1996 | Chiu et al. |
| 5,484,223 | A | 1/1996 | Saito |
| 5,488,447 | A | 1/1996 | Patton et al. |
| 5,495,872 | A | 3/1996 | Gallagher et al. |
| 5,499,737 | A | 3/1996 | Kraus |
| RE35,225 | E | 4/1996 | Herweck et al. |
| 5,529,093 | A | 6/1996 | Gallagher et al. |
| 5,537,996 | A | 7/1996 | McPhee |
| 5,540,219 | A | 7/1996 | Mechlenburg et al. |
| 5,548,879 | A | 8/1996 | Wu |
| 5,551,883 | A | 9/1996 | Davis |
| 5,558,084 | A | 9/1996 | Daniell |
| 5,564,415 | A | 10/1996 | Dobson et al. |
| 5,598,837 | A | 2/1997 | Sirianne et al. |
| 5,600,752 | A | 2/1997 | Lopatinsky |
| 5,630,806 | A | 5/1997 | Inagaki et al. |
| 5,637,006 | A | 6/1997 | Almeras |
| 5,640,951 | A | 6/1997 | Huddart et al. |
| 5,660,567 | A | 8/1997 | Nierlich et al. |
| 5,667,306 | A | 9/1997 | Montreuil |
| 5,720,293 | A | 2/1998 | Nierlich et al. |
| 5,778,872 | A | 7/1998 | Fukunaga et al. |
| 5,829,880 | A | 11/1998 | Diedrich |
| 5,881,393 | A | 3/1999 | Marchello |
| 5,906,201 | A | 5/1999 | Nilson |
| 5,913,249 | A | 6/1999 | Weckstrom |
| 5,943,473 | A | 8/1999 | Levine |
| 5,975,591 | A * | 11/1999 | Guest .................. F16L 37/0925 285/319 |
| 5,979,247 | A | 11/1999 | Kizawa |
| D419,522 | S | 1/2000 | Kamagai |
| 6,024,694 | A | 2/2000 | Goldberg |
| 6,030,244 | A * | 2/2000 | Buckheit .................. F16L 37/18 439/291 |
| 6,039,696 | A | 3/2000 | Bell |
| 6,050,260 | A | 4/2000 | Daniell |
| 6,053,482 | A | 4/2000 | Glenn et al. |
| 6,058,977 | A | 5/2000 | Hotta |
| 6,078,729 | A | 6/2000 | Kopel |
| 6,078,730 | A | 6/2000 | Huddart et al. |
| 6,095,505 | A | 8/2000 | Miller |
| 6,102,037 | A | 8/2000 | Koch |
| 6,105,970 | A | 8/2000 | Siegrist et al. |
| 6,126,610 | A | 10/2000 | Rich et al. |
| 6,128,963 | A | 10/2000 | Bromster |
| 6,138,674 | A | 10/2000 | Gull et al. |
| 6,190,480 | B1 | 2/2001 | Carlson |
| 6,196,980 | B1 | 3/2001 | Akerfeldt et al. |
| 6,201,983 | B1 | 3/2001 | Haumann et al. |
| 6,208,514 | B1 | 3/2001 | Stark |
| 6,226,451 | B1 | 5/2001 | Wong |
| 6,272,933 | B1 | 8/2001 | Gradon et al. |
| 6,332,462 | B1 | 12/2001 | Krohn |
| 6,347,646 | B2 | 2/2002 | Fikui |
| 6,349,722 | B1 | 2/2002 | Gradon et al. |
| 6,349,724 | B1 | 2/2002 | Burton et al. |
| 6,360,741 | B2 | 3/2002 | Truschel |
| 6,367,974 | B1 | 4/2002 | Lin |
| 6,374,864 | B1 | 4/2002 | Philip |
| 6,394,145 | B1 | 5/2002 | Gessil |
| 6,397,841 | B1 | 6/2002 | Kenyon et al. |
| 6,402,207 | B1 | 6/2002 | Segal et al. |
| 6,435,180 | B1 | 8/2002 | Hewson et al. |
| 6,467,477 | B1 | 10/2002 | Frank et al. |
| 6,508,249 | B2 | 1/2003 | Hoenig |
| 6,511,075 | B1 | 1/2003 | Schmidt |
| 6,540,734 | B1 | 4/2003 | Chiu |
| 6,551,143 | B2 | 4/2003 | Tanaka et al. |
| 6,554,260 | B1 | 4/2003 | Lipscombe et al. |
| 6,591,061 | B2 | 7/2003 | Wang |
| 6,598,604 | B1 | 7/2003 | Seakins |
| 6,600,727 | B1 * | 7/2003 | Mackay .................. H04B 3/60 370/293 |
| 6,612,624 | B1 | 9/2003 | Segal et al. |
| 6,623,352 | B2 | 9/2003 | Illingworth |
| 6,631,718 | B1 | 10/2003 | Lovell |
| 6,648,669 | B1 | 11/2003 | Kim et al. |
| 6,655,207 | B1 | 12/2003 | Speldrich et al. |
| 6,655,975 | B1 * | 12/2003 | Liedtke .................. H05K 5/064 439/910 |
| 6,668,828 | B1 | 12/2003 | Figley et al. |
| 6,685,491 | B2 | 2/2004 | Gergek |
| 6,698,966 | B2 | 3/2004 | Hilton et al. |
| 6,824,180 | B2 | 11/2004 | Tomchak |
| 6,827,084 | B2 | 12/2004 | Grubb, Jr. |
| 6,874,771 | B2 | 4/2005 | Birdsell et al. |
| 6,895,803 | B2 | 5/2005 | Seakins et al. |
| 6,915,705 | B1 | 7/2005 | Truitt |
| 6,918,389 | B2 | 7/2005 | Seakins et al. |
| 6,935,337 | B2 | 8/2005 | Virr et al. |
| 6,943,566 | B2 | 9/2005 | Florin et al. |
| 6,953,354 | B2 | 10/2005 | Edirisuriya et al. |
| 7,043,979 | B2 | 5/2006 | Smith et al. |
| 7,063,668 | B2 | 6/2006 | Cardelius et al. |
| 7,086,422 | B2 | 8/2006 | Huber et al. |
| 7,090,541 | B1 | 8/2006 | Ho |
| 7,096,864 | B1 | 8/2006 | Mayer et al. |
| 7,120,354 | B2 | 10/2006 | Mackie et al. |
| 7,137,654 | B2 | 11/2006 | Segal et al. |
| 7,140,367 | B2 | 11/2006 | White et al. |
| 7,157,035 | B2 | 1/2007 | Edirisuriya et al. |
| 7,191,780 | B2 | 3/2007 | Faram |
| 7,225,809 | B1 | 6/2007 | Bowen et al. |
| 7,284,554 | B2 | 10/2007 | Shaw |
| 7,316,768 | B2 | 1/2008 | Aldridge et al. |
| 7,316,769 | B2 | 1/2008 | Aldridge |
| 7,327,547 | B1 | 2/2008 | Epstein |
| 7,327,949 | B1 | 2/2008 | Cheng et al. |
| 7,334,587 | B2 | 2/2008 | Lake |
| 7,364,436 | B2 | 4/2008 | Yen |
| 7,396,995 | B2 | 7/2008 | Laurent et al. |
| 7,448,383 | B2 | 11/2008 | Delache et al. |
| 7,469,586 | B2 | 12/2008 | Wild et al. |
| 7,478,635 | B2 | 1/2009 | Wixey et al. |
| 7,525,663 | B2 | 4/2009 | Kwok et al. |
| 7,551,450 | B2 * | 6/2009 | Sugawara ............ H05K 5/0278 361/752 |
| 7,607,360 | B2 | 10/2009 | Todokoro et al. |
| 7,614,398 | B2 | 11/2009 | Virr et al. |
| 7,637,288 | B2 | 12/2009 | Kressierer/Huber et al. |
| 7,677,246 | B2 | 3/2010 | Kepler et al. |
| 7,743,767 | B2 | 6/2010 | Ging et al. |
| 7,766,050 | B2 | 8/2010 | Patel |
| 7,794,426 | B2 | 9/2010 | Briones et al. |
| 7,814,907 | B2 | 10/2010 | Bremner et al. |
| 7,816,888 | B2 | 10/2010 | Rejman et al. |
| D628,288 | S | 11/2010 | Row et al. |
| 7,827,981 | B2 | 11/2010 | Barnford |
| 7,870,857 | B2 | 1/2011 | Dhuper et al. |
| 7,874,291 | B2 | 1/2011 | Ging et al. |
| 7,900,528 | B2 | 3/2011 | Vincent |
| 7,913,689 | B2 | 3/2011 | Henry et al. |
| 7,942,380 | B2 | 5/2011 | Bertinetti et al. |
| 7,942,389 | B2 | 5/2011 | Koch et al. |
| 7,965,930 | B2 | 6/2011 | Carlson et al. |
| 7,983,542 | B2 | 7/2011 | McGhin et al. |
| 7,987,847 | B2 | 8/2011 | Wickham |
| 7,992,554 | B2 | 8/2011 | Radomski et al. |
| 7,997,267 | B2 | 8/2011 | Ging et al. |
| 8,025,849 | B2 | 9/2011 | Baldwin et al. |
| 8,059,947 | B2 | 11/2011 | Bradley et al. |
| 8,063,343 | B2 | 11/2011 | McGhin et al. |
| 8,078,040 | B2 | 12/2011 | Forrester |
| 8,100,124 | B2 | 1/2012 | Becker et al. |
| 8,122,882 | B2 | 2/2012 | McGhin et al. |
| 8,136,521 | B2 | 3/2012 | Matthews et al. |
| 8,137,082 | B2 | 3/2012 | Campbell |
| 8,181,940 | B2 | 5/2012 | Payne et al. |

(56) References Cited

U.S. PATENT DOCUMENTS

| | | |
|---|---|---|
| 8,182,144 B2 | 5/2012 | Koch |
| 8,186,345 B2 | 5/2012 | Payton et al. |
| 8,186,352 B2 | 5/2012 | Gunaratnam et al. |
| 8,197,123 B2 | 6/2012 | Snyder et al. |
| 8,206,337 B2 | 6/2012 | Blackhurst et al. |
| 8,215,301 B2 | 7/2012 | Richards et al. |
| 8,221,530 B2 | 7/2012 | Peter et al. |
| 8,226,293 B2 | 7/2012 | Faries, Jr. |
| 8,240,306 B2 | 8/2012 | Cortez, Jr. et al. |
| 8,245,709 B2 | 8/2012 | Rossen et al. |
| 8,245,710 B2 | 8/2012 | Makinson et al. |
| 8,253,076 B2 | 8/2012 | Andel et al. |
| 8,257,286 B2 * | 9/2012 | Meyer .................. F16B 7/0413 601/148 |
| 8,267,084 B2 | 9/2012 | Kwok |
| 8,267,614 B2 | 9/2012 | Khoe |
| 8,282,427 B2 | 10/2012 | Yamazaki |
| 8,287,517 B2 | 10/2012 | Hanlon et al. |
| 8,316,848 B2 | 11/2012 | Kwok et al. |
| 8,333,194 B2 | 12/2012 | Lewis et al. |
| 8,333,195 B2 | 12/2012 | Cortez, Jr. et al. |
| 8,333,199 B2 | 12/2012 | Landis et al. |
| 8,355,753 B2 | 1/2013 | Bochenko et al. |
| 8,360,059 B2 | 1/2013 | Koulechov et al. |
| 8,365,726 B2 | 2/2013 | Snow et al. |
| 8,381,724 B2 | 2/2013 | Bowen et al. |
| 8,424,514 B2 | 4/2013 | Oates et al. |
| 8,453,641 B2 | 6/2013 | Payton et al. |
| 8,453,643 B2 | 6/2013 | Sanchez et al. |
| 8,459,261 B2 | 6/2013 | Ricciardelli |
| 8,469,025 B2 | 6/2013 | Mayer et al. |
| 8,490,621 B2 | 7/2013 | Radomski et al. |
| 8,496,001 B2 | 7/2013 | Schermeier at el. |
| RE44,453 E | 8/2013 | Virr et al. |
| 8,511,305 B2 | 8/2013 | Liu et al. |
| 8,511,651 B2 | 8/2013 | Fridberg et al. |
| 8,516,911 B2 | 8/2013 | Inoue |
| 8,522,782 B2 | 9/2013 | Lewis et al. |
| 8,528,552 B2 | 9/2013 | von Blumenthal |
| 8,544,465 B2 | 10/2013 | Smith et al. |
| 8,545,096 B2 | 10/2013 | Reiter |
| 8,550,072 B2 | 10/2013 | Thudor et al. |
| 8,631,789 B2 | 1/2014 | Virr et al. |
| 8,640,560 B2 | 2/2014 | Burke |
| 8,640,696 B2 | 2/2014 | Pujol et al. |
| 8,651,800 B2 | 2/2014 | Li |
| 8,733,348 B2 | 5/2014 | Korneff et al. |
| 8,733,349 B2 | 5/2014 | Bath et al. |
| 8,756,990 B2 | 6/2014 | Speldrich |
| 8,776,790 B2 | 7/2014 | Gentner et al. |
| 8,783,252 B2 | 7/2014 | Pierro et al. |
| 8,800,970 B2 | 8/2014 | Heine et al. |
| 8,770,190 B2 | 9/2014 | McCarthy |
| 8,844,388 B2 | 9/2014 | Burke |
| 8,844,521 B2 | 9/2014 | McCarthy |
| 8,851,071 B2 | 10/2014 | Kuo et al. |
| 8,905,023 B2 | 12/2014 | Niland et al. |
| 8,915,250 B2 | 12/2014 | Dugan et al. |
| 8,931,481 B2 | 1/2015 | Jones et al. |
| 8,939,147 B2 | 1/2015 | Henry et al. |
| 8,960,727 B2 * | 2/2015 | Kendrick ........... A61M 39/1011 285/93 |
| 8,985,105 B2 | 3/2015 | Burton et al. |
| 8,997,740 B2 | 4/2015 | Pujol et al. |
| 9,022,946 B2 | 5/2015 | Haque |
| 9,039,277 B2 | 5/2015 | Le Bouquin et al. |
| 9,067,036 B2 | 6/2015 | Korneff et al. |
| 9,095,668 B2 | 8/2015 | Blackhurst et al. |
| 9,119,933 B2 | 9/2015 | Bedford et al. |
| 9,132,252 B2 | 9/2015 | Barlow et al. |
| 9,162,035 B2 | 10/2015 | Kwok |
| 9,186,477 B2 | 11/2015 | Hunt et al. |
| 9,205,220 B2 | 12/2015 | Korneff et al. |
| 9,212,673 B2 | 12/2015 | Korneff et al. |
| 9,242,064 B2 | 1/2016 | Rustad et al. |
| 9,254,368 B2 | 2/2016 | Blumenthal et al. |
| 9,289,572 B2 | 3/2016 | Korneff et al. |
| RE46,079 E | 7/2016 | Virr et al. |
| 9,381,317 B2 | 7/2016 | Landis et al. |
| 9,387,299 B2 | 7/2016 | Zwolinsky et al. |
| 9,427,547 B2 | 8/2016 | Landis et al. |
| 9,446,210 B2 | 9/2016 | Orr et al. |
| 9,512,856 B2 | 12/2016 | Nibu |
| 9,517,321 B2 | 12/2016 | Buechi et al. |
| 9,545,493 B2 | 1/2017 | Mayer et al. |
| 9,566,409 B2 | 2/2017 | Gründler et al. |
| 9,572,949 B2 | 2/2017 | Vos et al. |
| 9,572,951 B2 | 2/2017 | Barker et al. |
| 9,586,019 B2 | 3/2017 | Heine et al. |
| 9,642,979 B2 | 5/2017 | Korneff et al. |
| RE46,571 E | 10/2017 | Virr et al. |
| 9,838,759 B2 | 12/2017 | Kirmse et al. |
| 9,861,778 B2 | 1/2018 | Roderick et al. |
| 9,937,314 B2 | 4/2018 | Buechi et al. |
| 9,937,316 B2 | 4/2018 | Buechi et al. |
| 9,974,921 B2 | 5/2018 | Klenner et al. |
| 9,987,455 B2 | 6/2018 | Stoks et al. |
| 10,046,136 B2 | 8/2018 | Pujol |
| 10,105,511 B2 | 10/2018 | Buechi |
| 10,245,407 B2 | 4/2019 | Osborne et al. |
| 10,449,319 B2 | 10/2019 | Osborne et al. |
| 10,828,482 B2 * | 11/2020 | Osborne ............... B60T 17/043 137/381 |
| 10,974,015 B2 | 4/2021 | Stoks et al. |
| 11,129,956 B2 | 9/2021 | Klenner et al. |
| 11,324,911 B2 | 5/2022 | Osborne et al. |
| 11,351,332 B2 | 6/2022 | Mcintyre et al. |
| 11,559,653 B2 | 1/2023 | Osborne et al. |
| 2001/0017134 A1 | 8/2001 | Bahr |
| 2001/0017880 A1 | 8/2001 | Beerwerth et al. |
| 2001/0050080 A1 | 12/2001 | Seakins et al. |
| 2002/0058436 A1 * | 5/2002 | Saba ....................... F16L 25/01 439/191 |
| 2002/0100320 A1 | 8/2002 | Smith et al. |
| 2002/0132511 A1 | 9/2002 | Groebe et al. |
| 2002/0153011 A1 | 10/2002 | Tanhehco |
| 2003/0066526 A1 | 4/2003 | Thurdor et al. |
| 2003/0066530 A1 | 4/2003 | Shahbazpour et al. |
| 2003/0107325 A1 | 6/2003 | Birkhead |
| 2003/0127096 A1 | 7/2003 | McAuliffe |
| 2003/0148664 A1 | 8/2003 | Cheng |
| 2003/0154977 A1 * | 8/2003 | White ................. A61M 16/024 128/203.26 |
| 2003/0183294 A1 | 10/2003 | Carlson |
| 2003/0200727 A1 | 10/2003 | Kim |
| 2003/0236015 A1 | 12/2003 | Edirisuriya et al. |
| 2004/0013162 A1 | 1/2004 | Beerwerth et al. |
| 2004/0055597 A1 | 3/2004 | Virr et al. |
| 2004/0074493 A1 | 4/2004 | Seakins et al. |
| 2004/0079371 A1 | 4/2004 | Gray |
| 2004/0087213 A1 | 5/2004 | Kao |
| 2004/0099268 A1 | 5/2004 | Smith et al. |
| 2004/0101026 A1 | 5/2004 | Nitta et al. |
| 2004/0149284 A1 | 8/2004 | Smith et al. |
| 2004/0168530 A1 | 9/2004 | Adolfs |
| 2004/0182392 A1 | 9/2004 | Gerder et al. |
| 2004/0221843 A1 | 11/2004 | Baecke |
| 2004/0234254 A1 | 11/2004 | Czupich et al. |
| 2004/0239001 A1 | 12/2004 | Edirisuriya et al. |
| 2004/0244858 A1 | 12/2004 | Jeong |
| 2005/0039809 A1 | 2/2005 | Speldrich |
| 2005/0059957 A1 | 3/2005 | Campbell et al. |
| 2005/0152733 A1 | 7/2005 | Patel |
| 2006/0030191 A1 | 2/2006 | Tuin et al. |
| 2006/0118113 A1 | 6/2006 | Bremner et al. |
| 2006/0137445 A1 | 6/2006 | Smith et al. |
| 2006/0150712 A1 | 7/2006 | Berstis et al. |
| 2006/0165829 A1 | 7/2006 | Smith et al. |
| 2006/0196510 A1 | 9/2006 | McDonald |
| 2006/0237012 A1 | 10/2006 | Thudor et al. |
| 2006/0249160 A1 | 11/2006 | Scarberry |
| 2006/0283450 A1 | 12/2006 | Shissler et al. |
| 2007/0039374 A1 | 2/2007 | Borali |
| 2007/0079982 A1 | 4/2007 | Laurent et al. |

(56) References Cited

U.S. PATENT DOCUMENTS

| | | |
|---|---|---|
| 2007/0107737 A1 | 5/2007 | Landis et al. |
| 2007/0110124 A1 | 5/2007 | Shiraki et al. |
| 2007/0144519 A1 | 6/2007 | Henry et al. |
| 2007/0157928 A1 | 7/2007 | Pujol |
| 2007/0169776 A1 | 7/2007 | Kepler et al. |
| 2007/0175473 A1 | 8/2007 | Lewis et al. |
| 2007/0193580 A1* | 8/2007 | Feldhahn .......... A61M 16/0858 128/204.18 |
| 2007/0248934 A1 | 10/2007 | Mosimann |
| 2007/0272240 A1 | 11/2007 | Aylsworth et al. |
| 2007/0284361 A1 | 12/2007 | Nadjafizadeh et al. |
| 2008/0000474 A1 | 1/2008 | Jochle et al. |
| 2008/0015257 A1 | 1/2008 | Grosskreutz et al. |
| 2008/0027344 A1 | 1/2008 | Terry |
| 2008/0028850 A1* | 2/2008 | Payton ............... A61M 16/1005 73/204.19 |
| 2008/0051674 A1 | 2/2008 | Davenport et al. |
| 2008/0053456 A1 | 3/2008 | Brown |
| 2008/0066741 A1* | 3/2008 | LeMahieu ............. A61M 15/00 128/200.21 |
| 2008/0066751 A1 | 3/2008 | Polacsek |
| 2008/0072900 A1 | 3/2008 | Kenyon et al. |
| 2008/0105257 A1 | 5/2008 | Klasek et al. |
| 2008/0142019 A1 | 6/2008 | Lewis et al. |
| 2008/0196716 A1 | 8/2008 | Wachter |
| 2008/0202512 A1 | 8/2008 | Kressierer |
| 2008/0205481 A1 | 8/2008 | Faries |
| 2008/0205979 A1 | 8/2008 | Gombert et al. |
| 2008/0207028 A1 | 8/2008 | Schutz |
| 2008/0251073 A1 | 10/2008 | Jassell et al. |
| 2008/0264413 A1 | 10/2008 | Doherty et al. |
| 2008/0302362 A1 | 12/2008 | Kwok |
| 2008/0308169 A1 | 12/2008 | Nielsen |
| 2009/0041080 A1 | 2/2009 | Koch |
| 2009/0044808 A1 | 2/2009 | Guney et al. |
| 2009/0050150 A1 | 2/2009 | Rossen et al. |
| 2009/0056712 A1 | 3/2009 | Cortez, Jr. et al. |
| 2009/0056713 A1 | 3/2009 | Cortez, Jr. et al. |
| 2009/0078259 A1 | 3/2009 | Kooji et al. |
| 2009/0087259 A1 | 3/2009 | Kooji et al. |
| 2009/0107493 A1 | 4/2009 | Liu et al. |
| 2009/0107496 A1 | 4/2009 | McGhin et al. |
| 2009/0107501 A1 | 4/2009 | Krieger |
| 2009/0107981 A1 | 4/2009 | Andel et al. |
| 2009/0110022 A1 | 4/2009 | Snyder et al. |
| 2009/0110378 A1 | 4/2009 | Bradley et al. |
| 2009/0174092 A1 | 7/2009 | Kwok et al. |
| 2009/0180829 A1 | 7/2009 | Rejman et al. |
| 2009/0223514 A1 | 9/2009 | Smith et al. |
| 2009/0243226 A1* | 10/2009 | Liepold ................ F16J 1/003 277/563 |
| 2009/0247989 A1 | 10/2009 | Burke |
| 2009/0301482 A1 | 12/2009 | Burton et al. |
| 2009/0320840 A1 | 12/2009 | Klasek et al. |
| 2010/0015830 A1 | 1/2010 | Simeon et al. |
| 2010/0083965 A1 | 4/2010 | Virr et al. |
| 2010/0087749 A1 | 4/2010 | Tovey |
| 2010/0102799 A1 | 4/2010 | Schnidrig |
| 2010/0116272 A1 | 5/2010 | Row et al. |
| 2010/0147301 A1 | 6/2010 | Kwok |
| 2010/0154796 A1 | 6/2010 | Smith et al. |
| 2010/0204602 A1 | 8/2010 | Addington et al. |
| 2010/0242963 A1 | 9/2010 | Brieger et al. |
| 2010/0272507 A1 | 10/2010 | Khoe |
| 2010/0292601 A1 | 11/2010 | Dompeling et al. |
| 2011/0017212 A1 | 1/2011 | Kenyon et al. |
| 2011/0023874 A1 | 2/2011 | Bath et al. |
| 2011/0046433 A1 | 2/2011 | Khodak |
| 2011/0046494 A1 | 2/2011 | Balji et al. |
| 2011/0078109 A1 | 3/2011 | Mayer et al. |
| 2011/0088693 A1 | 4/2011 | Somervell et al. |
| 2011/0108028 A1 | 5/2011 | Zollinger |
| 2011/0108031 A1 | 5/2011 | Korneff et al. |
| 2011/0114093 A1 | 5/2011 | Patil et al. |
| 2011/0155132 A1 | 6/2011 | Virr et al. |
| 2011/0180068 A1 | 7/2011 | Kenyon et al. |
| 2011/0186048 A1 | 8/2011 | Casse et al. |
| 2011/0247623 A1 | 10/2011 | McCarthy |
| 2011/0253136 A1 | 10/2011 | Sweeney et al. |
| 2011/0283999 A2 | 11/2011 | Smith et al. |
| 2011/0308518 A1 | 12/2011 | McGroary et al. |
| 2011/0313689 A1 | 12/2011 | Holley et al. |
| 2011/0316562 A1 | 12/2011 | Cefai et al. |
| 2012/0060838 A1 | 3/2012 | Lapoint et al. |
| 2012/0073573 A1 | 3/2012 | Thurdor et al. |
| 2012/0125333 A1 | 5/2012 | Bedford et al. |
| 2012/0125334 A1 | 5/2012 | Korneff et al. |
| 2012/0146251 A1 | 6/2012 | Heine et al. |
| 2012/0174924 A1 | 7/2012 | Smith et al. |
| 2012/0215125 A1 | 8/2012 | Orr et al. |
| 2012/0227738 A1 | 9/2012 | Virr et al. |
| 2012/0234323 A1 | 9/2012 | Connor |
| 2012/0255758 A1 | 10/2012 | Lee |
| 2012/0266880 A1 | 10/2012 | Young |
| 2012/0283570 A1* | 11/2012 | Tegg ..................... A61B 5/283 600/467 |
| 2012/0285448 A1 | 11/2012 | Dugan et al. |
| 2013/0008158 A1 | 1/2013 | Hon |
| 2013/0042867 A1 | 2/2013 | Kwok et al. |
| 2013/0043677 A1 | 2/2013 | Gibson |
| 2013/0079667 A1 | 3/2013 | Berkcan et al. |
| 2013/0081619 A1 | 4/2013 | Seakins et al. |
| 2013/0087143 A1 | 4/2013 | Pujol |
| 2013/0104888 A1 | 5/2013 | Landis et al. |
| 2013/0104901 A1 | 5/2013 | Landis et al. |
| 2013/0112201 A1 | 5/2013 | Graham |
| 2013/0112202 A1 | 5/2013 | Fogelbrink |
| 2013/0152931 A1 | 6/2013 | Sims et al. |
| 2013/0174839 A1 | 7/2013 | Ging et al. |
| 2013/0199529 A1 | 8/2013 | Power et al. |
| 2013/0206140 A1 | 8/2013 | Kepler et al. |
| 2013/0237781 A1 | 9/2013 | Gyrn |
| 2013/0239960 A1 | 9/2013 | Bertinetti et al. |
| 2013/0239966 A1 | 9/2013 | Klasek et al. |
| 2013/0247905 A1 | 9/2013 | Miller et al. |
| 2013/0248044 A1 | 9/2013 | Shiga et al. |
| 2013/0252461 A1* | 9/2013 | Gross ................. H01R 13/5227 439/577 |
| 2013/0255677 A1 | 10/2013 | Varga |
| 2013/0333701 A1 | 12/2013 | Herron |
| 2013/0340752 A1 | 12/2013 | Landis et al. |
| 2014/0001658 A1 | 1/2014 | Virr |
| 2014/0007872 A1 | 1/2014 | Grundler et al. |
| 2014/0020684 A1 | 1/2014 | Klasek et al. |
| 2014/0048065 A1 | 2/2014 | Haroutunian |
| 2014/0090649 A1 | 4/2014 | Groll et al. |
| 2014/0116433 A1 | 5/2014 | Ghalib et al. |
| 2014/0130802 A1 | 5/2014 | Virr et al. |
| 2014/0202460 A1 | 7/2014 | Bath et al. |
| 2014/0202462 A1 | 7/2014 | Stoks |
| 2014/0202463 A1 | 7/2014 | Ging et al. |
| 2014/0216446 A1 | 8/2014 | Wruck |
| 2014/0246021 A1* | 9/2014 | Buechi ................ F16L 37/0925 285/319 |
| 2014/0251322 A1 | 9/2014 | Miller |
| 2014/0251331 A1 | 9/2014 | Korneff et al. |
| 2014/0283829 A1 | 9/2014 | Miller |
| 2014/0311489 A1 | 10/2014 | Heine et al. |
| 2014/0318536 A1 | 10/2014 | Landis et al. |
| 2014/0331786 A1 | 11/2014 | Romano |
| 2014/0338666 A1 | 11/2014 | Visveshwara et al. |
| 2014/0345614 A1 | 11/2014 | Kwok |
| 2014/0366876 A1 | 12/2014 | Huby et al. |
| 2015/0027204 A1 | 1/2015 | Stoks et al. |
| 2015/0040897 A1 | 2/2015 | Buechi |
| 2015/0048530 A1 | 2/2015 | Cheung et al. |
| 2015/0083126 A1 | 3/2015 | Rogers |
| 2015/0083132 A1 | 3/2015 | Jones et al. |
| 2015/0090260 A1 | 4/2015 | Seakins et al. |
| 2015/0096560 A1 | 4/2015 | Klenner et al. |
| 2015/0107588 A1 | 4/2015 | Cheung et al. |
| 2015/0144130 A1 | 5/2015 | O'Donnell et al. |
| 2015/0196725 A1 | 7/2015 | Oates et al. |
| 2015/0359990 A1 | 12/2015 | Barker et al. |

(56) References Cited

U.S. PATENT DOCUMENTS

| | | | |
|---|---|---|---|
| 2016/0008560 | A1 | 1/2016 | Kwok |
| 2016/0015927 | A1 | 1/2016 | Winski et al. |
| 2016/0015937 | A1 | 1/2016 | Winski et al. |
| 2016/0022954 | A1 | 1/2016 | Bath et al. |
| 2016/0051789 | A1 | 2/2016 | Korneff et al. |
| 2016/0089510 | A1 | 3/2016 | Korneff et al. |
| 2016/0101258 | A1 | 4/2016 | Rustad et al. |
| 2016/0199612 | A1 | 7/2016 | Foote et al. |
| 2016/0256642 | A1 | 9/2016 | Soysa et al. |
| 2016/0256657 | A1 | 9/2016 | Klasek et al. |
| 2016/0296721 | A1 | 10/2016 | Landis et al. |
| 2016/0310691 | A1 | 10/2016 | Bath et al. |
| 2016/0367776 | A1 | 12/2016 | Landis et al. |
| 2016/0367779 | A1 | 12/2016 | Landis et al. |
| 2017/0000968 | A1 | 1/2017 | Harrington et al. |
| 2017/0095635 | A1 | 4/2017 | Huby |
| 2017/0136198 | A1 | 5/2017 | Delangre et al. |
| 2017/0151411 | A1 | 6/2017 | Osborne et al. |
| 2017/0161461 | A1 | 6/2017 | Delangre et al. |
| 2017/0173293 | A1 | 6/2017 | Osborne et al. |
| 2017/0197057 | A1 | 7/2017 | Osborne |
| 2017/0239432 | A1 | 8/2017 | Delangre et al. |
| 2017/0326320 | A1 | 11/2017 | Baigent et al. |
| 2018/0078730 | A1 | 3/2018 | Bath et al. |
| 2018/0169361 | A1 | 6/2018 | Dennis et al. |
| 2018/0214660 | A1 | 8/2018 | Stoks et al. |
| 2018/0250491 | A1 | 9/2018 | Row et al. |
| 2018/0296791 | A1 | 10/2018 | Klenner et al. |
| 2019/0197057 | A1 | 6/2019 | Yan et al. |
| 2020/0061329 | A1 | 2/2020 | Mcintyre et al. |
| 2020/0101253 | A1 | 4/2020 | Osborne et al. |
| 2021/0220601 | A1 | 7/2021 | Stoks et al. |
| 2022/0031993 | A1 | 2/2022 | Klenner et al. |
| 2022/0280744 | A1 | 9/2022 | Osborne et al. |
| 2022/0313940 | A1 | 10/2022 | Mcintyre et al. |

FOREIGN PATENT DOCUMENTS

| | | |
|---|---|---|
| AU | 2000071791 | 3/2001 |
| AU | 2001/028104 | 9/2001 |
| AU | 2002244571 | 9/2002 |
| AU | 2007317198 | 5/2008 |
| AU | 2010206053 | 2/2011 |
| AU | 2013201490 | 4/2013 |
| CA | 1202862 | 4/1986 |
| CA | 2464530 | 5/2003 |
| CA | 2495451 | 3/2004 |
| CA | 2535974 | 10/2011 |
| CA | 2393743 | 1/2012 |
| CA | 2852215 | 4/2013 |
| CN | 2243015 | 12/1996 |
| CN | 1598510 | 3/2005 |
| CN | 1688358 | 10/2005 |
| CN | 101541367 | 9/2009 |
| CN | 101666664 | 3/2010 |
| CN | 102844645 A | 12/2012 |
| CN | 201672170 | 12/2015 |
| DE | 3110903 | 9/1982 |
| DE | 3618614 | 12/1987 |
| DE | 4020522 | 1/1992 |
| DE | 4102223 | 7/1992 |
| DE | 19647548 | 5/1998 |
| DE | 19958296 | 9/2001 |
| DE | 20 2004 006 484.7 | 9/2005 |
| DE | 102004030747 | 1/2006 |
| DE | 20 2005 008 152.3 | 10/2006 |
| DE | 20 2005 008 156.6 | 10/2006 |
| DE | 203 21 468.4 | 8/2007 |
| DE | 203 21 469.2 | 8/2007 |
| DE | 203 21 470.6 | 8/2007 |
| DE | 203 21 471.4 | 8/2007 |
| DE | 203 21 472.2 | 8/2007 |
| DE | 20 2006 007 397.3 | 9/2007 |
| DE | 20 2004 021 759.7 | 10/2007 |
| DE | 20 2006 011 754.7 | 12/2007 |
| DE | 201 22 844.0 | 5/2008 |
| DE | 102007003454 | 7/2008 |
| DE | 102007003455 | 8/2008 |
| DE | 102007039391 | 2/2009 |
| DE | 102008001022 | 10/2009 |
| DE | 20 2004 021 757.0 | 9/2010 |
| DE | 20 2004 021 758.9 | 9/2010 |
| DE | 201 22 937.4 | 9/2010 |
| DE | 20 2004 021 756.2 | 10/2010 |
| DE | 20 2004 021 774.0 | 11/2010 |
| DE | 20 2004 021 777.5 | 12/2010 |
| DE | 20 2004 021 794.5 | 2/2011 |
| DE | 20 2004 021 795.3 | 2/2011 |
| DE | 20 2004 021 796.1 | 2/2011 |
| DE | 20 2004 021 798.8 | 2/2011 |
| DE | 20 2006 020 951.4 | 2/2011 |
| DE | 20 2006 020 952.4 | 2/2011 |
| DE | 20 2004 021829.1 | 5/2011 |
| DE | 201 22 943.9 | 5/2011 |
| DE | 201 22 944.7 | 5/2011 |
| DE | 201 22 945.5 | 5/2011 |
| DE | 20 2005 021 927.4 | 6/2011 |
| DE | 20 2006 021 019.9 | 11/2011 |
| DE | 203 21 882.5 | 12/2011 |
| DE | 20 2004 021876.3 | 1/2012 |
| DE | 20 2007 019350.5 | 1/2012 |
| DE | 20 2011 107 902.7 | 1/2012 |
| DE | 20 2010 016 037.5 | 3/2012 |
| DE | 20 2012 007 229.3 | 10/2012 |
| EP | 0111248 | 6/1984 |
| EP | 0050984 | 12/1984 |
| EP | 0201985 | 11/1986 |
| EP | 0291921 | 11/1988 |
| EP | 0535952 | 4/1993 |
| EP | 0567158 | 10/1993 |
| EP | 0232864 | 5/1994 |
| EP | 0672430 | 9/1995 |
| EP | 0885623 | 12/1998 |
| EP | 1262208 | 12/2002 |
| EP | 1352670 | 10/2003 |
| EP | 1396277 | 3/2004 |
| EP | 1535722 | 6/2005 |
| EP | 1646910 | 4/2006 |
| EP | 1129743 | 5/2006 |
| EP | 1669098 | 6/2006 |
| EP | 1035887 | 7/2006 |
| EP | 1683066 | 7/2006 |
| EP | 1457223 B1 | 10/2006 |
| EP | 1741462 | 1/2007 |
| EP | 1055431 | 11/2007 |
| EP | 1924311 | 5/2008 |
| EP | 1933914 | 6/2008 |
| EP | 1979030 | 10/2008 |
| EP | 2079505 | 7/2009 |
| EP | 2089086 | 8/2009 |
| EP | 2101851 | 9/2009 |
| EP | 2195061 | 6/2010 |
| EP | 2236167 | 10/2010 |
| EP | 2282795 | 2/2011 |
| EP | 2307082 | 4/2011 |
| EP | 2335761 | 6/2011 |
| EP | 2340867 | 7/2011 |
| EP | 2355881 | 8/2011 |
| EP | 2133611 | 9/2011 |
| EP | 2415445 | 2/2012 |
| EP | 2471568 | 7/2012 |
| EP | 2498854 | 9/2012 |
| EP | 2281138 | 10/2012 |
| EP | 2514478 | 10/2012 |
| EP | 2575944 | 4/2013 |
| EP | 2629080 | 8/2013 |
| EP | 2640451 | 9/2013 |
| EP | 2651481 | 10/2013 |
| EP | 2654869 | 10/2013 |
| EP | 2667919 | 12/2013 |
| EP | 2522255 | 3/2014 |
| EP | 2703034 A2 | 3/2014 |
| EP | 2760516 | 8/2014 |
| EP | 2830695 | 2/2015 |

(56) References Cited

FOREIGN PATENT DOCUMENTS

| | | |
|---|---|---|
| EP | 2877224 | 6/2015 |
| EP | 2968829 | 1/2016 |
| EP | 3013402 | 5/2016 |
| EP | 1359962 | 8/2016 |
| EP | 3053623 | 8/2016 |
| EP | 3148418 | 4/2017 |
| EP | 3149696 | 4/2017 |
| EP | 3082920 | 10/2017 |
| EP | 3148419 | 1/2018 |
| GB | 1310949 | 3/1973 |
| GB | 1364127 | 8/1974 |
| GB | 2176313 | 12/1986 |
| GB | 2224957 | 5/1990 |
| JP | 59113392 | 6/1984 |
| JP | S63-161973 | 7/1988 |
| JP | H0623051 | 2/1994 |
| JP | 11033119 | 2/1999 |
| JP | 11286058 | 10/1999 |
| JP | 2001095920 | 4/2001 |
| JP | 2001-129091 A | 5/2001 |
| JP | 2001511507 | 8/2001 |
| JP | 2003139276 | 5/2003 |
| JP | 03194747 | 7/2003 |
| JP | 2003275312 | 9/2003 |
| JP | 2008132370 | 6/2008 |
| JP | 4242816 | 3/2009 |
| JP | 44022293 | 2/2010 |
| JP | 2011125618 | 6/2011 |
| JP | 11248076 | 12/2011 |
| JP | H 05208935 | 6/2013 |
| NZ | 564886 | 2/2011 |
| NZ | 587113 | 12/2011 |
| NZ | 586325 | 1/2012 |
| NZ | 583968 | 10/2012 |
| NZ | 597020 | 6/2013 |
| NZ | 600986 | 8/2013 |
| NZ | 604137 | 6/2014 |
| NZ | 610299 | 11/2014 |
| NZ | 630762 | 2/2016 |
| NZ | 625605 | 4/2016 |
| NZ | 710078 | 1/2017 |
| NZ | 710351 | 1/2017 |
| NZ | 631374 | 4/2017 |
| NZ | 631008 | 7/2017 |
| NZ | 733931 | 2/2019 |
| TW | 201245604 | 11/2012 |
| WO | WO 1996/020748 | 7/1996 |
| WO | WO 97/18001 | 5/1997 |
| WO | WO 1997/042475 | 11/1997 |
| WO | WO 2000/029057 | 5/2000 |
| WO | WO 2001/032069 | 5/2001 |
| WO | WO 01/41854 | 6/2001 |
| WO | WO 01/97894 | 12/2001 |
| WO | WO 2002/017991 | 3/2002 |
| WO | WO 02/066106 | 8/2002 |
| WO | WO 02/066107 | 8/2002 |
| WO | WO 2002/066106 | 8/2002 |
| WO | WO 2002/075854 | 9/2002 |
| WO | WO 2003/026721 | 4/2003 |
| WO | WO 2004/011072 | 2/2004 |
| WO | WO 2004/024429 | 3/2004 |
| WO | WO 2004/037330 | 5/2004 |
| WO | WO 2004/092955 | 11/2004 |
| WO | WO 2004/093954 | 11/2004 |
| WO | WO 2004/093955 | 11/2004 |
| WO | WO 2005/011785 | 2/2005 |
| WO | WO 2005/021076 | 3/2005 |
| WO | WO 2006/019323 | 2/2006 |
| WO | WO 2007/019626 | 2/2007 |
| WO | WO 2007/043060 | 4/2007 |
| WO | WO 2007/051230 | 5/2007 |
| WO | WO 2008/055308 | 5/2008 |
| WO | WO 2008/056993 | 5/2008 |
| WO | WO 2008/058328 | 5/2008 |
| WO | WO 2008/060046 | 5/2008 |
| WO | WO 2008/060295 | 5/2008 |
| WO | WO 2008/076230 | 6/2008 |
| WO | WO 2008/097211 | 12/2008 |
| WO | WO 2009/002004 | 12/2008 |
| WO | WO 2009/006586 | 1/2009 |
| WO | WO 2009/022004 | 2/2009 |
| WO | WO 2009/146484 | 12/2009 |
| WO | WO 2010/031125 | 3/2010 |
| WO | WO 2010/031126 | 3/2010 |
| WO | WO 2011/021708 | 2/2011 |
| WO | WO 2011/030251 A1 | 3/2011 |
| WO | WO 2011/059622 | 5/2011 |
| WO | WO 2012/053910 | 4/2012 |
| WO | WO 2012/065999 | 5/2012 |
| WO | WO 2012/065999 A2 | 5/2012 |
| WO | WO 2012/087644 | 6/2012 |
| WO | WO 2012/100291 | 8/2012 |
| WO | WO 2012/164407 | 12/2012 |
| WO | WO 2013/022356 A1 | 2/2013 |
| WO | WO 2013/026901 | 2/2013 |
| WO | WO 2013/045572 | 4/2013 |
| WO | WO 2013/045575 | 4/2013 |
| WO | WO 2013/045575 A1 | 4/2013 |
| WO | WO 2013/045586 | 4/2013 |
| WO | WO 2013/049660 | 4/2013 |
| WO | WO 2013/050907 | 4/2013 |
| WO | WO 2013/127474 | 9/2013 |
| WO | WO 2014/015382 | 1/2014 |
| WO | WO 2014/055407 | 4/2014 |
| WO | WO 2014/077706 | 5/2014 |
| WO | WO 2014/138804 | 9/2014 |
| WO | WO 2014/205513 | 12/2014 |
| WO | WO 2015/060729 | 4/2015 |
| WO | WO 2015/160268 | 10/2015 |
| WO | WO 2015/179916 | 12/2015 |
| WO | WO 2016/042522 | 3/2016 |
| WO | WO 2016/089224 | 6/2016 |
| WO | WO 2016/139645 | 6/2016 |
| WO | WO 2017/027906 | 2/2017 |
| WO | WO 2017/126980 | 7/2017 |

OTHER PUBLICATIONS

Extended European Search Report for Application No. 15803457.9, dated Nov. 28, 2017, 8 pages.
ISR for International App. No. PCT/IB2012/001786, dated Nov. 21, 2012.
ISR for International App. No. PCT/NZ2015/050069, dated Sep. 4, 2015.
ISR for International App No. PCT/NZ2014/000201, dated Jan. 13, 2015, 20 pages.
ISR for International App No. PCT/NZ2015/050011; dated Mar. 19, 2015, 4 pages.
IPRP for International App. No. PCT/NZ2013/000222, dated Jun. 9, 2015.
IPRP for International App. No. PCT/IB2012/001786, dated Aug. 9, 2016.
ISR for International App. No. PCT/NZ2017/050157, dated May 9, 2018, 10 pages.
ISR for International App No. PCT/NZ2013/000075 dated Jun. 24, 2013.
ISR for International App No. PCT/NZ2013/000042, dated Jul. 9, 2013.
Sawyer, Dick, et al. "An introduction to human factors in medical devices." US Department of Health and Human Services, Public Health Service, Food and Drug Administration, Center for Devices and Radiological Health (1996).
The Pacific Energy Association Reporter, Summer Issue, 1992, vol. II, pp. 13-17.
International Search Report, PCT/NZ2014/000201; dated Jan. 13, 2015; 20 pages.

* cited by examiner

CONNECTIONS FOR HUMIDIFICATION SYSTEM

INCORPORATION BY REFERENCE

Any and all applications for which a foreign or domestic priority claim is identified in the Application Data Sheet as filed with the present application are hereby incorporated by reference under 37 CFR 1.57.

The present application is a continuation of U.S. patent application Ser. No. 15/021,673, filed Mar. 11, 2016, which is the national phase under 35 U.S.C. § 371 of PCT International Application No. PCT/NZ2014/000201, filed Sep. 15, 2014, which claims priority benefit of U.S. Provisional Application No. 61/877,784, filed on Sep. 13, 2013; U.S. Provisional Application No. 62/024,969, filed on Jul. 15, 2014; U.S. Provisional Application No. 61/919,485, filed on Dec. 20, 2013; U.S. Provisional Application No. 61/877,566, filed on Sep. 13, 2013; U.S. Provisional Application No. 62/032,462, filed on Aug. 1, 2014; U.S. Provisional Application No. 61/877,622, filed on Sep. 13, 2013; and U.S. Provisional Application No. 61/877,736, filed on Sep. 13, 2013, each of which is hereby incorporated by reference in its entirety.

BACKGROUND

Field

The present disclosure generally relates to devices and methods for providing heated and/or humidified gases to a user. More particularly, certain features, aspects and advantages of the present disclosure relate to apparatuses and techniques that provide for or enable connections between components of a humidification system. Certain features, aspects and advantages of the present disclosure may be used for providing gases to and/or removing gases from a patient, such as in positive airway pressure (PAP), respirator, anaesthesia, ventilator, and/or insufflation systems.

Description of the Related Art

Gases humidification systems deliver heated and humidified gases for various medical procedures, including respiratory therapy, laparoscopy, and the like. These systems can be configured to control temperature and/or humidity. While a variety of such systems have been developed, further improvements of such systems are desired.

Gases humidification systems also include medical circuits comprising various components that can be used to transport heated and/or humidified gases to and from patients. For example, in some breathing circuits, such as PAP or assisted breathing circuits, gases inhaled by a patient are delivered from a heater-humidifier through an inspiratory tube or conduit. As another example, tubes can deliver humidified gas (commonly CO2) into the abdominal cavity in insufflation circuits. This can help prevent dessication or "drying out" of the patient's internal organs, and can decrease the amount of time needed for recovery from surgery. Unheated tubing allows significant heat loss to ambient cooling. This cooling may result in unwanted condensation or "rainout" along the length of the tubing transporting warm, humidified air. Heater wires may extend inside of at least a portion of the tubing forming the circuit to prevent or at least reduce the likelihood of the formation of significant condensation.

While prior arrangements have provided the desired therapies, a need remains for further improvements to the humidification apparatus and methods relating to the same. Accordingly, it is an object of certain features, aspects and advantages of the disclosure to overcome or ameliorate one or more of the disadvantages of the prior art or to at least provide the public with a useful choice.

SUMMARY

A first aspect of the present disclosure involves a cartridge configured to be removably coupled to a heater base for supplying humidified gases to a user. The heater base comprises a base portion. The base portion comprises a heater plate. The heater plate is configured to contact a heat conductive portion of a removable humidification chamber. The cartridge comprises a data storage component. The data storage component is configured to communicate with a processor in the heater base when the cartridge is coupled to the heater base.

In some configurations, the data storage component stores at least one of: data identifying a model of the cartridge, therapy settings, operating parameters, calibration data or an operating algorithm.

In some configurations, the chamber comprises at least one interlocking feature configured to releasably engage at least one corresponding interlocking feature of the humidification chamber when the humidification chamber is installed on the heater base.

In some such configurations, the cartridge comprises a body configured to be coupled to the heater base and sidewalls extending forward from the body when the cartridge is coupled to the heater base. The humidification chamber is configured to be received between the sidewalls when the humidification chamber is installed on the heater base. The at least one interlocking feature of the cartridge comprises two clips. Each clip is mounted in or on one of the sidewalls and has a cantilevered portion and a portion at least partially protruding inwardly from an inner surface of the sidewall. The at least one corresponding interlocking feature of the humidification chamber comprises two recesses formed in an outer body of the humidification chamber. Each recess is configured to receive the protruding portion of one of the clips when the humidification chamber is installed on the heater base. The cantilevered portions of the clips are configured to deflect outward as the humidification chamber is being installed on the heater base.

In some configurations, the cartridge comprises at least one sensor configured to be received in the humidification chamber when the humidification chamber is installed on the heater base. The at least one sensor is configured to measure at least one property of gases flowing through the humidification chamber.

In some such configurations, the calibration data stored on the data storage component of each cartridge comprises data usable by the heater base to calibrate the at least one sensor of that cartridge. The sensor calibration data can be configured to improve accuracy of the at least one sensor.

In some configurations, a receiver is configured to connect with an electrical component of a conduit.

In some configurations, the receiver comprises a component arranged to receive an electrical component, for example, an electrical component of a conduit, in a direction that is generally aligned with a direction of movement of the humidification chamber during connection of the humidification chamber to the heater base.

A second aspect of the present disclosure involves a method of supporting a humidification chamber comprising: providing a first cartridge configuration configured for connection to the humidifier base, and providing a second cartridge configuration configured for connection to the humidifier base, wherein the first cartridge configuration and the second cartridge configuration have distinct physical characteristics from each other and wherein the first cartridge configuration must be disconnected from the humidifier base before the second cartridge configuration can be connected to the humidifier base.

In some configurations, the first cartridge configuration differs from the second cartridge configuration in terms of information or data stored.

In some configurations, coupling the first cartridge configuration and/or the second cartridge configuration can trigger a software update to the humidifier base.

In some configurations, the first and second cartridge configurations include a memory. The memory can be an EEPROM. In some such configurations, the EEPROM allows each cartridge configuration to have a different software configuration. In some configurations, at least one of the first and second cartridges includes at least one sensor. In some such configurations, the memory stores sensor calibration data configured to increase accuracy of the at least one sensor.

A third aspect of the present disclosure involves a connector assembly configured to couple an inspiratory conduit to an outlet port of a humidification chamber. The humidification chamber is configured to be installed on a heater base. The heater base comprises at least one sensor extending from the heater base and configured to be received in an aperture in the outlet port when the humidification chamber is installed on the heater base. The connector assembly comprises a keyhole cutout extending into the connector from a first end configured to be placed over the outlet port. The keyhole is configured to fit around the sensor. The connector assembly comprises an electrical connector configured to be received in a corresponding receptacle on the heater base.

In some configurations, the connector assembly comprises an elbow connector and a conduit connector. The elbow connector is configured to be coupled to the outlet port. The elbow connector comprises the keyhole. The conduit connector is coupled to the inspiratory conduit and is configured to be coupled to the elbow connector. The conduit connector comprises the electrical connector.

In some configurations, an identification component is configured to be measured by the heater base when the electrical connector is received in the receptacle on the heater base, wherein a processor of the heater base is configured to determine a model of the inspiratory conduit based on the measurement of the identification component and the processor is configured to select operational, control, and/or therapy parameters based on the determined model.

In some configurations, the identification component is a resistor having a first resistance value in a first range of values, the inspiratory conduit comprises at least one heater wire having a second resistance value in a second range of values, and the first range of values does not overlap with the second range of values.

A fourth aspect of the present disclosure involves a conduit connector for a humidification system, the humidification system comprising a base unit and a humidification chamber, the humidification chamber being configured to be engageable with the base unit. The conduit connector comprises: an inlet configured to provide a fluid connection to an outlet of the humidification chamber to receive heated and/or humidified gases therefrom; an outlet configured to provide a fluid connection to a conduit for directing the heated and/or humidified gases to or from a patient or other person; and an electrical terminal configured to provide an electrical connection to an electrical terminal associated with the base unit, wherein the conduit connector is configured to make a releasable and lockable connection to the outlet of the humidification chamber, thereby providing the fluid connection from the inlet of the conduit connector to the outlet of the humidification chamber, such that the conduit connector also provides the electrical connection from the electrical terminal of the conduit connector to the electrical terminal associated with the base unit when the humidification chamber is engaged with the base unit and the conduit connector is connected to the outlet of the humidification chamber.

In some configurations, the circuit connector is configured to make the releasable and lockable connection to the outlet of the humidification chamber and the electrical connection from the electrical terminal of the circuit connector to the electrical terminal associated with the base unit in a single direction of motion.

In some configurations, the circuit connector is configured to be connected to the outlet of the humidification chamber before or after the humidification chamber is engaged with the base unit. The circuit connector can be preassembled connected to the outlet of the humidification chamber for shipping and/or storage. The humidification chamber can be configured to be removed from the base unit with the conduit connector attached to the outlet port.

In some configurations, the conduit connector comprises an orientator configured to orientate the conduit connector relative to the outlet of the humidification chamber and/or to orientate the electrical terminal of the conduit connector relative to the electrical terminal associated with the base unit.

The orientator may comprise a recess configured to slidably engage a projection on the outlet of the humidification chamber such that the conduit connector can only be slid onto the outlet of the humidification chamber in a predetermined orientation. Conversely, the orientator may comprise a projection configured to slidably engage a recess in the outlet of the humidification chamber.

The provision of orientation features aids in ensuring that there is alignment of the electrical terminal of the conduit connector with the electrical terminal associated with the base unit, providing increased ease of assembly. Further, the releasable and lockable connection of the conduit connector to the outlet of the humidification chamber can ensure the correct orientation is maintained.

The outlet of the humidification chamber may comprise a first portion that extends substantially vertically from the humidification chamber and a second portion that extends substantially horizontally from the first portion, the second portion being downstream of the first portion, in use, wherein the inlet of the conduit connector is configured to provide a fluid connection to the second portion of the conduit connector. According to this embodiment, the conduit connector may comprise a cutout to accommodate the first portion, the cutout inhibiting or limiting engagement of the conduit connector to the outlet of the humidification chamber when not correctly orientated to accommodate the first portion received in the cutout.

The cutout may be contoured to have a wider opening and a narrower termination, thereby providing tolerance as to the orientation of the conduit connector on initial engagement and correcting the orientation on continued engagement as the conduit connector is pushed towards the outlet of the humidification chamber.

The electrical terminal of the conduit connector may comprise one or more pins or other electrical contact elements configured to, in use, make contact with one or more tracks of a printed circuit board, the electrical terminal associated with the base unit comprising said printed circuit board. Alternatively, the electrical terminal of the conduit connector may comprise a printed circuit board comprising one or more tracks configured to, in use, make contact with one or more pins or other electrical contact elements, the electrical terminal associated with the base unit comprising said one or more pins or other electrical contact elements.

The electrical terminal of the conduit connector may alternatively comprise an edge card configured to, in use, be received in an edge card receptacle, the electrical terminal associated with the base unit comprising said edge card receptacle.

The electrical terminal of the conduit connector may alternatively comprise an edge card receptacle configured to, in use, receive an edge card, the electrical terminal associated with the base unit comprising said edge card.

In some configurations, the humidification chamber is configured to be inserted on the base unit along a first axis, and the edge card is configured to be received in the edge card receptacle along a second axis, wherein the second axis is parallel to the first axis.

Other forms of electrical terminals will be apparent to those skilled in the art and are included within the scope of the present disclosure.

The electrical terminal of the conduit connector may be electrically connected to one or more heater wires and/or one or more sensor wires, the conduit comprising said one or more heater wires and/or said one or more sensor wires, or having said heater wire(s) and/or said sensor wire(s) associated therewith.

The conduit connector may comprise a recess or projection configured to be engaged by a latch of the humidification chamber (the latch preferably being provided on a wall of the outlet of the humidification chamber), thereby providing said releasable and lockable connection of the conduit connector to the outlet of the humidification chamber.

The conduit connector may additionally or alternatively comprise a latch configured to engage a recess or projection of a wall of the outlet of the humidification chamber, thereby providing said releasable and lockable connection of the conduit connector to the outlet of the humidification chamber.

The latch can include one or more buttons protruding outward from the latch and an upper portion of the latch that deflects away from an axial center of the conduit connector when inward force is applied to the one or more buttons. The upper portion of the latch can be configured to engage the recess or projection of the wall of the outlet of the humidification chamber. In some configurations, the upper portion of the latch is configured to disengage the recess or projection of the wall of the outlet of the humidification chamber when inward force is applied to the one or more buttons. The upper portion of the latch can be configured to disengage the recess or projection of the wall of the outlet of the humidification chamber when the upper portion deflects away from the axial center of the conduit connector.

The conduit connector preferably comprises an activator configured for disengaging the latch from the recess or projection to allow removal of the conduit connector from the outlet of the humidification chamber.

The activator may comprise at least one manually depressible button or switch.

At least a portion of the conduit connector may be receivable inside the outlet of the humidification chamber. In some configurations, the circuit connector includes an inner plug portion. The inner plug portion includes an outer groove near a distal end of the inner plug portion. The circuit connector can also include a seal member disposed in the outer groove. The seal member is configured to seal against an inside of the outlet of the humidification chamber when the circuit connector is connected to the outlet. The seal member can be generally T-shaped. The seal member can be generally V-shaped.

A fifth aspect of the present disclosure involves a conduit connector for a humidification system, the humidification system comprising a base unit and a humidification chamber, the conduit connector comprising: an inlet configured to provide a fluid connection to an outlet of the humidification chamber to receive heated and/or humidified gases therefrom; an outlet configured to provide a fluid connection to a conduit for directing heated and/or humidified gases to or from a patient or other person; an electrical terminal configured to provide an electrical connection to an electrical terminal associated with the base unit; and an orientator configured to orientate the conduit connector relative to the outlet of the humidification chamber.

The electrical terminal of the conduit connector is preferably substantially parallel to the inlet of the conduit connector and/or to a direction of engagement used to electrically connect the electrical terminal of the conduit connector to the electrical terminal associated with the base unit, thereby enabling both the electrical and fluid connections to be effected in a single motion.

A sixth aspect of the present disclosure involves a medical tube comprising the conduit connector of the fourth or fifth aspects. The conduit connector may be integral to or connected to a conduit and/or configured to form at least part of an inspiratory limb of a respiratory circuit.

A seventh aspect of the present disclosure involves a humidification chamber for a humidification system, the humidification chamber comprising: an outer wall; an upper wall connected to the outer wall, the outer wall and the upper wall at least partially defining a volume for containing a liquid; an inlet to receive gases into the humidification chamber from a gases source; and an outlet configured to connect to a conduit connector for directing heated and/or humidified gases from the humidification chamber to a patient or other person; wherein the outlet is configured to provide a releasable and lockable connection to the conduit connector and/or comprises an orientator to control the orientation of the conduit connector relative to the outlet.

The orientator may comprise a recess configured to slidably engage a projection on the conduit connector such that the conduit connector can only be slid onto the outlet of the humidification chamber in a predetermined orientation. Conversely, the orientator may comprise a projection configured to slidably engage a recess in the conduit connector such that the conduit connector can only be slid onto the outlet of the humidification chamber in a predetermined orientation.

The outlet of the humidification chamber preferably comprises a first portion that extends substantially vertically from the humidification chamber and a second portion that extends substantially horizontally from the first portion, the second portion being downstream of the first portion, in use.

The humidification chamber may comprise a recess or projection configured to be engaged by a latch of the conduit connector, thereby providing said releasable and lockable connection of the conduit connector to the outlet of the humidification chamber. Alternatively, the humidification chamber may comprise a latch configured to engage a recess or projection of the conduit connector.

The humidification chamber may comprise an activator for disengaging the latch from the recess or projection to allow removal of the conduit connector from the outlet of the humidification chamber.

The activator may comprise at least one manually depressible button or switch.

The outlet of the humidification chamber may be configured to receive at least a portion of the conduit connector inside the outlet of the humidification chamber.

The humidification chamber may comprise an orientator to control orientation of the humidification chamber relative to the base unit.

An eighth aspect of the present disclosure involves a humidification chamber for a humidification system, the humidification chamber comprising: an outer wall; an upper wall connected to the outer wall, the outer wall and the upper wall at least partially defining a volume for containing a liquid; an inlet to receive gases from a gases source; an outlet configured to connect to a conduit connector for directing heated and/or humidified gases to a patient or other person; and an orientator to control orientation of the humidification chamber relative to the base unit.

The orientator may comprise a recess configured to slidably engage a projection on or associated with the base unit such that the humidification chamber can only be engaged with the base unit in a predetermined orientation. Alternatively, the orientator may comprise a projection configured to slidably engage a recess in or associated with the base unit such that the humidification chamber can only be engaged with the base unit in a predetermined orientation.

The orientator is preferably configured to orientate, at least in part, the conduit connector relative to the outlet of the humidification chamber. Additionally or alternatively, the orientator may be configured to orientate, at least in part, an electrical terminal of the conduit connector relative to an electrical terminal associated with the base unit.

In some preferred configurations, the humidification chamber is configured to couple to the base unit, at least in part, via a coupling portion of or associated with the base unit. Additionally or alternatively, at least the electrical terminal of the conduit connector may be configured to connect with an electrical terminal of the coupling portion. Further connections may be provided between the coupling portion and the base unit for exchanging information therebetween and/or electrical power, such as for powering heater wires in the conduit, via the conduit connector.

In some preferred configurations, at least a downstream end of the outlet of the humidification chamber is oriented in a substantially parallel direction to a direction of engagement of the humidification chamber with the base unit. Additionally or alternatively, a direction of engagement of an electrical terminal of the conduit connector to the electrical terminal the base unit and/or a coupling portion of the base unit is substantially parallel to at least a downstream end of the outlet of the humidification chamber, and/or a direction of engagement of the humidification chamber with the base unit.

Preferably, the humidification chamber comprises an outlet configured to connect to the conduit connector of the fourth or fifth aspects.

A ninth aspect of the present disclosure involves a coupler for a humidification system, the coupler comprising: first connections configured to structurally and electrically connect the coupler to a base unit of the humidification system, the base unit configured to operatively engage a humidification chamber; second connections configured to electrically connect the coupler to a conduit connector that is configured to fluidly connect an outlet of the humidification chamber to a conduit to deliver heated and/or humidified gases to a patient or other person, wherein the coupler comprises one or more guide portions for orientating the humidification chamber and/or the conduit connector relative to the base unit as the humidification chamber and/or the conduit connector are brought into engagement with the coupler.

The first and second connections are preferably configured to be made by urging the humidification chamber and/or the conduit connector in substantially the same direction i.e., preferably the directions are parallel.

In some configurations, one of the one or more guide portions includes a groove configured to slidably engage a rail associated with the humidification chamber such that engagement of the humidification chamber with the coupler aligns the humidification chamber with the base unit. The groove can be tapered from front to back. In some configurations, one of the one or more guide portions comprises a rail configured to slidably engage a groove in the humidification chamber such that engagement of the humidification chamber with the coupler aligns the humidification chamber with the base unit.

A tenth aspect of the present disclosure involves a base unit for a humidification system, in which system a humidification chamber is configured to be engageable with the base unit, a conduit connector is configured to fluidly connect to an outlet of the humidification chamber, and an electrical terminal of the conduit connector is configured to electrically connect to an electrical terminal associated with the base unit, the base unit comprising: one or more guide portions for orientating the humidification chamber and/or the conduit connector relative to the base unit as the humidification chamber and/or the conduit connector are brought into engagement with the base unit.

An eleventh aspect of the present disclosure involves a base unit for a humidification system, in which system a humidification chamber is configured to be engageable with the base unit, the humidification chamber comprising an inlet port and an outlet port, at least one sensor probe extending from the base unit and configured to be received in at least one aperture in the inlet port or outlet port, the at least one sensor probe mounted on a flexible mount configured to provide for repeatable insertion depth of the at least one sensor probe in the inlet port or outlet port. In some configurations, the at least one sensor extends from a cartridge coupled to the base unit.

A twelfth aspect of the present disclosure involves a base unit for a humidification system, in which system a humidification chamber is configured to be engageable with the base unit, a conduit connector is configured to fluidly connect to an outlet of the humidification chamber, and an electrical terminal of the conduit connector is configured to electrically connect to an electrical terminal associated with the base unit, wherein the base unit is configured to receive the humidification chamber in a direction substantially the same or parallel to a direction in which the electrical terminal of the base unit is configured to electrically connect to the electrical terminal of the conduit connector.

In some configurations, the base unit further includes a cartridge coupled to the base unit, the humidification chamber and circuit connector configured to be engageable with the cartridge, the cartridge comprising the electrical terminal of the base unit and at least one sensor configured to be received in a port of the humidification chamber, wherein the port of the humidification chamber is configured to receive the at least one sensor in a direction substantially the same or parallel to a direction in which the electrical terminal of the base unit is configured to electrically connect to the electrical terminal of the circuit connector.

A thirteenth aspect of the present disclosure involves a base unit for a humidification system, in which system a humidification chamber is configured to be engageable with the base unit, the humidification chamber comprising an inlet port and an outlet port, two sensor probes extending from the base unit and configured to be received in an aperture in the inlet port of the humidification chamber, wherein the two sensor probes are spaced from each other by a lateral distance and a vertical distance, the lateral and vertical distances selected to reduce heat contamination while maintaining sufficient proximity to a center of the inlet port and sufficient distance from a wall of the inlet port to improve accuracy and reduce wall effects and other potential sources of error. In some configurations the two sensor probes extend from a cartridge coupled to the base unit.

A fourteenth aspect of the present disclosure involves a humidification system comprising: a conduit connector of the fourth or fifth aspects; and/or a medical tube of the sixth aspect; and/or a humidification chamber of the seventh or eighth aspects; and/or a coupler of the ninth aspect; and/or a base unit of the tenth or eleventh aspects.

Electrical and/or fluid and/or structural connections may be effected between the various components listed in the twelfth aspect, with the details thereof being specified with regards the fourth through eleventh aspects.

A fifteenth aspect of the present disclosure involves a humidification system comprising: a base unit; a humidification chamber configured to operatively connect to the base unit, the humidification chamber comprising an outer body defining a container, an inlet port comprising a wall defining a passage into the container, and an outlet port comprising a wall defining a passage out of the container; a conduit connector configured to connect the outlet port to a gases delivery conduit, wherein connection of the conduit connector to the outlet port is made in substantially the same direction as the connection of the humidification chamber to the base unit.

The conduit connector preferably comprises an electrical terminal configured to electrically connect the gases delivery conduit and/or the conduit connector to an electrical terminal associated with the base unit.

The electrical terminal of the conduit connector preferably connects to the electrical terminal associated with the base unit in substantially the same direction as the connection of the conduit connector to the outlet port of the humidification chamber and/or the connection of the humidification chamber to the base unit. Preferably, said direction is substantially horizontal.

Any one or more of the base unit, the humidification chamber, the conduit connector or a coupler provided between the humidification chamber and the base unit may include an orientator to control relative orientation of at least one of the others of the base unit, the humidification chamber, the conduit connector or the coupler.

A sixteenth aspect of the present disclosure involves a humidification system comprising: a base unit; a humidification chamber configured to operatively connect to the base unit, the humidification chamber comprising an outer body defining a container, an inlet port comprising a wall defining a passage into the container, and an outlet port comprising a wall defining a passage out of the container; a conduit connector configured to connect the outlet port to a gases delivery conduit, the conduit connector comprising an electrical terminal configured to electrically connect to an electrical terminal associated with the base unit, wherein any one or more of the base unit, the humidification chamber, the conduit connector or a coupler provided between the humidification chamber and the base unit include an orientator to control relative orientation of at least one of the others of the base unit, the humidification chamber, the conduit connector or the coupler.

The humidification system preferably comprises a pressurized gas source, the pressurized gas source comprising an outlet, the outlet of the pressurized gas source being connected or connectable to the inlet port of the humidification chamber, the humidification chamber defining a flow passage between the pressurized gas source and outlet port.

The conduit connector is preferably configured to provide a releasable and lockable connection to the outlet port of the humidification chamber.

The humidification chamber is preferably releasably and lockably engageable with the base unit.

The conduit connector is preferably not fixedly or lockably attachable to the base unit and/or the conduit connector is not fixedly or lockably attachable to a coupler located between the conduit connector and the base unit.

A seventeenth aspect of the present disclosure involves a method of attaching components of a humidification system, the method comprising: slidably engaging a humidification chamber to a base unit in a first direction; and slidably engaging a conduit connector to an outlet of the humidification chamber in a second direction, wherein the first and second directions are substantially the same.

Preferably, said slidably engaging the conduit connector to the outlet of the humidification chamber results in or effects electrical connection of the conduit connector to the base unit and/or a control module associated with the base unit.

An eighteenth aspect of the present disclosure involves a method of attaching components of a humidification system, the method comprising: slidably engaging a conduit connector to an outlet of a humidification chamber in a first direction; and slidably engaging the humidification chamber and the conduit connector to a base unit in a second direction, wherein the first and second directions are substantially the same.

Preferably, said slidably engaging the humidification chamber and the conduit connector to a base unit results in or effects electrical connection of the conduit connector to the base unit and/or a control module associated with the base unit. In some configurations, the base unit includes at least one sensor configured to be received in an aperture of the humidification chamber, wherein slidably engaging the combined sub-assembly of the humidification chamber and the circuit connector to the base unit results in or effects insertion of the at least one sensor in the aperture. In some such configurations, insertion of the at least one sensor in the aperture and electrical connection of the circuit connector to the base unit and/or a control module associated with the base unit occur in a single motion. The first and second directions are preferably substantially horizontal.

A nineteenth aspect of the present disclosure involves a cartridge for use with a respiratory humidifier. The cartridge includes a housing comprising a rear perimeter and at least one securing member extending upwardly beyond an upper extreme of the rear perimeter of the housing, a compartment defined by the housing and a printed circuit board positioned within the compartment, an electrical connector connected to the printed circuit board and extending rearwardly of the compartment, and a first rearwardly protruding member and a second rearwardly protruding member extending outward beyond the rear perimeter of the housing, the first rearwardly protruding member comprising a first recess and the second rearwardly protruding member comprising a second recess, a first bolt extending from the first recess and a second bolt extending from the second recess, the exposed electrical connector being interposed between the first rearwardly protruding member and the second rearwardly protruding member.

In some configurations, the housing includes an upper surface and a rear surface, the upper surface extending forward a first distance from the rear surface and an upper portion of the securing member extending forward a second distance from the rear surface, the first distance being larger than the second distance. In some configurations, the housing includes at least two securing members separated from each other by a valley. In some such configurations, the opening in the rear surface is circumscribed on three sides by the ridge. The ridge can extend along two lateral sides and a bottom side of the opening. The first and second recesses can extend laterally relative to a rear surface of the housing. The first and second recesses can define openings into the first rearwardly protruding member and the second rearwardly protruding member. The first rearwardly protruding member can have a first side surface and the second rearwardly protruding member can have a second side surface, the first recess defining an opening in the first side surface and the second recess defining an opening in the second side surface. The first and second recesses can be generally vertically aligned relative to the rear surface of the housing. The compartment defined by the housing can be generally water-tight. In some configurations, a first spring is positioned within the first recess and contacts the first bolt, a second spring is positioned within the second recess and contacts the second bolt, a first lever is connected with the first bolt and a second lever is connected with the second bolt.

A twentieth aspect of the present disclosure involves a cartridge for use with a respiratory humidifier that includes a housing comprising a rear surface and at least one securing member extending upwardly beyond an upper extreme of the rear surface of the housing, a compartment defined by the housing, an electrical component positioned within the compartment, an electrical connector connected to the electrical component, the rear surface of the housing defining an opening through which the electrical connector is exposed, a first outwardly extending pin extending laterally outward beyond an immediately adjacent portion of the housing and a second outwardly extending pin extending laterally outward beyond an immediately adjacent portion of the housing, the first outwardly extending pin and the second outwardly extending pin being deflectable inwardly toward each other, and the electrical connector being laterally generally interposed between the first outwardly extending pin and the second outwardly extending pin and vertically generally interposed between the first and second outwardly extending pins and the at least one securing member.

In some configurations, the housing includes an upper laterally extending surface and the at least one securing member extending upward beyond the upper laterally extending surface. In some configurations, with the exception of the electrical connector, the compartment is water-tight. The cartridge can further include a gasket disposed on the rear surface around the electrical connector. In some configurations, a first biasing member biases the first outwardly extending pin outward and a second biasing member biases the second outwardly extending pin outward such that inwardly directed movement of the first outwardly extending pin is opposed by the first biasing member and such that inwardly directed movement of the second outwardly extending pin is opposed by the second biasing member.

A twenty-first aspect of the present disclosure involves a cartridge for use with a respiratory humidifier including a housing comprising an upper laterally extending surface, at least one securing member extending upwardly beyond the upper laterally extending surface of the housing, the housing comprising a rear surface extending downward from the upper laterally extending surface, a first rearwardly protruding element extending rearwardly beyond an immediately adjacent portion of the housing and a second rearwardly protruding element extending rearwardly beyond an immediately adjacent portion of the housing, the first rearwardly protruding element and the second rearwardly protruding element being generally vertically aligned, the first rearward protruding element and the second rearwardly protruding element being positioned vertically lower than the upper laterally extending surface, the first rearwardly protruding element comprising a first deflectable portion and the second rearwardly protruding element comprising a second deflectable portion such that the first deflectable portion and the second deflectable portion are deflectable laterally inward toward each other.

In some configurations, the housing includes a first generally vertically extending sidewall and a second generally vertically extending sidewall, the first deflectable portion extending laterally outward beyond the first generally vertically extending sidewall and the second deflectable portion extending laterally outward beyond the second generally vertically extending sidewall. The first deflectable portion can include a first spring biased sliding bolt member. In some such configurations, the first spring biased sliding bolt member is coupled to a lever that is exposed on a bottom portion of the cartridge. In some configurations, an electrical connector extends rearwardly and is positioned vertically lower than the at least one securing member and is positioned vertically higher than the first and second deflectable portions.

A twenty-second aspect of the present disclosure involves a cartridge for use with a respiratory humidifier including an outer housing comprising a plurality of walls, the plurality of walls defining a cavity and comprising a rear surface, an electrical connector protruding from a lower portion of the outer housing, the electrical connector comprising a ridge and a pin array, the ridge extending along three sides of the pin array, the electrical connector extending in a rearward direction further than any other portion of the outer housing, and a first laterally deflectable member positioned rearwardly of the rear surface and a second laterally deflectable member positioned rearwardly of the rear surface, the first and second laterally deflectable members being positioned vertically lower than a lowermost portion of the pin array when the rear surface is positioned to define a generally vertical plane.

In some configurations, at least a portion of the first laterally deflectable member and at least a portion of the second laterally deflectable member are positioned between the rear surface and an imaginary plane generally parallel with the rear surface positioned at the end of the pin array such that the tips of the pins contact the imaginary plane. A projection of the rear surface can intersect at least a portion of the first laterally deflectable member and at least a portion of the second laterally deflectable member. In some configurations, the plurality of walls includes a lower wall, the first deflectable member and the second deflectable member being positioned vertically higher than the lower wall. The lower wall can be configured to contact a portion of a humidifier chamber in use.

A twenty-third aspect of the present disclosure involves a humidification chamber for a humidification system. The humidification chamber includes an outer wall, an upper wall connected to the outer wall, the outer wall and the upper wall at least partially defining a volume for containing a liquid, an inlet to receive gases from a gases source, an outlet configured to connect to a circuit connector for directing heated and/or humidified gases to a patient or other person, and an orientator to control orientation of the humidification chamber relative to a coupler.

In some configurations, the orientator comprises a recess configured to slidably engage a projection on or associated with the coupler such that the humidification chamber can only be engaged with the coupler in a predetermined orientation. In some configurations, the orientator comprises a projection configured to slidably engage a recess in or associated with the coupler such that the humidification chamber can only be engaged with the coupler in a predetermined orientation. In some configurations, the orientator is configured to orientate, at least in part, the circuit connector relative to the outlet of the humidification chamber. In some configurations the orientator is configured to orientate, at least in part, an electrical terminal of the circuit connector relative to an electrical terminal associated with the coupler. The humidification camber can further include a vertically extending slot along a side of the humidification chamber configured to face toward the coupler, the slot formed by a portion of outer wall extending inwardly toward an interior of the humidification chamber, and a generally horizontal shelf extending across the slot at or near a top of the slot, the shelf configured to inhibit the slot from engaging a portion of the coupler.

A twenty-fourth aspect of the present disclosure involves a circuit connector configured to couple an inspiratory conduit to an outlet port of a humidification chamber and a cartridge coupled to a heater base. The circuit connector includes a mounting region; a head region including contact pads; and a main body region including electrical tracks extending from the contact pads. A length of the edge card is selected to maintain electrical contacts with the cartridge despite play of a position of the humidification chamber in a Y-axis or front to back direction and such that a pneumatic connection between the circuit connector and outlet port is established prior to an electrical connection between the edge card and the cartridge.

In some configurations, the head region includes six contact pads on a top surface and the main body region includes six corresponding electrical tracks on a top surface. In some configurations, an outer two pads are wider than an inner four pads. In some configurations, an outer two pads are longer than an inner four pads.

A twenty-fifth aspect of the present disclosure involves a cartridge for use with a heater base, the heater base configured to receive a humidification chamber having an inlet port and an outlet port, and the outlet port configured to receive a circuit connector comprising an electrical connector. The cartridge includes a receiver configured to receive the electrical connector of the circuit connector; and a shroud disposed above and to the sides of the receiver and extending forward from the cartridge, wherein the shroud is configured to cover a portion of the circuit connector when the circuit connector is coupled to the outlet port, and wherein the shroud is configured to guide insertion of the circuit connector on the outlet port so that the electrical connector is guided into the receiver.

In some configurations, the shroud is configured to reduce the likelihood of spilled liquid coming into contact with the electrical connector. The cartridge can further include a sensor extending forward from the cartridge, the shroud disposed above and to the sides of the sensor, the shroud configured to protect the sensor from damage due to contact with other components during assembly, use, cleaning, or the like. The sensor can be positioned below the receiver. The sensor can be configured to be received in an aperture in the outlet port when the humidification chamber is received on the heater base. In some configurations, a lower portion of the shroud comprises rails configured to engage or support a bottom surface of the circuit connector such that the bottom of the circuit connector rests against a top surface of the rails when the circuit connector is engaged with the outlet port and cartridge to help inhibit or prevent upward rotation of the circuit connector. In some configurations, the cartridge further includes a protrusion positioned below the receiver, wherein the protrusion is configured to engage a post on the outlet port. The protrusion can be horseshoe shaped.

A twenty-sixth aspect of the present disclosure involves a cartridge for use with a heater base, the heater base comprising a processor and/or memory. The cartridge includes one or more sensors; and a memory configured to store sensor calibration data, wherein when the cartridge is coupled to the heater base, the memory of the cartridge is placed in communication with the processor and/or memory of the heater base.

For purposes of summarizing the disclosure and the advantages achieved over the prior art, certain objects and advantages are described herein. It is to be understood that not necessarily all such objects or advantages need to be achieved in accordance with any particular embodiment. Thus, for example, those skilled in the art will recognize that the disclosed configuration or configurations may be embodied or carried out in a manner that achieves or optimizes one advantage or group of advantages as taught or suggested herein without necessarily achieving other objects or advantages as may be taught or suggested herein. All of these embodiments are intended to be within the scope of the disclosure herein. These and other embodiments will become readily apparent to those skilled in the art from the following detailed description having reference to the attached figures, the disclosure not being limited to any particular disclosed embodiment(s).

BRIEF DESCRIPTION OF THE DRAWINGS

These and other features, aspects and advantages of the present disclosure will be described with reference to the following drawings, which are illustrative but should not be limiting of the present disclosure.

DETAILED DESCRIPTION

Certain embodiments and examples of humidification systems are described herein. Those of skill in the art will appreciate that the disclosure extends beyond the specifically disclosed embodiments and/or uses and obvious modifications and equivalents thereof. Thus, it is intended that the scope of the disclosure should not be limited by any particular embodiments described herein.

Humidification System

Figure 1:
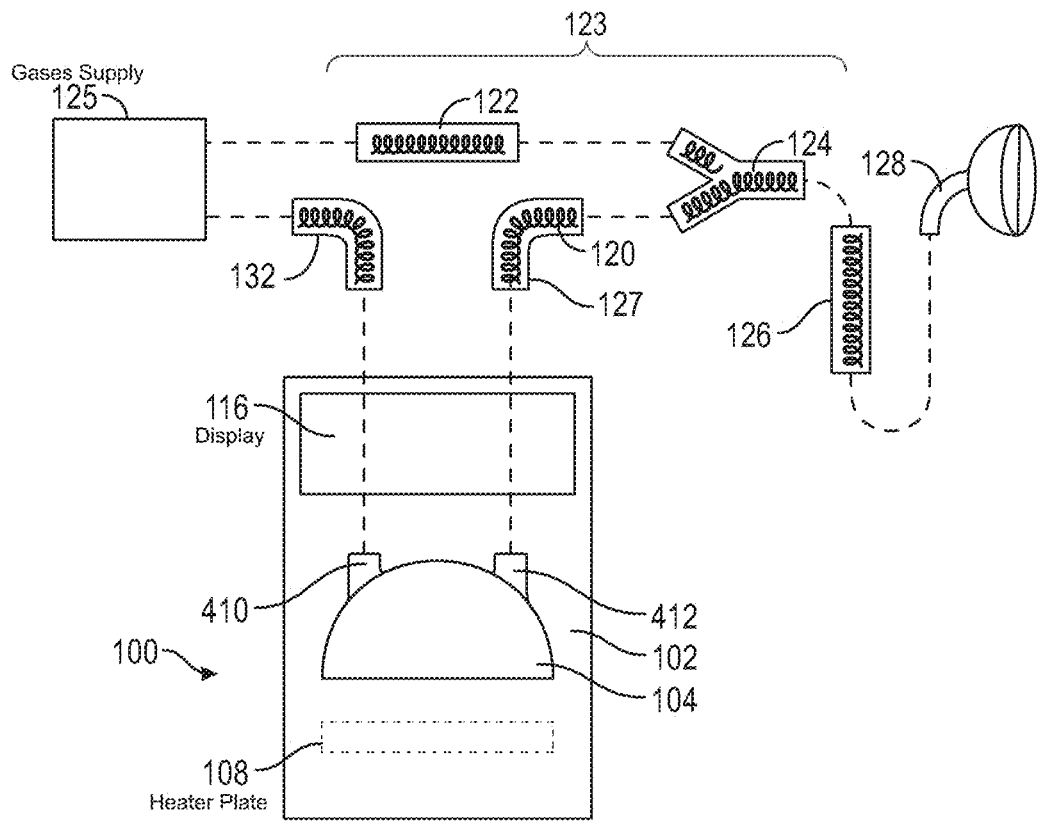
FIG. 1 schematically illustrates an example embodiment of a humidification system.
Figure 1B:
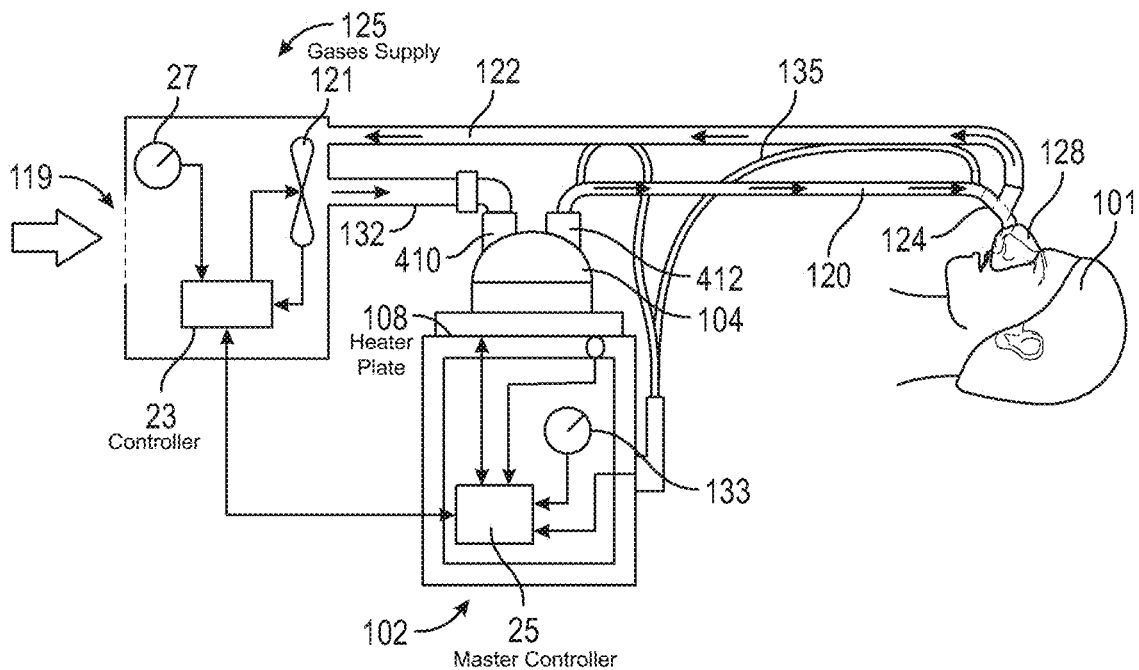
FIG. 1B schematically illustrates another example embodiment of a humidification system.

FIGS. 1A and 1B schematically illustrate example embodiments of a humidification system 100 that, in some applications, can be used with breathing therapies, positive pressure apparatus, noninvasive ventilation, surgical procedures including but not limited to laparoscopy, and the like. Desirably, the humidification system 100 can be adapted to supply humidity or vapor to a supply of gases. The humidification system 100 can be used with continuous, variable, or bi-level positive airway pressure (PAP) systems or other form of respiratory therapy. In some configurations, the humidification system 100 can be integrated into a system that delivers any such types of therapy.

An example embodiment of the humidification system 100 can include a heater base 102 and a humidification chamber 104. The heater base 102 can comprise a heater plate 108. The humidification chamber 104 can be configured to hold a volume of a liquid, such as water. The heater plate 108 can be configured to heat the volume of liquid held within the humidification chamber 104 to produce vapor.

The humidification chamber 104 is removable from the heater base 102 to allow the humidification chamber 104 to be more readily sterilized or disposed. The body of the humidification chamber 104 can be formed from a non-conductive glass or plastics material but the humidification chamber 104 can also include conductive components. For instance, the humidification chamber 104 can include a highly heat-conductive base (for example, an aluminum base) contacting or associated with the heater plate 108 on the heater base 102.

The heater base 102 can also include electronic controls. In this example, the heater base 102 includes a master controller 25. The master controller 25 can comprise an electronic, analog, or digital processor or controller. Preferably, the master controller 25 comprises a microprocessor-based controller configured to execute computer software commands stored in associated memory. In response to user-set humidity or temperature values input via a user interface 133, for example, and other inputs, the master controller 25 determines when (or to what level) to energize the heater plate 108 to heat the liquid within the humidification chamber 104.

The humidification system 100 also can include a gases supply 125. In some configurations, the gases supply 125 can comprise a ventilator, blower, or any other suitable source of pressurized gases suitable for breathing or use in medical procedures. The gases supply 125 can be separate from or combined with the heater base 102.

In some embodiments, for example as shown in FIG. 1B, dry or relatively dry gases enter the gases supply 125 through a vent 119. A fan 121 can improve gas flow into the gases supply by drawing air or other gases through the vent 119. The fan 121 can be, for instance, a variable speed fan, where a controller 23 controls the fan speed. In particular, the function of the controller 23 can be controlled by the master controller 25 in response to inputs from the master controller 25 and a user-set predetermined required value (preset value) of pressure or fan speed via a dial 27.

The humidification system also can include a breathing circuit 123. The breathing circuit 123 can include an inspiratory conduit 120. A chamber end of the inspiratory conduit 120 can be configured to connect to an outlet port 412 of the humidification chamber 104. A patient end of the inspiratory conduit 120 can be configured to connect to the patient, for example, via a patient interface 128. In some configurations, the inspiratory conduit 120 can be coupled directly to the patient interface 128. Any suitable type of the patient interface 128 can be incorporated. Patient interface is a broad term and is to be given its ordinary and customary meaning to a person of ordinary skill in the art (that is, it is not to be limited to a special or customized meaning) and includes, without limitation, masks (such as tracheal masks, face masks and nasal masks), cannulas, and nasal pillows.

A temperature probe 135 can connect to the inspiratory tube 120 near the patient interface 128, or directly to the patient interface 128. The temperature probe 135 monitors the temperature near or at the patient interface 128.

A heating filament (not shown) associated with the temperature probe can be used to adjust the temperature of the patient interface 128 and/or the inspiratory tube 120 to raise the temperature of the inspiratory tube 120 and/or the patient interface 128 above the saturation temperature, thereby reducing the opportunity for unwanted condensation.

In some configurations in which the gases supply 125 is separate from the heater base 102, the breathing circuit 123 can include a supply conduit 132. A gases supply end of the supply conduit 132 can be configured to connect to an output of the gases supply 125. A chamber end of the supply conduit 132 can be configured to connect to an inlet port 410 of the humidification chamber 104.

In some configurations, such as those used with a ventilator, the breathing circuit 123 also can include an expiratory conduit 122. A user end of the expiratory conduit 122 can be configured to connect to the patient interface 128, and a gases supply end of the expiratory conduit 122 can be configured to connect to a return of the gases supply 125. The expiratory tube 122 can have a temperature probe and/or heating filament, as described above with respect to the inspiratory tube 120, integrated with it to reduce the opportunity for condensation. Furthermore, the expiratory tube 122 need not return exhaled gases to the gases supply 125. In some configurations, exhaled gases can be passed directly to ambient surroundings or to other ancillary equipment, such as an air scrubber/filter (not shown). In certain embodiments, the expiratory tube 122 is omitted altogether.

In some embodiments, for example as shown in FIG. 1, the user ends of the inspiratory conduit 120 and the expiratory conduit 122 can be connected to each other via a Y-piece 124. The Y-piece 124 can be connected to a patient supply conduit 126. In some configurations, the patient supply conduit 126 can include a catheter mount, for example but without limitation. The patient supply conduit 126 can be connected to the patient interface 128. In some embodiments, the Y-piece 124 couples to the patient interface 128 without the patient supply conduit 126 intervening.

In use, the humidification chamber 104 is installed on the heater plate 108. The heater plate 108 heats liquid, such as water, in the humidification chamber 104 to produce vapor. Dry or relatively dry gases flow from the gases supply 125, through the supply conduit 132, and into the humidification chamber 104 through the inlet port 410. The gases pass over the liquid in the humidification chamber 104 and become humidified by the vapor. Humidified gases exit the humidification chamber 104 through the outlet port 412 and flow through the inspiratory conduit 120 to a patient 101. In some embodiments, gases exhaled by the patient 101 are returned to the gases supply 125 through the expiratory conduit 122. Any or all of the components of the breathing circuit 123 can include a heating element, for example, a heating wire 127, to help maintain the gases at a desired temperature and to reduce the likelihood of significant condensation formation in the conduits.

Before use, an operator, such as a medical personnel, will connect the various components to set up the humidification system 100. Because of the variety of components and number of connections that are made, setup of the humidification system 100 can be a complex process. In some instances, special training is provided to improve the likelihood of correct setup. The humidification system 100 can include various features to simplify the setup process and reduce the likelihood of an incorrect setup. For example, in some embodiments, components of the humidification system 100 can include features to provide for easier and more secure connection between components, promote correct connections, and reduce the number of connections needed to be made manually or separately.

Chamber to Base Connection

An example embodiment of the heater base 102 is illustrated in FIGS. 2-6. In the illustrated embodiment, the heater base 102 includes a base portion 202. The base portion 202 can include the heater plate 108. The heater base 102 can include a spine 204. The spine 204 can extend upwardly from a rear portion of the base portion 202. The base portion 202 includes side surfaces 206, a top surface 208, and a front surface 210. The spine 204 includes side surfaces 212, a front surface 214, and an upper surface 216. The upper surface 216 can include a display 116 and/or controls. For example, various dials, switches and other input means may be used to control operation of the device. Additionally or alternatively, the display 116 may be a touch screen display. The display 116 may display parameters of the system, warnings in the event of any errors or malfunctions or prompts where user action is required, etc. Where the display 116 is a touch screen display, the display 116 may be used to present information to a user and receive inputs from a user, at least in part.

Figure 15:
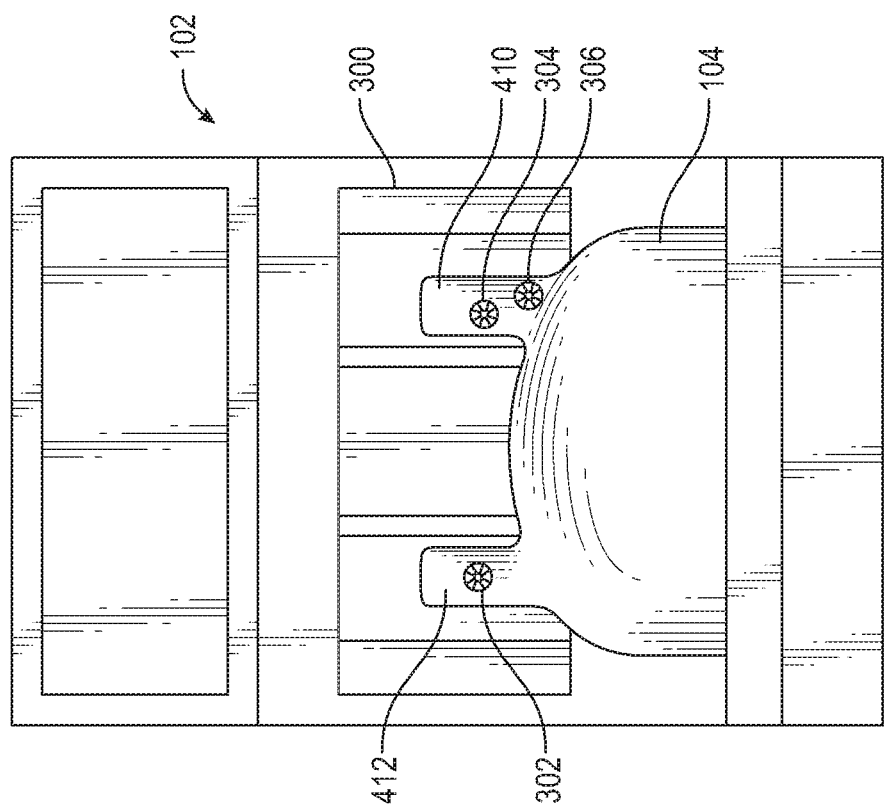
Figure 17:
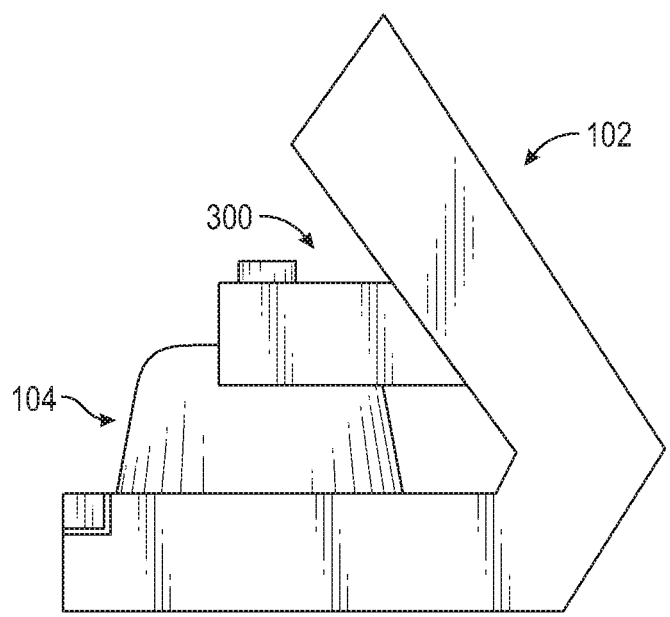

With reference to FIGS. 10-13, the humidification chamber 104 can include a body 402 formed of plastic with a base plate 404 sealed thereto that is heat conductive. In some embodiments, the base plate 404 of the humidification chamber 104 includes a lip 406 that protrudes beyond an outer perimeter of the body 402. In some applications, as shown in FIGS. 14-17, the humidification chamber 104 is configured to be installed on the heater base 102 so that the base plate 404 of the humidification chamber 104 contacts the heater plate 108 of the heater base 102. The humidification chamber 104 is adapted to hold a volume of liquid, such as water, that can be heated by heat conducted through the base plate 404 from the heater plate 108. FIG. 15 schematically illustrates the position of seals or grommets in the humidification chamber 104, where the seals/grommets are positioned on the rear of the humidification chamber 104 and FIG. 15 illustrates a front of the humidification chamber 104.

Figures 2, 2B:
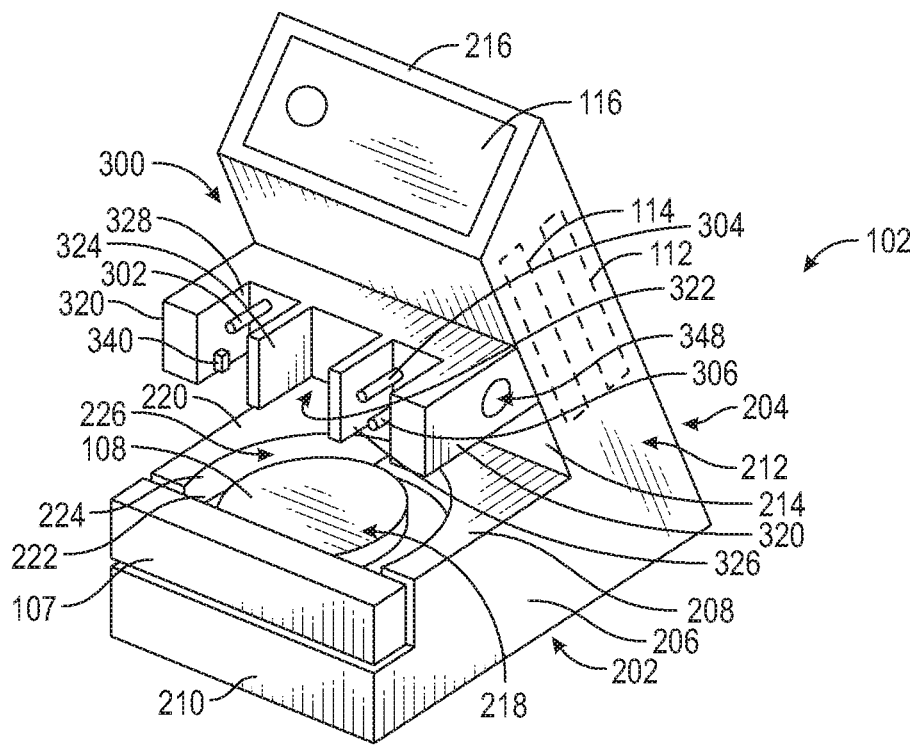
FIGS. 2-6 illustrate views of a heater base that is arranged and configured in accordance with certain features, aspects, and advantages of the present disclosure.

As shown in the partial front section view of FIG. 2B, the top surface 208 of the base portion 202 of the heater base 102 includes an opening 218. The opening 218 is located above the heater plate 108 and allows the humidification chamber 104 to contact the heater plate 108. The upper surface 208 also includes a rim edge 220 along the perimeter of the opening 218.

The heater base 102 includes an inner chassis 222. The inner chassis 222 generally encircles the heater plate 108. The inner chassis 222 also includes a rim edge 224. The rim edge 224 of the inner chassis 222 is positioned generally below the rim edge 220 of the upper surface 208. A groove 226 is formed between the rim edge 220 of the upper surface 208 and the rim edge 224 of the inner chassis 222. The groove 226 can have a thickness of, for example, about 4 mm. The thickness of the groove is large enough to accommodate the lip 406 of the humidification chamber 104 and small enough to significantly limit a generally vertical range of motion of the lip 406 (and the associated humidification chamber 104) relative to the heater base 102. In some embodiments, the thickness of the groove is large enough to accommodate various configurations of chambers. In some embodiments, the diameter of the groove is large enough to accommodate various configurations of chambers.

For use, an operator installs the humidification chamber 104 on the heater base 102 by sliding the humidification chamber 104 onto the heater plate 108. The lip 406 of the humidification chamber 104 rests in, or is trapped within, the groove 226. The heater plate 108 can be spring loaded in some configurations. The spring loading allows the heater plate 108 to be depressed when installing the humidification chamber 104. When the humidification chamber 104 is installed, the spring-loaded heater plate 108 presses upward on the humidification chamber 104 while the rim edge 220 of the upper surface 208 resists upward movement of the lip 406. The rim edge 220 helps resist upward movement of the humidification chamber 104, which, when used in combination with the spring-biased heater plate 108, promotes contact between the base plate 404 and heater plate 108.

The rim edge 224 of the inner chassis 222 and the groove 226 also help inhibit excessive downward movement of the humidification chamber 104. In some configurations, the rim edge 224 of the inner chassis 222 serves to limit downward travel of the humidification chamber 104 relative to the heater base 102. In some configurations, the heater plate 108 or a structure that can abut at least a portion of the heater plate 108 can be configured to limit downward travel of the humidification chamber 104 relative to the heater base 102. Limiting the downward movement of the humidification chamber 104 relative to the heater base 102 can help reduce the likelihood of damage to other components of the system. For example, sensors can be mounted on the heater base 102 as described in greater detail herein; without the rim edge 224 interacting with the humidification chamber 104, the heater plate 108 may be depressed if downward pressure is applied to the humidification chamber 104 when connecting the supply conduit 132 and/or the inspiratory conduit 120. Without the rim edge 224 interacting with the humidification chamber 104, the humidification chamber 104 may have a vertical range of motion of about 2 mm to about 5 mm. The rim edge 224 can reduce the range of motion to about 0.5 mm. Limiting vertical travel of the humidification chamber 104 can reduce the likelihood of the humidification chamber 104 damaging sensors or other components that extend into the humidification chamber 104 from a stationary portion of the system. The rim edge 224 also helps promote more accurate positioning of the humidification chamber 104 on the heater base 102.

In some embodiments, a guard 107 extends along a front portion of the base portion 202 of the heater base 102 and the rim edge 220. The guard 107 can be depressed to enable the base plate 404 and the lip 406 of the humidification chamber 104 to contact the heater plate 108 and the groove 226. The guard 107 can be allowed to revert to a non-depressed position once the humidification chamber 104 has been installed. In the non-depressed position, the guard 107 retains the humidification chamber 104 against inadvertent removal from or significant movement (e.g., significant forward movement) relative to the heater base 102. As shown in FIG. 2, the guard 107 has a vertical dimension that shields at least the heater plate 108. In other words, when in the non-depressed position, the uppermost extent of the guard 107 is vertically higher than the top of the heater plate. As such, the guard 107 provides some degree of protection by serving as a shield to limit the likelihood of inadvertent human contact with the heater plate 108 or other heated components of the system when the guard 107 is in the nondepressed position.

As shown in FIGS. 21-23 and 28-32, in some embodiments, a humidification chamber 1004, 1104 includes gripping portions 1036, 1436. The gripping portions 1036, 1436 can advantageously allow the user to grip the humidification chamber 1004, 1104 more easily when installing or removing the humidification chamber 1004, 1104 from the heater base 102.

Figure 73:
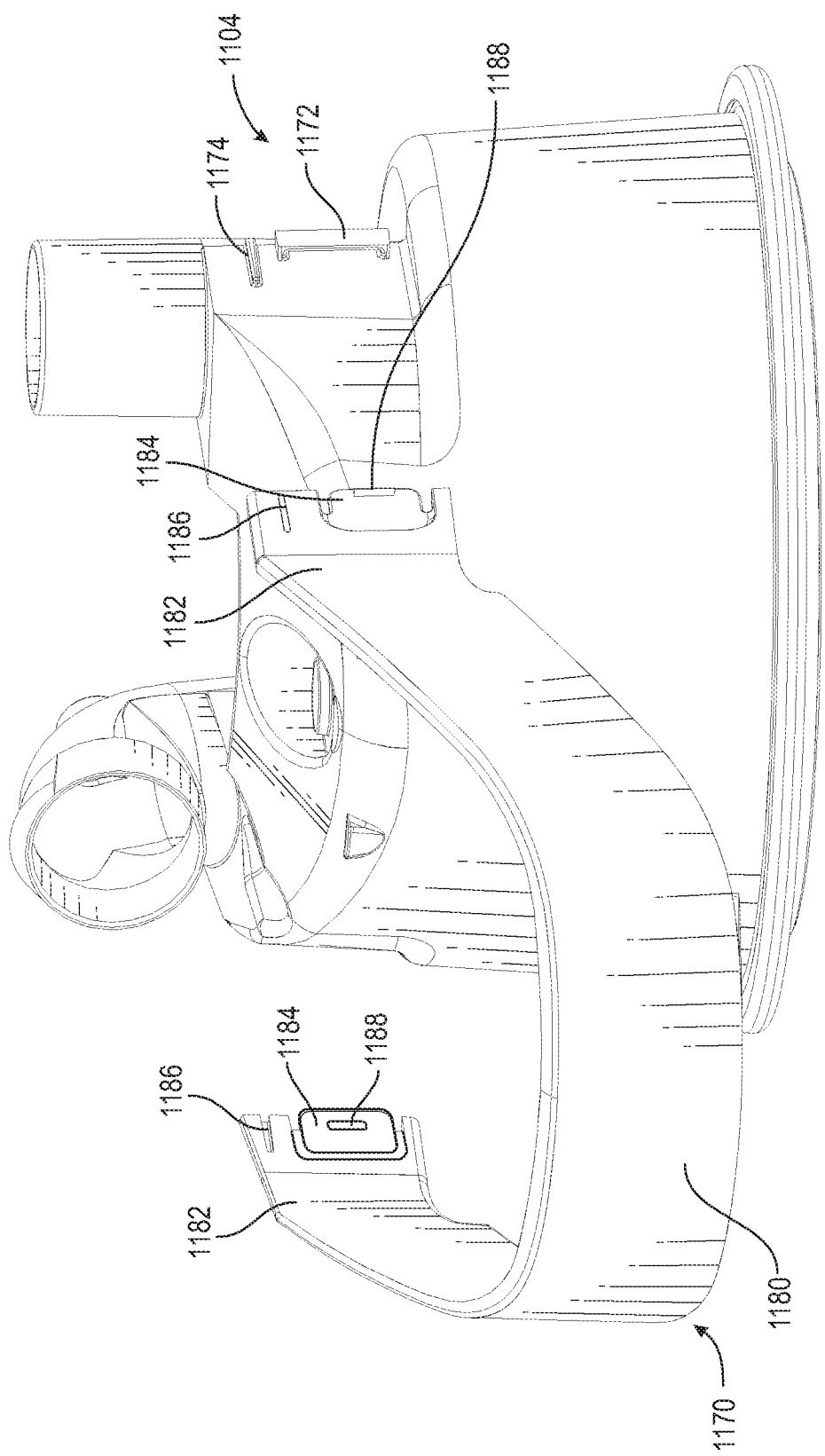
FIG. 73 is an exploded view of a handle and a humidification chamber.

With reference to FIG. 73, the humidification chamber 1104 can comprise a handle 1170. The handle 1170 can be secured to the humidification chamber 1104 in any suitable manner. In the illustrated configuration, the humidification chamber 1104 includes a pair of bridges 1172 and a pair of fins 1174, with one of the bridges 1172 and one of the fins 1174 on each side of the humidification chamber 1104. The handle 1170 can have a main body 1180 with a pair of wings 1182 that curve rearward and upward from the main body 1180. At the end of the wings 1182, the handle 1170 has a pair of tabs 1184 and a pair of slots 1186. The tabs 1184 can be received within passages defined by the bridges 1172 of the humidification chamber 1104 while the fins 1174 of the humidification chamber 1104 can be received within the slots 1186 of the handle 1170. The ends of the tabs 1184 can include raised bosses 1188 that lock the tabs 1184 in position within the bridges 1172. Advantageously, by using the illustrated snap together assembly, the handle 1170 can be secured to the humidification chamber 1104 without the use of adhesives, solvents, or the like. Other configurations are possible, however.

Chamber to Cartridge Connection

The heater base 102 can include a coupling portion coupled to the front surface 214 of the spine 204. In some embodiments, the coupling portion is a cartridge 300 as shown in FIGS. 2-6. The cartridge 300 can include or support various sensors, probes, sensor wire connectors, heater wire connectors, and/or other features. In some embodiments, the cartridge 300 includes features configured to mate with corresponding features on the humidification chamber 104.

Any suitable components can be used as sensors. For example, thermocouples, resistance temperature detectors, fixed resistors and the like can be used as sensors. Sensors can be mounted directly onto the cartridge 300 or in probes or other housings that are mounted onto the cartridge 300. Such probes or other housings can also contain components other than sensors. The cartridge 300 can also be arranged in any suitable configuration or arrangement. In the embodiment of FIGS. 2-6, the cartridge 300 includes a first probe 302 positioned on a first portion of the cartridge 300 and second and third probes 304, 306 positioned on a second portion of the cartridge 300. In some configurations, the first and second portions can be separated by a generally vertically extending plane. In some configurations, the generally vertically extending plane substantially bisects the heater base 102. In some configurations, the generally vertically extending plane substantially bisects the humidification chamber 104 when the humidification chamber 104 is positioned on the heater base 102 for use. The probes 302, 304, 306 extend forward from the cartridge 300. The probes 302, 304, 306 have thermistors mounted at the tips. Other configurations can be used and other types of sensors can be used.

In some embodiments, the inlet port 410 and/or the outlet port 412 include one or more apertures extending through the wall of the respective port. In the embodiment shown in FIG. 11, the inlet port 410 of the humidification chamber 104 includes two apertures 414a, 414b extending through a rear wall of the inlet port 410. The outlet port 412 includes an aperture 416 extending through a rear wall of the outlet port 412. In the illustrated configuration, at least a portion of the each of the inlet port 410 and the outlet port 412 can have a respective flattened region 470, 472. The apertures 414a, 414b, 416 extend through the flattened regions 470, 472. The flattened regions 472, 472 generally surround the apertures 414a, 414b, 416.

The aperture 416 in the outlet port 412 is configured to receive the first probe 302 when the humidification chamber 104 is installed on the heater base 102. Similarly, the apertures 414a, 414b in the inlet port 410 are configured to receive the second and third probes 304, 306, respectively, when the humidification chamber 104 is installed on the heater base 102. In the illustrated configuration, one or more of the probes 302, 304, 306 extend into the inlet port 410 and the outlet port 412. In some configurations, one or more of the probes 302, 304, 306 extends into a portion of the humidification chamber 104 other than the inlet port 410 or the outlet port 412. In some configurations, one or more of the probes 302, 304, 306 extends into a portion of the humidification chamber 104 other than the inlet port 410 or the outlet port 412 while one or more of the probes 302, 304, 306 extends into one or more of the inlet port 410 and the outlet port 412. The probes 302, 304, 306 extend into the outlet port 412 and inlet port 410 along axes parallel to an insertion axis along which the humidification chamber 104 is installed on the heater base 102. Mounting the probes 302, 304, 306 on the cartridge 300 can advantageously allow for reuse of the sensors for multiple instances of the humidification chamber 104

In some embodiments, the thermistor of the first probe 302 is configured to sense temperature of gases in the gas flow path. In some embodiments, the thermistors of the second and third probes 304, 306 are configured to sense a flow rate of gases in the gas flow path using a temperature flow measurement approach. In this approach, one of the thermistors functions as a reference sensor that measures the flow temperature at the sensing location and the other thermistor, which can be a heated thermistor, is heated to a preset temperature differential above the flow temperature. In some embodiments, the heated thermistor is heated to a set temperature, e.g., at or about 160 degrees Celsius. In some applications, a resistor can be used to heat the thermistor instead of using a heated thermistor. In some applications, a resistor can be used instead of a thermistor. In some configurations, all of the thermistors can be both heated and non-heated thermistors. Flow velocity can be determined using the measured flow temperature, the known heat transfer characteristics of the heated thermistor and the power consumed to maintain the temperature difference between the second and third thermistors. Other techniques also can be used. For example but without limitation, constant power can be provided to the thermistors and the heat conducted into a nearby thermistor can be used to determine the rate of flow. However, other types of sensors are also possible.

Seals

Figure 12:
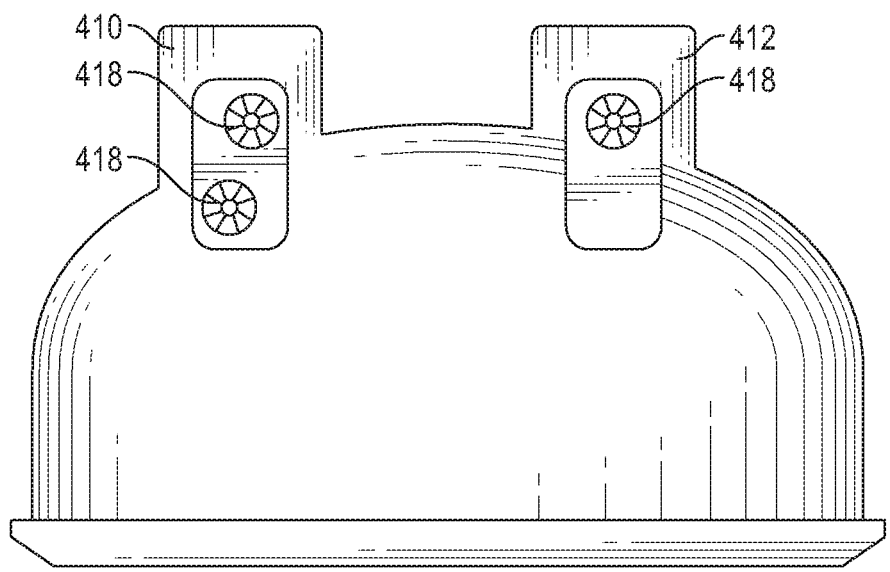

As shown in FIG. 12, seals or grommets 418 can be inserted in the apertures 414a, 414b, 416. The seals or grommets 418 can at least substantially pneumatically seal the apertures 414a, 414b, 416. The seals or grommets 418 help isolate the gas flow path through the humidification chamber 104 from ambient while using the probes 302, 304, 306. Accordingly, in the illustrated configuration, the seals 418 define a barrier that reduces the likelihood of fluid or gas passing through the apertures 414a, 414b, 416. In some applications, at least one of the seals 418, and preferably all of the seals 418, also can be generally resistant to the passage of vapor. The seals 418 can be configured to receive the probes 302, 304, 306. In some configurations, the seals 418 allow the probes 302, 304, 306 to detect properties of gases flowing through the humidification system while remaining substantially pneumatically sealed from the gas flow path. The seals 418 advantageously allow the probes 302, 304, 306 to function without being in direct contact with gases in the gas flow path, so the probes 302, 304, 306 can be reused and do not require cleaning between uses.

The seals 418 can be formed from any suitable material. In some applications, the seals 418 are formed from a resilient or flexible material. In some applications, one or more of the seals 418 can be formed of a material with a Shore-A hardness of between about 20 and about 80, and more preferably between about 40 and about 60. In some applications, one or more of the seals 418 can be formed of Silicone, polyethylene, or thermoplastic polyurethane.

In some embodiments, when one of the probes 302, 304, 306 is inserted into one of the seals 418, the one of the seals 418 stretches to accommodate the one of the probes 302, 304, 306. In some configurations, when one of the probes 302, 304, 306 is inserted into one of the seals 418, the one of the seals 418 conforms to the shape of the one of the probes 302, 304, 306. As the amount of stretch to accommodate the probes increases, the seal material becomes thinner. In some configurations, different regions of the seals 418 can be differing degrees of stretchability. In other words, some portions of the seals 418 are more elastic than other portions of the seals 418. This can advantageously improve the reactivity and accuracy of the sensor, increase the contact area between the sensor and the seal, and/or more securely hold the seal in the aperture.

Probe Placement

The apertures 414a, 414b in the inlet port 410 and the probes 304, 306 can be configured and can be positioned to improve the accuracy of the sensors. For example, positioning the probes 304, 306 closer to the center of the gas flow path through the inlet port 410 can increase accuracy. Positioning the probes 304, 306 closer to the center of the gas flow path can also help reduce errors that may be introduced if the probes 304, 306 are too close to the wall of the inlet port 410. For example, positioning the probes 304, 306 too close to the wall of the inlet port 410 can introduce wall effects, boundary layer effects, error due to thermal coupling, and/or other potential sources of error. However, it has been found that positioning the probes 304, 306 too close to one another also can cause errors due to heat contamination.

Figure 3:
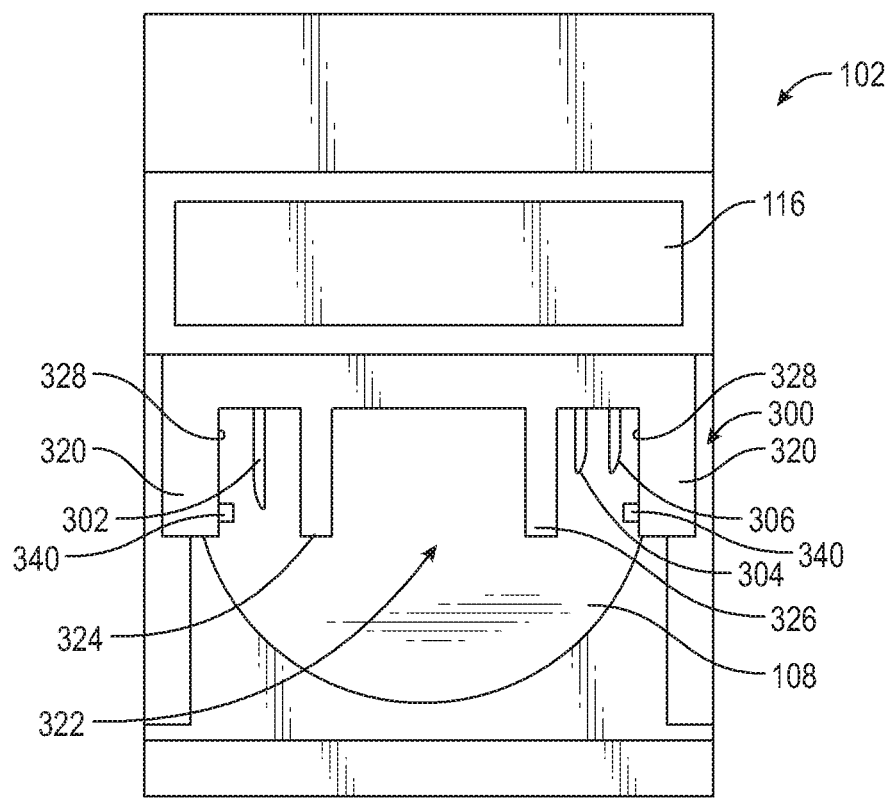
Figure 5:
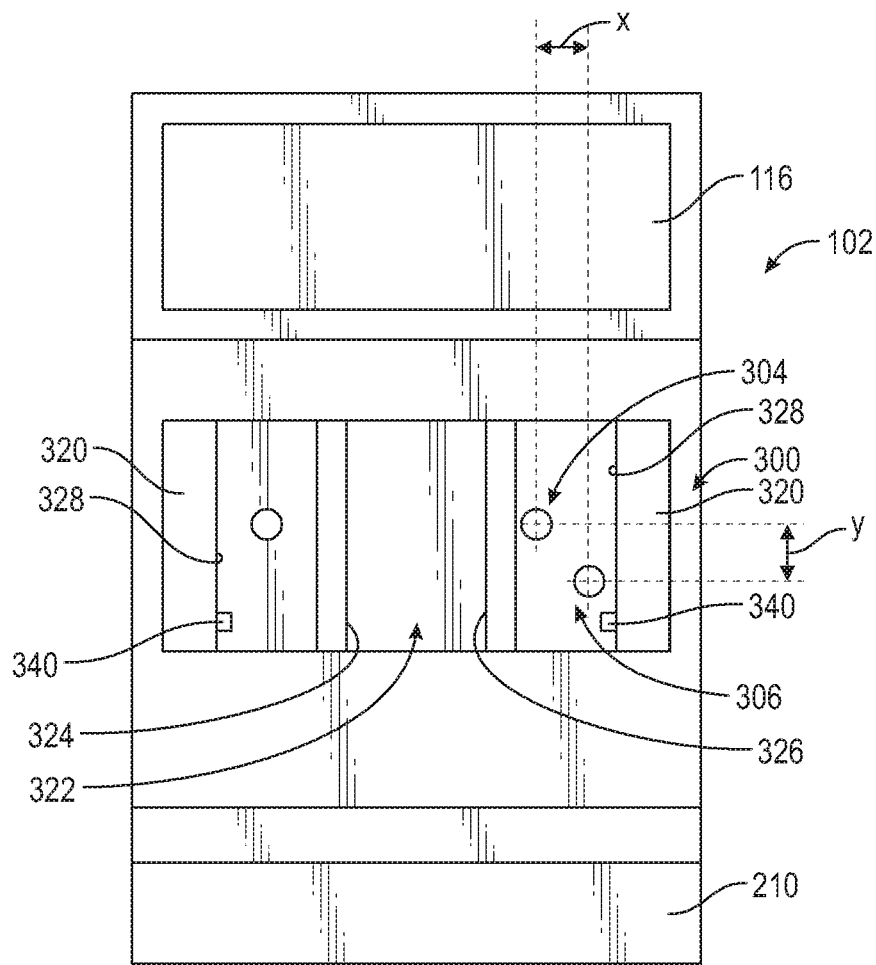
Figure 6:
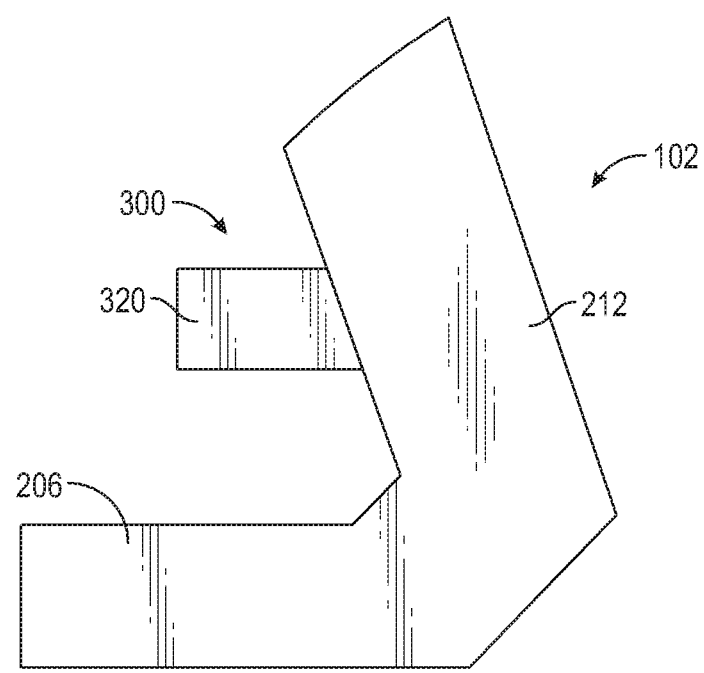

Therefore, in some applications, it is desirable to maximize lateral displacement of the probes 304, 306 from one another to reduce heat contamination while also maintaining sufficient proximity to the center of the inlet port 410 and sufficient distance from the wall of the inlet port 410 to improve accuracy and reduce wall effects and other potential sources of error. In some embodiments, the probes 304, 306 are positioned such that the centers of the probes 304, 306 are separated by a horizontal distance x of about 7 mm as shown in FIG. 5. In some embodiments, the probes 304, 306 are positioned such that the centers of the probes 304, 306 are separated by a vertical distance y of about 7 mm as shown in FIG. 5. In some embodiments, the centers of the probes 304, 306 can be separated by horizontal and vertical distances in the range of about 5 mm to about 7 mm or greater than 7 mm. For example, the centers of the probes 304, 306 can be separated by a vertical distance of about 8 mm and a horizontal distance of about 11 mm. Increasing the spacing between the probes 304, 306 may require an increase in the size of the flattened region 470, which can result in a need for a larger port or a reduced cross-sectional area of the port. Therefore, the spacing between the probes 304, 306 can be selected to maximize separation between the probes 304, 306 while maintaining dimensions of the inlet port 410 within a desired range. For example, in some embodiments, the inlet port 410 has a diameter of about 22 mm. In some embodiments, as shown in FIGS. 2, 3, and 5, when the heater base 102 and the cartridge 300 are viewed from the front, the probe 304 is about 7 mm to the left and about 7 mm vertically higher than the probe 306. In some embodiments, the probe 304 is about 7 mm to the left and about 6.35 mm vertically higher than the probe 306. In some such embodiments, the apertures 414a, 414b, 416 have a diameter in the range of about 3 mm to about 12 mm, for example, about 4 mm to about 8 mm. In some embodiments, the apertures 414a, 414b, 416 have a diameter of about 6 mm.

In some embodiments, the lengths of the probes 302, 304, 306 are selected to allow the thermistors or other sensors to be positioned near the center of the gas flow path through the inlet port 410 and the outlet port 412. The axial lengths of the probes 302, 304, 306 and the sizing of the seals 418 can be interrelated to help promote more uniform stretching of the seals 418.

Figure 18:
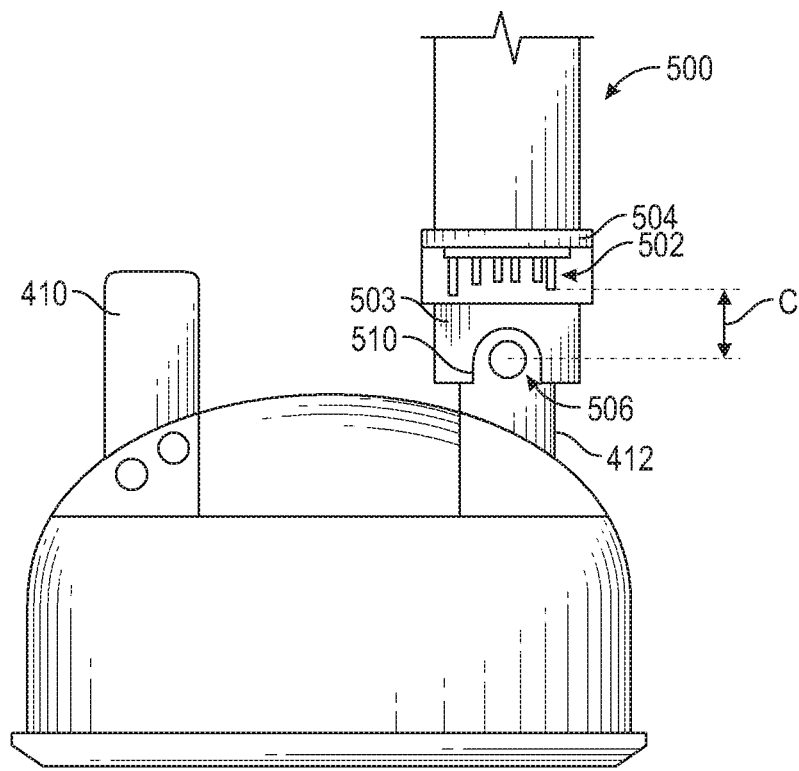
FIGS. 18-20 are views of a conduit connector coupled to the humidification chamber.
Figure 21:
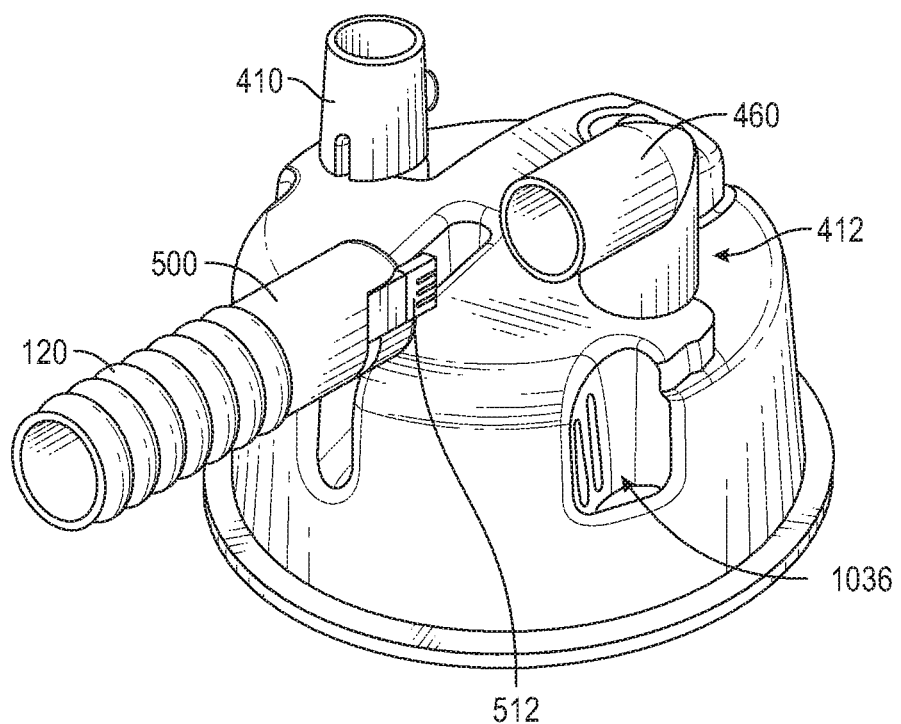
FIGS. 21-24 illustrate alternative conduit connectors.
Figure 22:
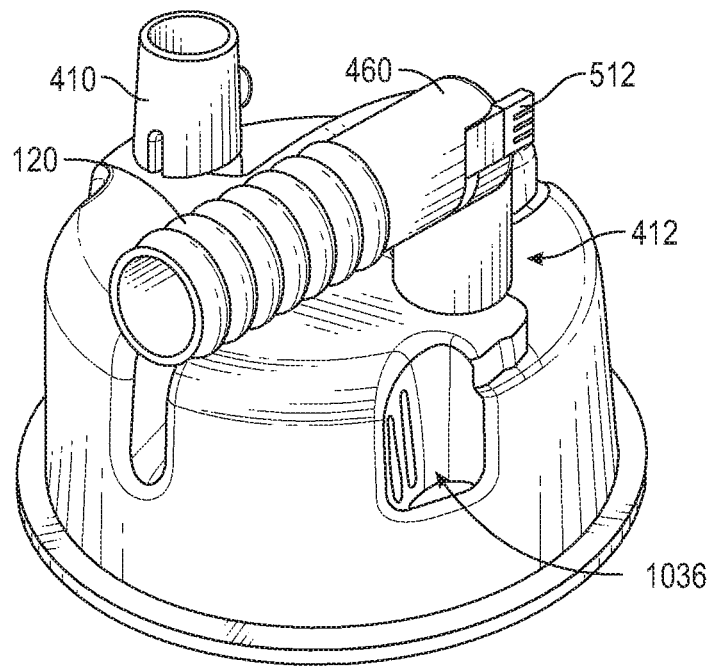
Figure 23:
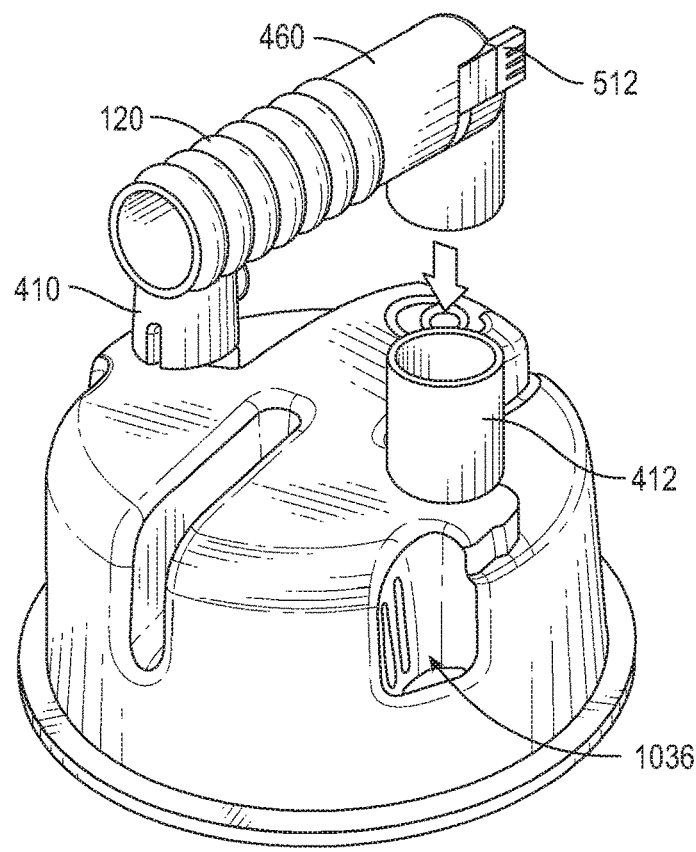

In some configurations, the first probe 302 is positioned to increase the proximity of the first probe 302 to the beginning of the heated part of the inspiratory conduit. For example, in some embodiments, for example as illustrated in FIG. 18, the first probe 302 is positioned vertically higher than the second probe 304. In some embodiments, the first probe 302 is positioned vertically higher than the third probe 306. In the illustrated embodiment, the first probe 302 is positioned vertically higher than the second and third probes 304, 306. In some configurations, the first probe 302 is positioned closer to an outlet of the respective port compared to the second and third probes 304, 306. The position of the first probe 302 can advantageously allow for sensing the temperature of the gases closer to the beginning of the heated part of the inspiratory conduit. In some applications, this can allow for more precise sensing of the temperature of gases traveling in the inspiratory conduit. In other words, the port is not heated while the inspiratory conduit may be heated. By sensing as close to the inlet into the heated inspiratory conduit, there is less travel of the gases through an unheated region, which allows more precision in the measurement of the gases flowing through the inspiratory conduit and which facilitates improved control over the heaters used in conjunction with the inspiratory conduit. In some embodiments, the first probe 302 may extend farther forward or away from the cartridge 300 than the second and third probes 304, 306. Such an arrangement can advantageously allow the first probe 302 to be closer to the beginning of the heated part of the inspiratory conduit in an embodiment such as shown in FIGS. 21-23 and described in greater detail herein.

Spring Probe Assembly

In some embodiments, one or more of the probes 302, 304, 306 are mounted on a spring or resilient member or flexible mount. For example, in the embodiment shown in FIG. 7A, the probe 302 is mounted on a resilient member 308, and the probes 304, 306 are mounted on a resilient member 310. A single resilient member can support one probe in some configurations. In some configurations, a single resilient member can support two probes. In some configurations, a single resilient member can support two or more probes.

Figure 7A:
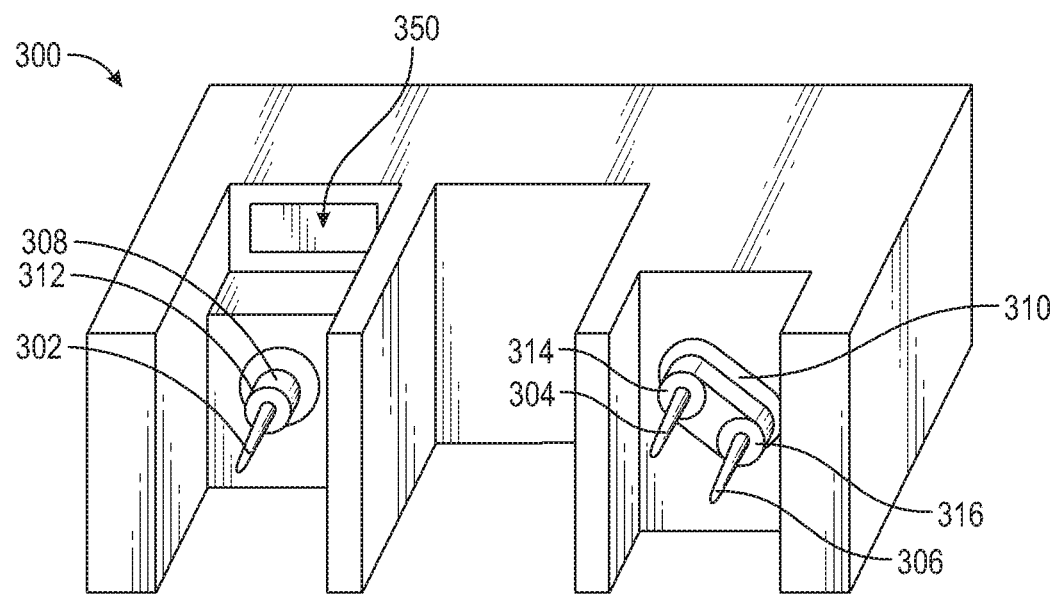
FIG. 7A illustrates an embodiment of a cartridge.
Figure 7B:
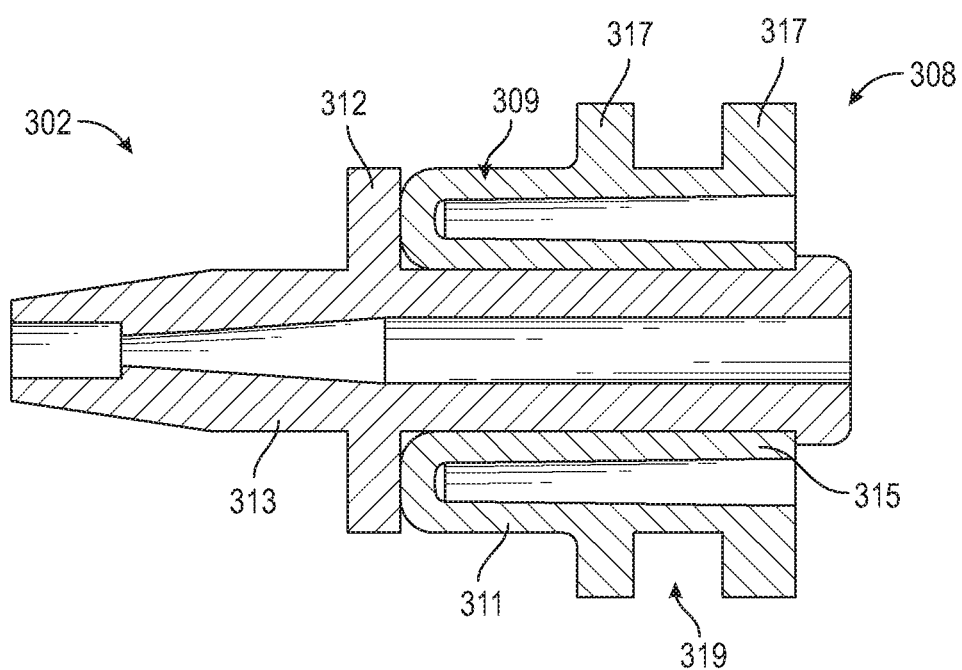
FIG. 7B is a section through a probe and a resilient member.
Figure 7D:
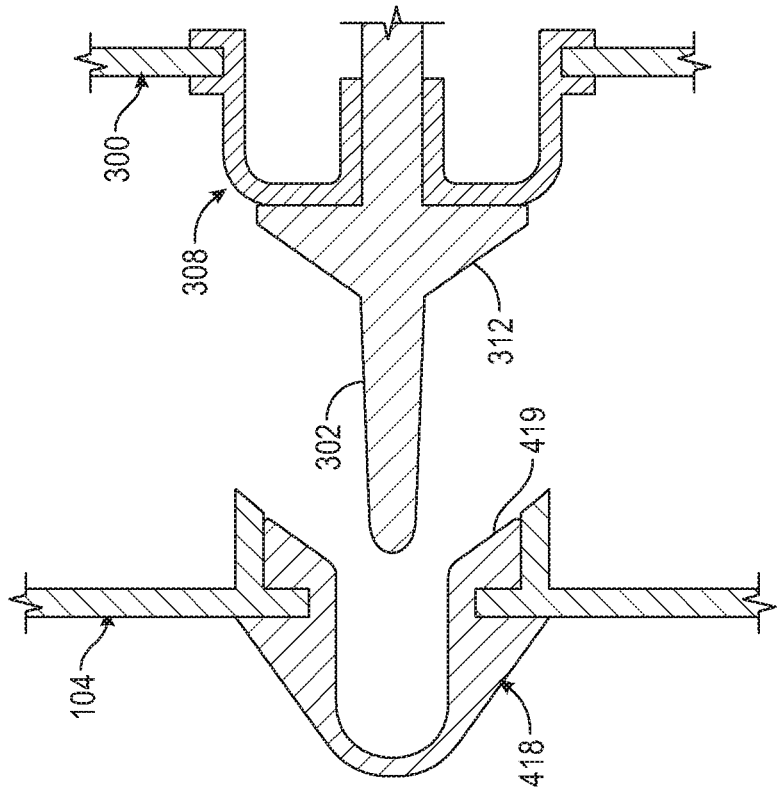
FIG. 7D illustrates another embodiment of a probe being inserted into another embodiment of a seal.
Figure 7C:
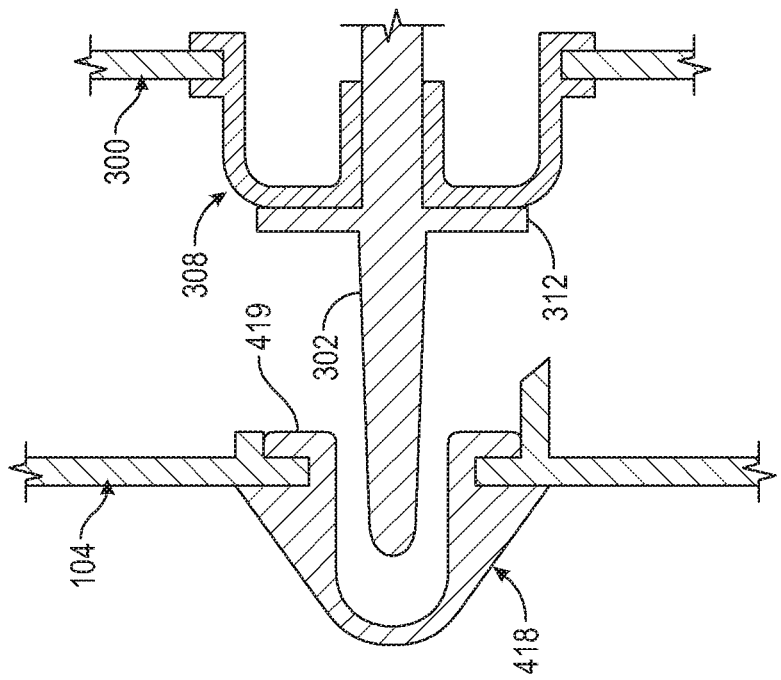
FIG. 7C illustrates the probe of FIG. 7B being inserted into a seal.

With reference to FIG. 7B, which is a section through the probe 302 and the resilient member 308, the probe 302 can include a flange 312. The flange 312 can be a ring, collar, protrusion or the like that extends outward from a main body 313 of the probe 302. As shown in FIG. 7A, each of the probes 302, 304, 306 can include flanges 312, 314, 316, respectively. The flanges 312, 314, 316 allow the probes 302, 304, 306 to be mounted at least substantially flush to the resilient members 308, 310. The flanges 312, 314, 316 can also allow the probes 302, 304, 306 to be at least substantially flush with the seals 418 in the apertures 414a, 414b, 416 when the humidification chamber 104 is installed on the heater base 102. With reference to FIG. 7C, when the probe 302 is inserted into one of the seals 418, the flange 312 can be at least substantially flush with a flat base 419 of the one of the seals 418.

In some embodiments, one or more of the flanges 312, 314, 316 can have a tapered configuration. For example, in the embodiment of FIG. 7D, the flange 312 can have a portion that is tapered toward the end of the probe 302. In other words, the flange surface closest to the one of the seals 418 can be angled away from the post portion of the probe 302. The flange 312 illustrated in the configuration of FIG. 7D comprises a substantially flat base, which can be configured to be at least substantially flush with the resilient member 308. In some configurations, the tapered surface of the flange 312 can be configured to contact a corresponding tapered base 419 of the one of the seals 418 as shown. The tapered surfaces of the flange 312 and the one of the seals 418 can advantageously help center the probe 302 in the one of the seals 418. For example, if the humidification chamber 104 is inserted onto the heater base 102 at an angle or off-center, when the flange 312 contacts the one of the seals 418, the tapered surfaces of the flange 312 can help guide the probe 302 into a more centered alignment within the one of the seals 418.

The resilient member 308 can include a generally hollow main body 309. In the illustrated configuration, the main body 309 comprises a generally tubular configuration in which a portion of the main body 309 is folded back inside of itself. In other words, the main body 309 generally comprises an outer portion 311 and an inner portion 315 that are connected to each other proximate the flange 312 of the main body 313 of the probe 302. The outer portion 311 and the inner portion 315 can be generally tubular and can be integrally formed.

The inner portion 315 contacts the probe 302. In the illustrated configuration, the inner portion 315 grips the main body 313 of the probe 302. In some configurations, the connection between the inner portion 315 and the probe 302 reduces the likelihood of relative axial movement between the two components. In some configurations, the resilient member 308 and the probe 302 can be secured together with any suitable bonding agent or technique.

The outer portion 311 of the main body 309 of the resilient member 308 includes at least one flange 317. In the illustrated configuration, the main body 309 includes a pair of flanges 317. The flanges 317 define a recess 319. A portion of the cartridge 300 can be received within the recess 319. Accordingly, the main body 309 of the resilient member 308 can be secured to the cartridge 300 while another portion of the main body 309 of the resilient member 308 can be secured to the probe 302. The resilient member can accommodate axial movement of the probe 302 relative to the cartridge 300 (e.g., through axial displacement of the inner portion 315 relative to the outer portion 311). The resilient member also can accommodate wobbling movement of the probe 302 relative to the cartridge 300 as well as displacement of the axial center. Thus, the resilient member allows for multi-axial movement of the probe 302 relative to the cartridge 300. This can allow the resilient members 308, 310 and therefore the probes 302, 304, 306 to adjust if the apertures 414a, 414b, 416 in the humidification chamber 104 are not precisely aligned with the probes 302, 304, 306.

The resilient members 308, 310 can be made of silicone or any other suitable material. In some embodiments, the resilient members 308, 310 are stiffer or less resilient than the seals 418. For example, the materials can be selected so that the seals 418 are fully stretched by a force less than the force required to compress the resilient members 308, 310. In other words, the seals 418 can stretch to a full length at forces less than that required to begin to compress or adjust the resilient members 308, 310. This allows the seals 418 to stretch to accommodate the probes 302, 304, 306 before the resilient members 308, 310 compress or adjust. In other words, by allowing the seals 418 to elongate before the resilient members compress, the seals 418 can be stretched during insertion of the probes 302, 304, 306. By allowing the resilient members 308, 310 to compress or flex in any of a number of directions, the probes 302, 304, 306 can be better aligned with the apertures and the grommets and the probes 302, 304, 306 can be more flush following insertion. The resilient members 308, 310 also allow for repeatable insertion depths of the probes 302, 304, 306 in the humidification chamber 104.

Figure 60:
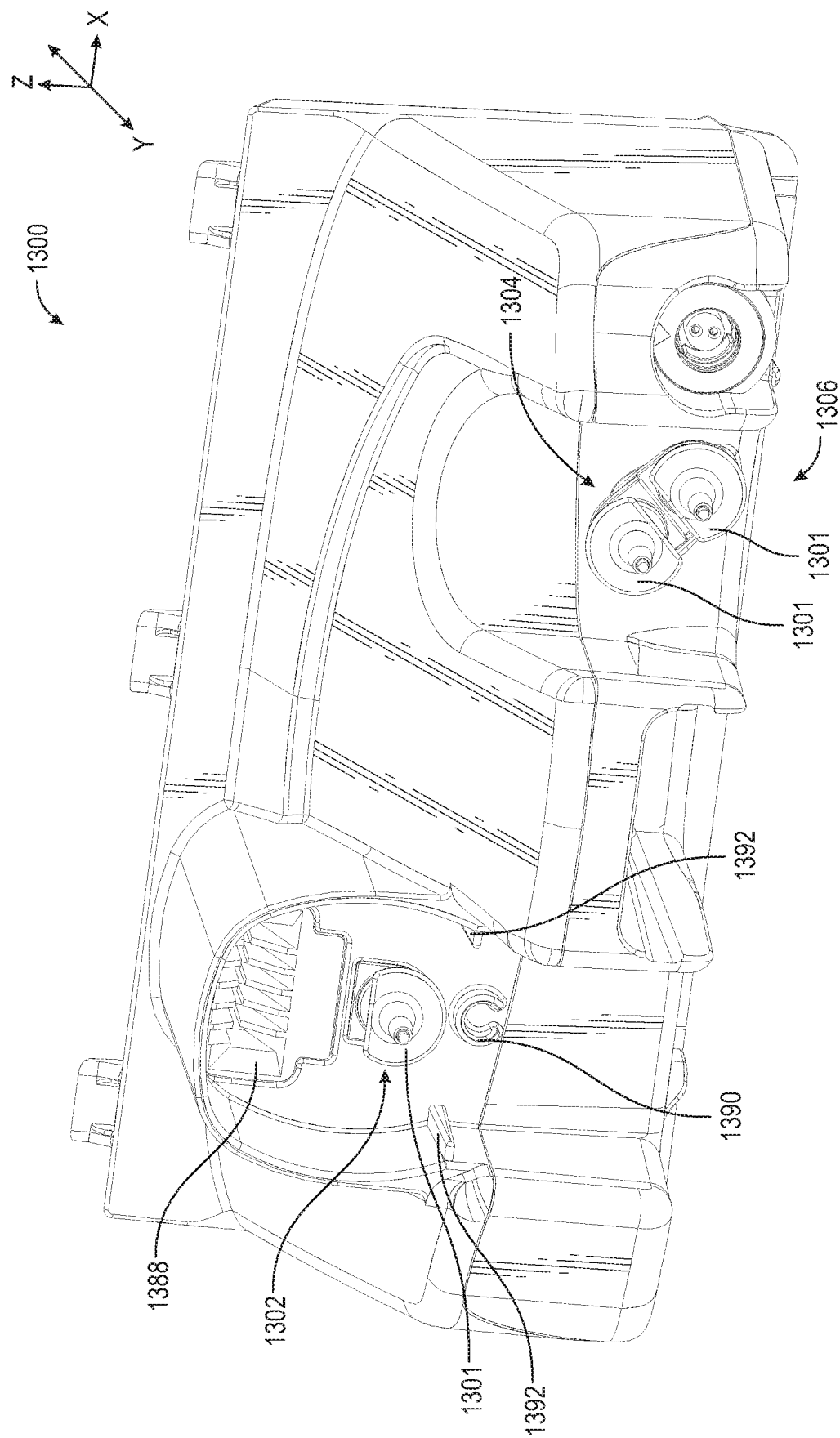
FIG. 60 illustrates an example embodiment of a cartridge.

In some embodiments, for example as shown in FIG. 60, a cartridge 1300 comprises probes 1302, 1304, 1306, where flanges 1301 of the probes 1304, 1306 are generally D-shaped. The D-shape of flanges 1301 can allow the probes 1304, 1306 to be positioned at the desired spacing from one another while providing enough support to the probes 1304, 1306 so that they do not collapse or fold toward one another during engagement of the humidification chamber 1104 with the cartridge 1300.

Figure 61:
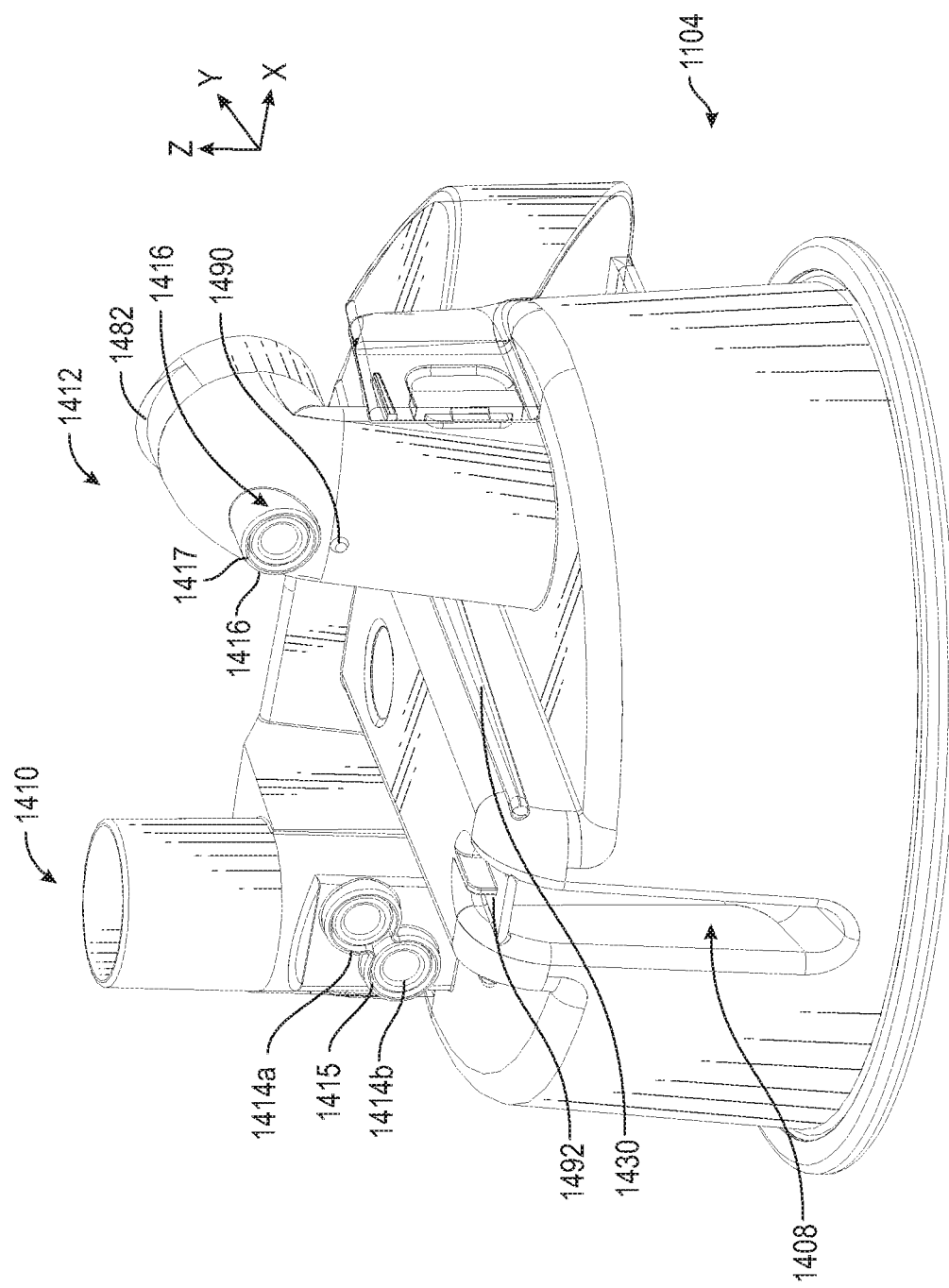
FIGS. 61 and 61B illustrate an example embodiment of a humidification chamber.

For example, in the embodiment of FIG. 7A in which a single resilient member supports both of the probes 304, 306, there is less support provided by the resilient member on the portions of the probes 304, 306 facing each other. However, if the flanges 1301 of the probes 1304, 1306 were full circles, the bases would interfere with one another such that the probes 1304, 1306 would need to be spaced farther apart than desired. As shown in FIGS. 60 and 61, apertures 1414a, 1414b, 1416 in an inlet port 1410 and an outlet port 1412 have encircling ridges 1415, 1417. When the humidification chamber 1104 is installed on the heater base 102 with the cartridge 1300, the flanges 1301 seat against the encircling ridges 1415, 1417. If the surface area of the flanges 1301 able to contact the ridges 1415 is too small, the probes 1304, 1306 may tend to tip toward one another.

Figure 69:
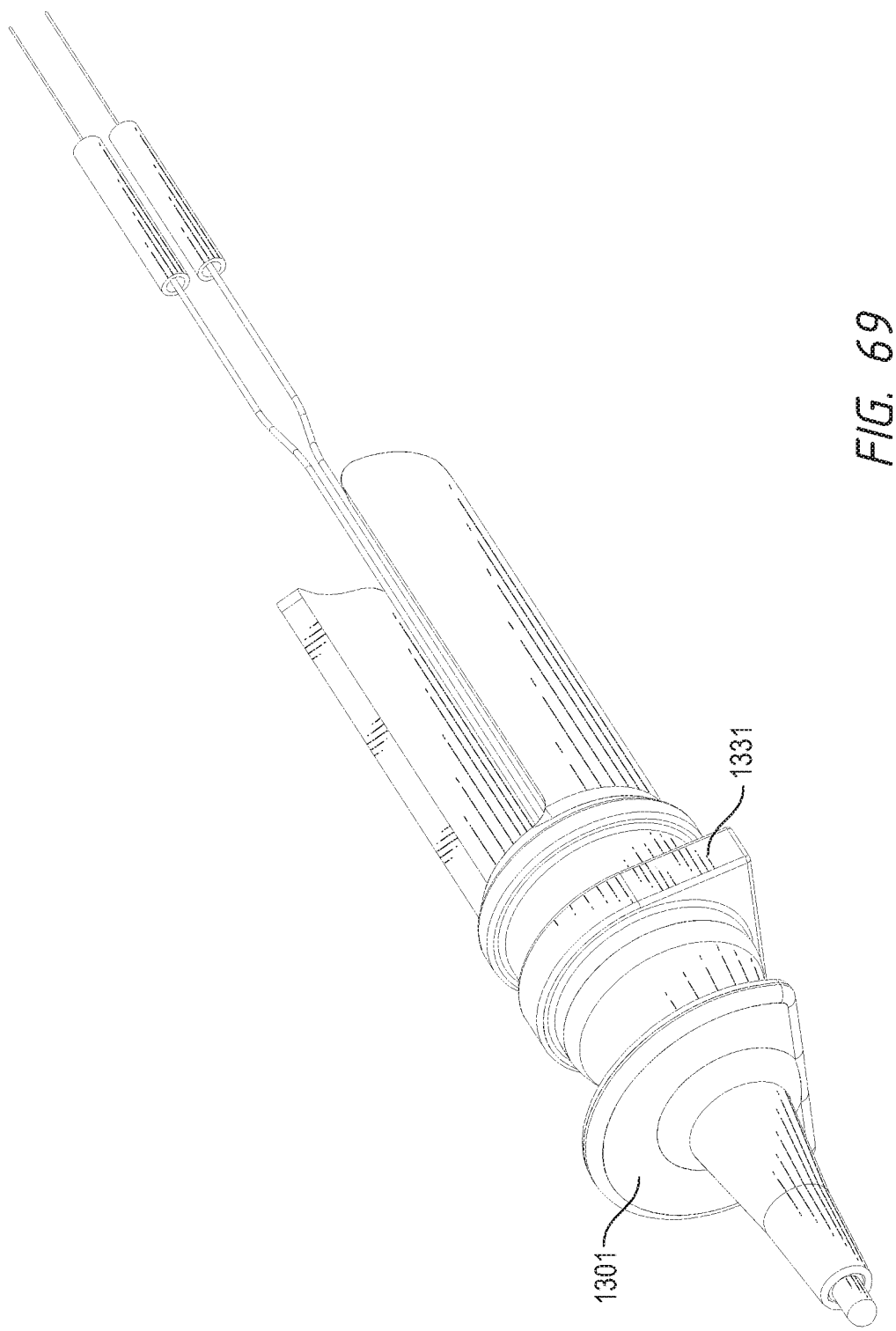
FIG. 69 illustrates an example embodiment of a probe.

As shown in FIG. 69, which illustrates an exemplary probe (which can be any of the probes 1302, 1304, 1306), both the flange 1301 of the probe and the base 1331 of the probe can be generally D-shaped. The D-shaped base 1331 can help reduce or eliminate the likelihood of the probe rotating during installation on the cartridge 1300. In other words, the D-shaped base 1331 can be configured to be received in corresponding D-shaped openings or receptacles in the cartridge 1300, and the D-shape can help ensure the probes 1304, 1306 are properly oriented. In some embodiments, the straight edges of the probe bases 1331 of the probes 1304, 1306 will contact each other (for example, the straight edges can be flush against each other) when the probes 1304, 1306 are installed. The probe 1302 can also have a D-shaped base 1331 configured to be received in a corresponding D-shaped receptacle to ensure the probe 1302 is properly oriented in the cartridge 1300.

Alignment and Engagement Features

The cartridge 300 and at least one portion of the humidification chamber 104 can have a coupling configuration. In some configurations, the cartridge 300 and an upper portion of the humidification chamber 104 can have a coupling configuration. The coupling configuration can promote correct and easy installation of the humidification chamber 104.

As shown in FIGS. 2-6, the cartridge 300 includes outer sidewalls 320. The outer sidewalls 320 extend beyond the tips of the probes 302, 304, 306. The cartridge 300 also includes a central channel 322. In the illustrated configuration, the central channel 322 is defined by fins 324, 326. The fins 324, 326 extend forward from each side of the central channel 322. The fins 324, 326 can extend generally parallel to the sidewalls 320. A recessed portion can be formed between each sidewall 320 and the neighboring fin 324, 326. The probes 302, 304, 306 can be positioned in these recessed portions. In some configurations, at least one of the fins 324, 326 and the sidewall 320 extends further outward from side surfaces 212 of the spine 204 than the distalmost ends of the probes 302, 304, 306. In some configurations, both of the fins 324, 326 and the sidewall 320 adjacent to the probes 302, 304, 306 extend further outward from the side surfaces 212 of the spine 204 than the distalmost ends of the probes 302, 304, 306.

Figure 13:
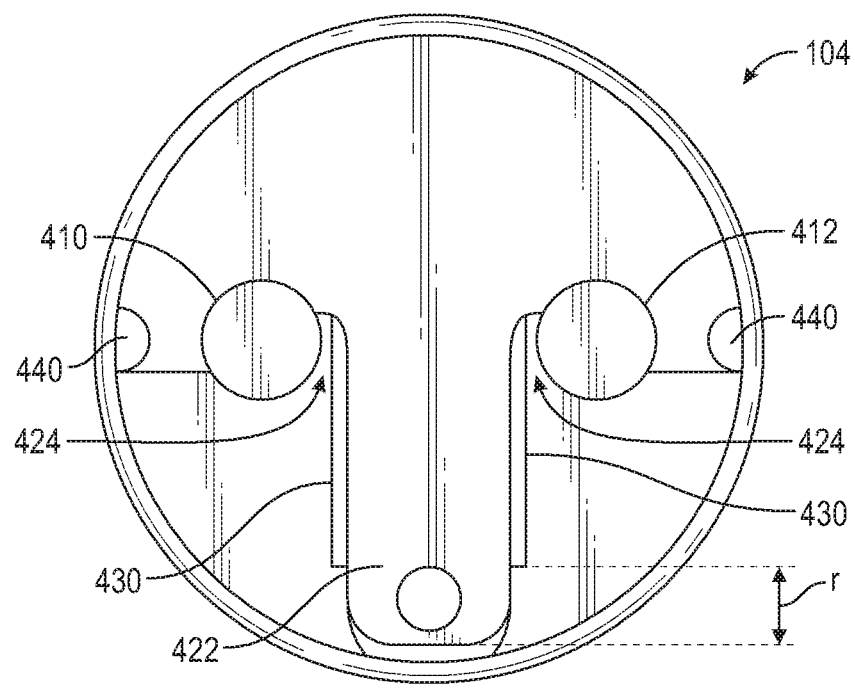
FIG. 13 is a top view of the humidification chamber.
Figure 14:
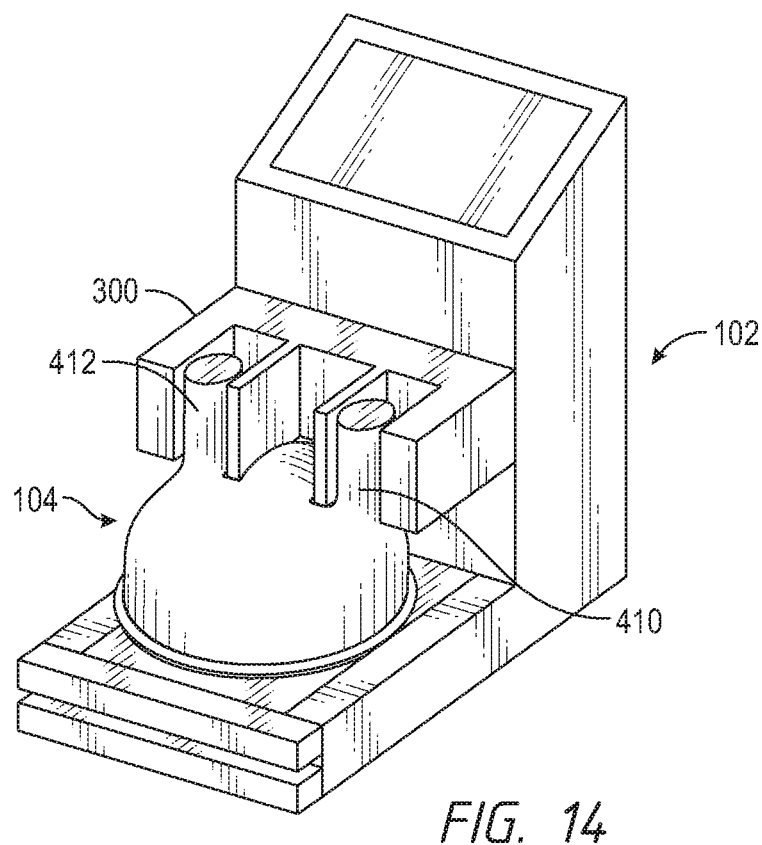
FIGS. 14-17 are views of the humidification chamber installed on the heater base.
Figure 16:
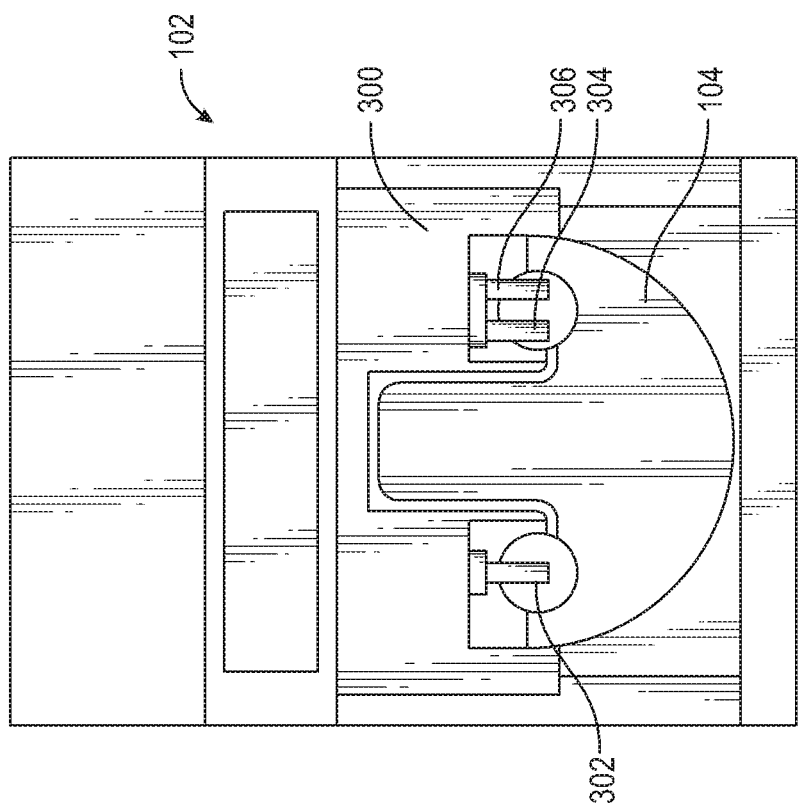

With reference to FIG. 13, the humidification chamber 104 includes a central boss or raised portion 422. In the illustrated embodiment, the humidification chamber 104 includes a groove 424 located between the raised portion 420 and the outlet port 412 and a groove 426 located between the raised portion 420 and the inlet port 410.

The central channel 322 of the cartridge 300 is configured to receive the raised portion 422 of the humidification chamber 104. The fins 324, 326 are configured to slide into the grooves 424, 426 of the humidification chamber 104.

The sidewalls 320 and the fins 324, 326 act as lead-in features to help guide the user in correct installation of the humidification chamber 104 on the heater base 102. The sidewalls 320 and fins 324, 326 also help protect the sensors from damage that could be caused by improper contact with the humidification chamber 104. For example, if the user attempts to install the humidification chamber 104 with the front or a side of the humidification chamber 104 facing the cartridge 300 so that the apertures 414a, 414b, 416 in the inlet port 410 and the outlet port 412 are not aligned with the probes 302, 304, 306, the sidewalls 320 and fins 324, 326 will contact surfaces of the humidification chamber 104 to help reduce the likelihood of contact between the sensors and relatively hard surfaces of the humidification chamber 104.

Figure 8:
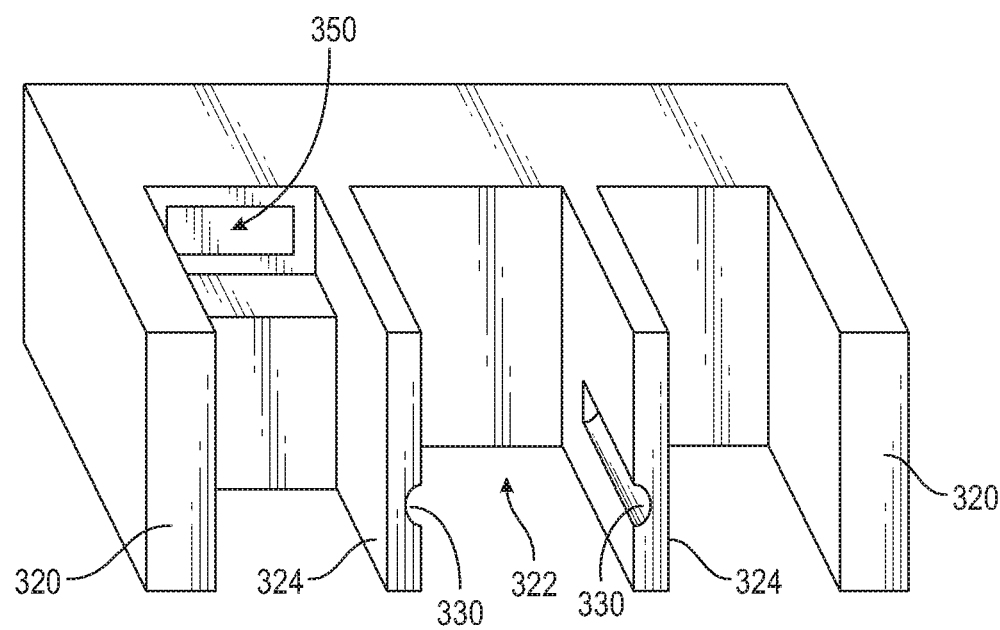
FIGS. 8-9 illustrate another embodiment of a cartridge.

The fins 324, 326 and the humidification chamber 104 can also include features to help stabilize the humidification chamber 104 relative to the cartridge 300 and inhibit rotation, tilting, and/or yaw of the humidification chamber 104. For example, as shown in FIG. 8, inner surfaces of the fins 324, 326 can include generally horizontal grooves 330 extending from front edges of the fins 324, 326 toward the back of the cartridge 300. The grooves 330 can be configured to receive corresponding rails 430 extending along the sides of the raised portion 422 of the humidification chamber 104, as shown in FIG. 13. In some configurations, the grooves can be formed on the cartridge and the rails can be formed on the chamber. In either configuration, when the humidification chamber 104 is installed on the heater base 102 and coupled to the cartridge 300, the rails 430 sit in the grooves 330. The coupling configuration of the rails 430 in the grooves 330 can help inhibit the humidification chamber 104 from excessive tilting. In the illustrated configuration, the grooves 330 can be defined by protruding ridges that taper in a direction extending away from the base and toward the end of the fins 324, 326.

Figure 9:
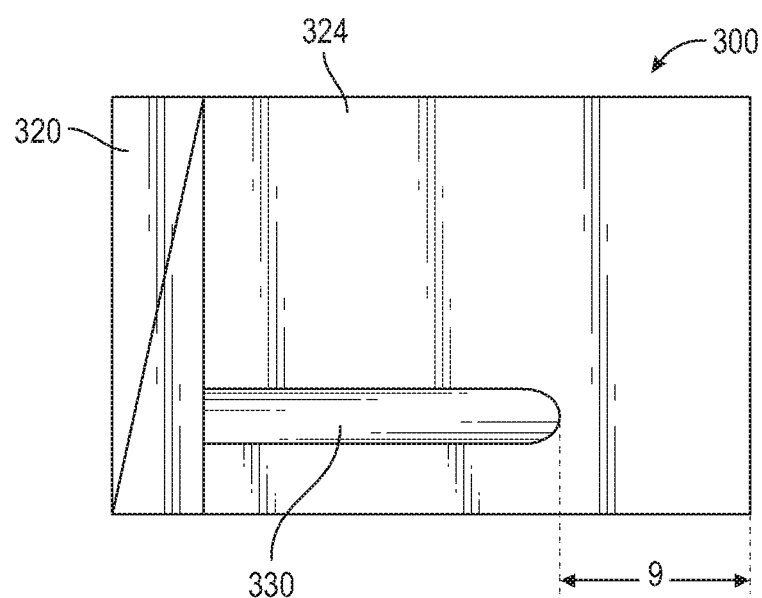
Figure 9B:
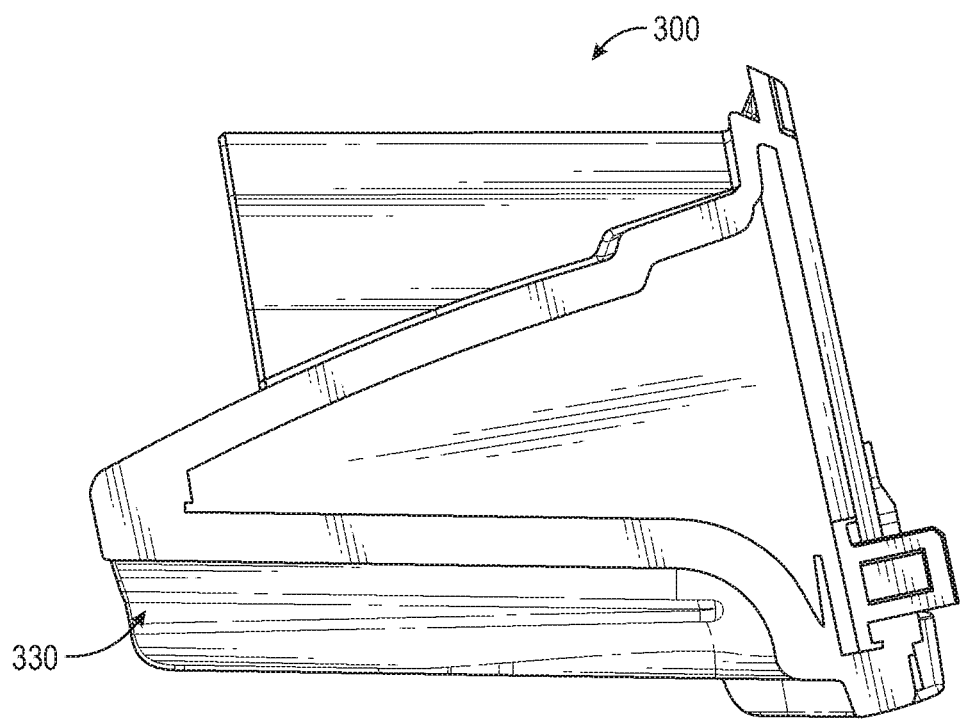
FIG. 9B is a section view of another embodiment of a cartridge.
Figure 10:
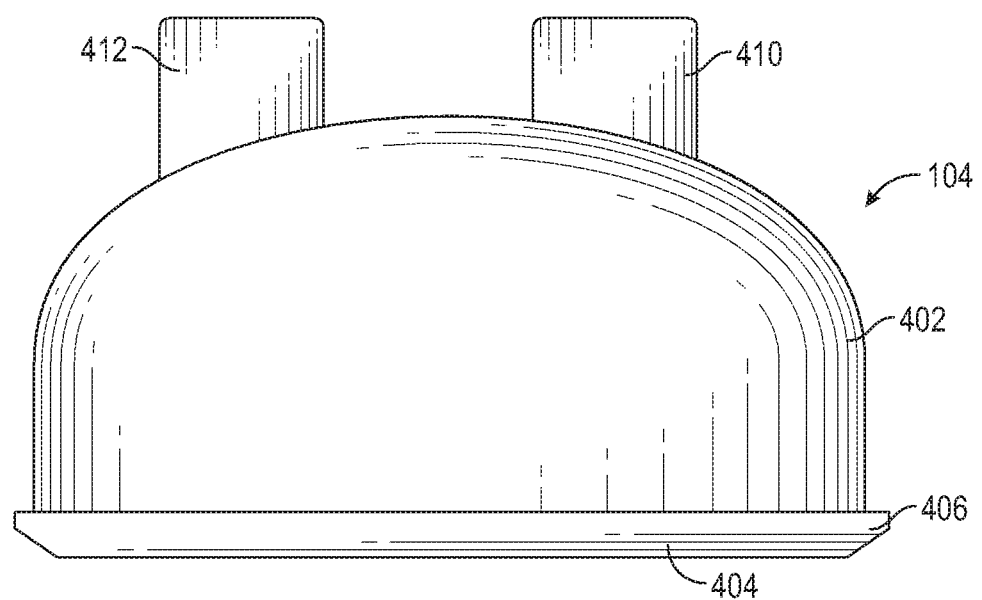
FIG. 10 is a front view of a humidification chamber.
Figure 11:
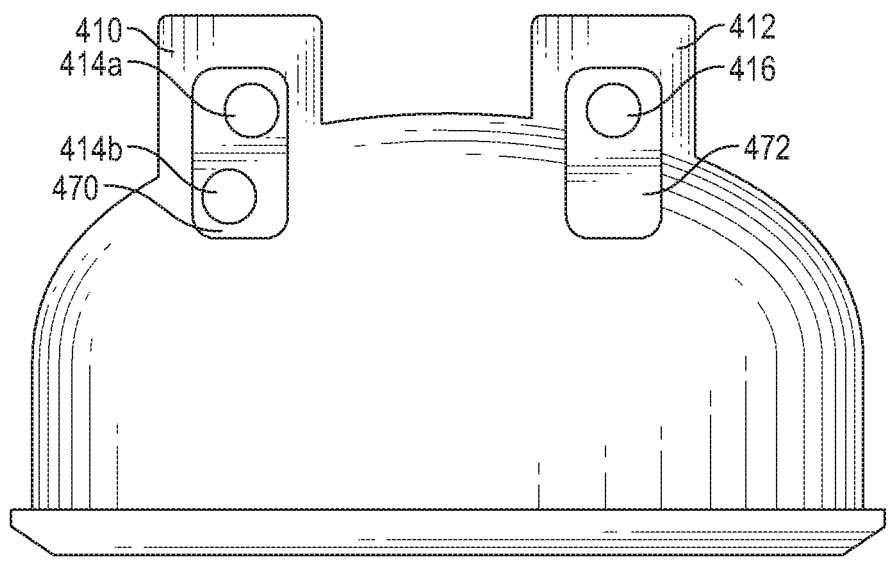
FIGS. 11 and 12 are rear views of the humidification chamber.

As shown in the section view of FIG. 9, in some embodiments, the grooves 330 end at a distance g from the back of the central channel 322. As shown in FIG. 13, in some embodiments, the rails 430 extend from a base of the raised portion toward the back of the humidification chamber 104 and end at a distance r from the back end of the raised portion 422. When the humidification chamber 104 is correctly and fully installed on the heater base 102, the back ends of the rails 430 abut the back end of the grooves 330. This can give the operator a signal that the humidification chamber 104 is fully installed and help inhibit the humidification chamber 104 from being advanced too far. In some embodiments, for example as shown in FIG. 9B, the grooves 330 taper from front to back to allow for easier insertion of the humidification chamber 104 on the heater base 102 and cartridge 300. Moreover, the tapering allows for the grooves 330 and the rails 430 to urge the humidification chamber 104 into a desired position relative to the cartridge 300 and the heater base 102. As shown in the embodiment of FIG. 61, rails 1430 are correspondingly tapered to engage tapered grooves 1330.

In some embodiments, the cartridge 300 includes clips 340 configured to engage and secure the humidification chamber 104. As shown in FIGS. 2-5, the clips 340 can be located on inner surfaces 328 of the sidewalls 320. The body 402 of the humidification chamber 104 can include corresponding recesses 440 as shown in FIG. 13. The recesses 440 can be configured to receive the clips 340 when the humidification chamber 104 is installed on the heater base 102. The engagement of the clips 340 with the recesses 440 can provide a positive engagement feel to the operator to indicate to the operator that the humidification chamber 104 is fully installed on the heater base 102. The clip 340 and recesses 440 can also help promote proper installation of the humidification chamber 104 so that the probes 302, 304, 306 are properly inserted in the inlet port 410 and the outlet port 412.

Figure 4A:
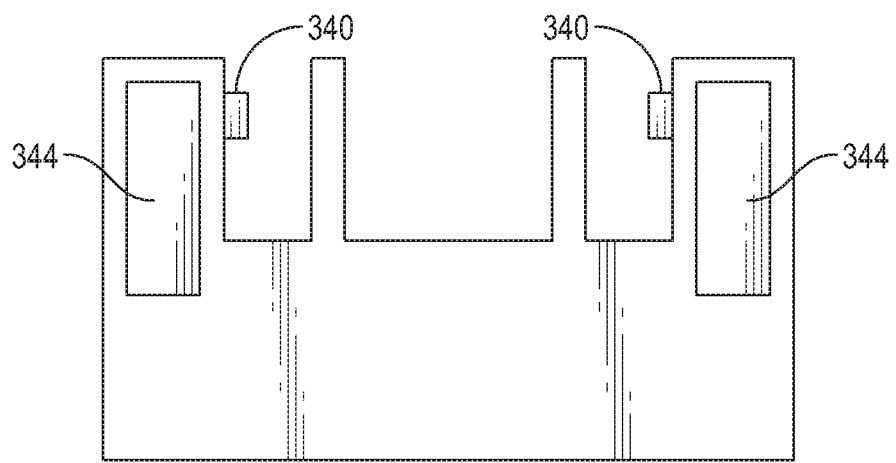
Figure 4B:
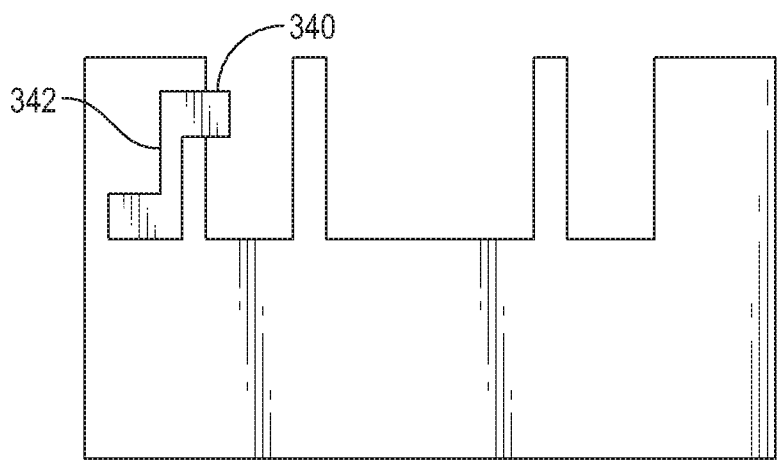

In some embodiments, the sidewalls 320 can allow for some degree of flexion. For example, the sidewalls 320 can flex outward as the humidification chamber 104 is being inserted and the clips 340 slide along outer walls of the humidification chamber 104. The sidewalls 320 then revert back to a relaxed state when the clips 340 are received in the recess 440. In some configurations, the clips 340 simply deflect relative to the sidewalls 320. In other words, the clips 340 can be configured on cantilevered members 342 as shown in FIG. 4B. The clips 340 can be coupled to or integrally formed with the cantilevered members 342. The cantilevered members 342 deflect outward as the humidification chamber 104 passes between the clips 340 until the clips 340 locate within the recesses 440 of the humidification chamber 104. The cantilevered members 342 can be covered by lids 344 as shown in FIG. 4A.

Conduit to Humidification Chamber and Cartridge Connection

Figure 20:
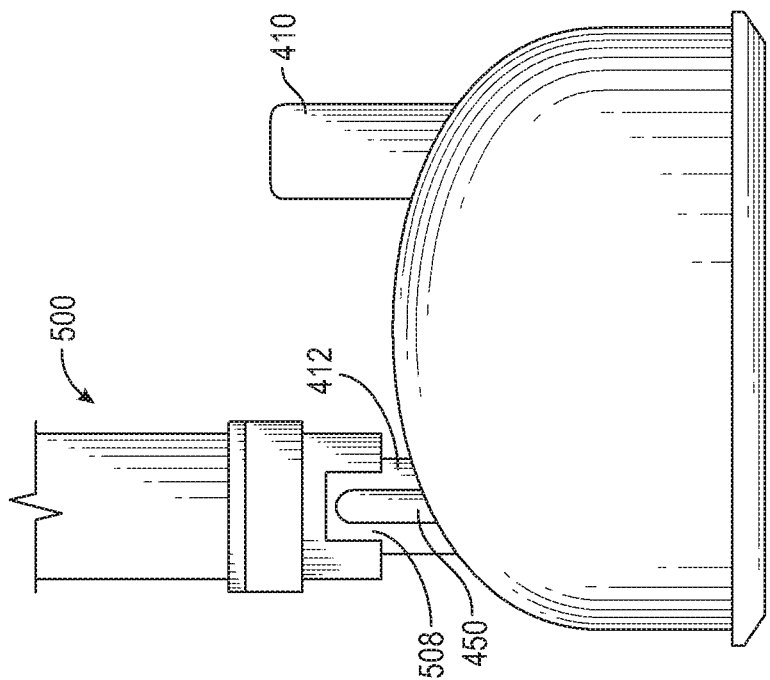
Figure 19:
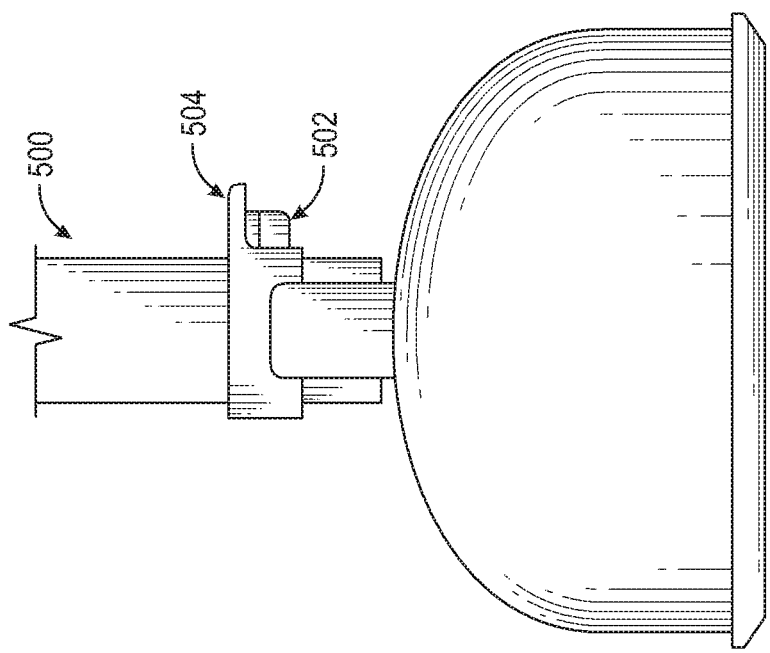

In some configurations, a conduit connector 500 is coupled to the chamber end of the inspiratory conduit 120 as shown in FIGS. 18-20. The conduit connector 500 is configured to couple the inspiratory conduit 120 to the humidification chamber 104 and the cartridge 300. In some configurations, the conduit connector 500 provides an electrical connection between the inspiratory conduit 120 and the cartridge 300. Preferably, the conduit connector 500 provides both a pneumatic seal between the inspiratory conduit 120 and the humidification chamber 104 and an electrical connection between the inspiratory conduit 120 and the cartridge 300. More preferably, the conduit connector 500 facilitates the making of both the pneumatic seal with the humidification chamber 104 and the electrical connection with the cartridge 300 with a single direction of movement. In some configurations, the conduit connector 500 is coupled to the chamber end of the supply conduit 132 and is configured to make similar pneumatic and electrical connections between the supply conduit 132 and the humidification chamber 104 and the cartridge 300.

In some configurations, the conduit connector 500 includes a PCB located on or coupled to a PCB connector 502. The PCB can be connected to heater wires of the conduit and/or to sensor wires of the inspiratory conduit 120. In some configurations, the PCB can be connected to heater wires and sensor wires. Thus, the conduit connector 500 includes electrical components that can be used to facilitate an electrical connection between heater wires, sensor wires or the like with the electronics of other portions of the humidification system 100.

In the illustrated configuration, the conduit connector 500 includes an electrical connector 502. The electrical connector 502 is joined to the PCB of the conduit connector 500 and is configured to connect with a mating connector of another component of the humidification system 100. In some configurations, the electrical connector 502 is configured to be received in or placed in electrical contact with a corresponding electrical connector that is joined to the heater base 102. For example, when the conduit connector 500 is coupled to the humidification chamber 104 and the humidification chamber 104 is installed on the heater base 102, the electrical connector 502 can mate with an electrical connector that is joined to the heater base 102. In one configuration, the electrical connector 502 can be configured to be received in a receiver or mating electrical connector 350 that is disposed on the cartridge 300, as shown in FIGS. 7-8. In another configuration, the conduit connector 500 can be configured to be engaged with the cartridge 300 so as to place the electrical connector 502 in electrical contact with the electrical connector 350. In the illustrated embodiment, the conduit connector 500 can include a hood 504 extending from the conduit connector 500 to cover the electrical connector 502. The hood 504 can help protect the electrical connector 502 from condensate that might drip onto the conduit connector 500 from the inspiratory conduit 120, for example but without limitation.

As shown in FIGS. 18-20, the electrical connector 502 can be located on the same side of the conduit connector 500 as a keyhole 506. This arrangement allows the electrical connector 502 to be coupled to the mating electrical connector 350 simultaneously with the conduit connector 500 coupling to the outlet port 412 and the keyhole 506 coupling around the probe. In some configurations, the outlet port 412 can include a feature, such as a collar or the like, with which the keyhole 506 is designed to mate. In other words, instead of the keyhole 506 coupling around the probe, the keyhole 506 simply surrounds the probe while coupling to a feature on the outlet port 412.

In the configuration illustrated in FIG. 18, the electrical connection 502 of the conduit connector 500 has dual insertion axes. In other words, the electrical connector 502 can be inserted into the mating electrical connector 350 along both a horizontal axis and a vertical axis. By providing dual insertion axes, the conduit connector 500 can be coupled first to the outlet port 412 and then the humidification chamber 104 can be slid onto the heater base 102 so that the connector is inserted horizontally into the mating electrical connector 350 or, alternatively, the humidification chamber 104 can first be inserted into the heater base 102 and then the conduit connector 500 can be coupled to the outlet port 412 so that the connector 502 is inserted vertically into the mating electrical connector 350.

Keyhole

In some configurations, the conduit connector 500 includes the keyhole 506 located beneath the electrical connector 502. The keyhole 506 can be a cutout that extends into the conduit connector 500 from the extreme end that is configured to be placed over the outlet port 412. When the conduit connector 500 is coupled to the humidification chamber 104 installed on the heater base 102 with the cartridge 300, the keyhole 506 allows the conduit connector 500 to accommodate and fit around the probe 302 extending into the aperture 416. In other words, the keyhole provides a sufficient axial length to a cuff portion 503 of the conduit connector 500 to provide a stable connection between the conduit connector 500 and the outlet port 412 while also allowing the probe 302 to be positioned closer to the end of the outlet port 412 such that the distance between the probe 302 and the end of the outlet port 412 can be reduced, which improves the accuracy of the sensor output because the probe 302 will be disposed as close as possible to the end of the unheated outlet port 412 and as close as possible to the start of the heated inspiratory conduit 120.

In some configurations, the keyhole 506 also can provide a snap fit between the conduit connector 500 and the outlet port 412. The snap fit can help indicate when the conduit connector 500 is completely and correctly coupled to the outlet port 412. The snap fit can also provide a retention force sufficient to resist decoupling as a result of an increase in air pressure if the conduit becomes blocked downstream of the conduit connector 500.

In some configurations, the keyhole 506 can provide a retention force in the range of about 12 N (Newtons) to about 45 N. A neck 510 can be defined as a portion of the keyhole 506 that is narrower than a diameter of the opening that receives the aperture of the outlet port 412. A width of the neck 510 can influence the retention force provided.

The retention force provided can help maintain the electrical connection between the electrical connector 502 of the conduit connector 500 and the mating electrical connector 350 (see FIG. 7A) on the cartridge 300. In some embodiments, the center of the keyhole body and the electrical connector 502 are spaced apart by a vertical distance c, shown in FIG. 18.

Back Slit

In some configurations, one or both of the inlet port 410 and the outlet port 412 can include at least one feature to help a user distinguish the ports. In some configurations, one or both of the inlet port 410 and the outlet port 412 can include features to allow for connection of a connector coupled to the supply conduit 132 and/or the inspiratory conduit 120. For example, as shown in FIG. 20, the front of the outlet port 412 can include a rib 450. The rib 450 in the illustrated configuration can be diametrically opposed to the aperture on the outlet port 412. Other positions also can be used.

In the illustrated configuration, the conduit connector 500 can include a recess or a slit 508 opposite the keyhole 504. The recess accommodates and fits around the rib 450 on the outlet port 412. The rib 450 can advantageously help inhibit a user from attaching a conduit other than the inspiratory conduit 120 with the conduit connector 500 to the outlet port 412. This can help reduce potential risks to the patient that could result from use of an improper conduit. The recess 508 can also allow the conduit connector 500 to more easily flex as the keyhole 506 flexes to accommodate the probe 302. Furthermore, the recess 508 and the rib 450 can encourage proper rotational alignment of the conduit relative to the port.

Consumable Identification

Various types and configurations of conduits are available and can be used with a humidification system as described herein. In some applications, different conduits can be designed or suitable for different patients, types of therapy, and/or therapy parameters. In some embodiments, the heater base 102 or the cartridge 300 can be capable of detecting the type of the inspiratory conduit 120 coupled to the system. Based upon the detection of the type of the inspiratory conduit 120, the heater base 102 and/or the cartridge 300 can automatically select certain operational, control, and/or therapy parameters based upon the identified conduit. For example, various types of the inspiratory conduit 120, e.g., universal, single limb, infant, or adult, can include unique identification components, such as resistors, dual function components such as heater wires that have identifiable resistance values, RFID components, and/or memory chips such as EEPROMs. The identification components can be identified by various measurement means.

When the inspiratory conduit 120 is coupled to the humidification chamber 104 installed on the heater base 102, one or more processors 114 or other suitable electrical component(s) in the heater base 102 and/or the cartridge 300 can measure the resistance of the resistor associated with the conduit. The processor 114 then can compare the measured resistance to a table or the like stored in memory 112 or another suitable component in the heater base 102 and/or the cartridge 300 and select the operational, control, and/or therapy parameters associated with the measured resistance value. The operational, control, and/or therapy parameters then can be set according to the values stored in memory 112. Other identification mechanisms are also possible as discussed above. In some embodiments, the cartridge 300 identifies the conduit attached and sends the identification information and/or operational, control, and/or therapy parameters to the processor 114.

In some embodiments, the identification resistor or other mechanism can be located on or positioned within the conduit connector 500. In some embodiments, as discussed above, the conduit connector 500 includes connections for heating element(s) in the inspiratory conduit 120 and provides power for the heating element(s) when the conduit connector 500 is coupled to the heater base 102. In some such embodiments, the conduit identification resistors are selected to have resistances in a particular range, for example, hundreds of kΩ, so as to not interfere or be confused with the heater wire, which may have a resistance in the range of, for example, tens of Ω. In other words, in some configurations, the conduit includes heating wires and an identification resistor. In some embodiments, the heater wire has a resistance in the range of about 1Ω to about 200Ω. In some such embodiments, the identification resistors can have resistances in the range of about 200Ω to about 200Ω.

Alternative Inspiratory Conduit Connectors

FIGS. 21-24 illustrate alternative embodiments of inspiratory conduit chamber end connectors. As with the connector described above, the connectors described herein can provide both a pneumatic connection to the humidification chamber 104 and an electrical connection to the cartridge 300. Thus, the connectors provide two different types of connections to two separate components. In some configurations, the connector also can provide a physical connection to both the humidification chamber 104 and the cartridge 300.

As shown in FIG. 21, in some configurations, the outlet port 412 of the humidification chamber 104 can include an elbow connector 460. In some embodiments, the elbow connector 460 is integrally formed with the humidification chamber 104. For example, the elbow connector 460 can form at least a portion of the outlet port 412. In other embodiments, the elbow connector 460 is coupled to the outlet port 412, for example, with epoxy resin, ultrasonic welding, or other appropriate means. In other embodiments, the elbow connector 460 is configured to be removably coupled with the outlet port 412. In some configurations, the elbow connector 460 angles toward the front of the humidification chamber 104. In other words, the elbow connector 460 angles away from the heater base 102 when the humidification chamber 104 is installed on the heater base 102. In the illustrated embodiment, the elbow connector 460 bends to an angle of about 90°. The portion of the elbow connector 460 extending away from the heater base 102 is configured to receive the inspiratory conduit 120 with the conduit connector 500 along an axis generally parallel to an installation axis of the humidification chamber 104 on the heater base 102. Thus, in some configurations, the elbow connector 460 extends in a direction generally parallel to a direction of insertion of the humidification chamber 104 onto the heater base 102. In some configurations, the humidification chamber 104 includes features (e.g., the axis of the aperture 416, or the rails 430) that are related to the direction of insertion of the humidification chamber 104 onto the heater base 102 and the elbow connector 460 can be directionally related to such features such that, upon insertion of the humidification chamber 104 onto the heater base 102, the elbow connector 460 is orientated generally parallel to the direction of insertion. The term "generally parallel" is intended to imply parallel with some variation so long as the variation does not render connection as described above to be difficult or impossible. Other angles and orientations for the elbow connector 460 are also possible. The inlet port 410 may or may not include an elbow connector.

With reference to FIG. 21, the conduit connector 500 includes an electrical connector 512. In the illustrated embodiment, the conduit connector 500 includes a USB style connector 512. In other embodiments, the conduit connector 500 can include a blade style connector or any other suitable style connector. The USB connector 512 or other electrical connector can be configured to be received in a corresponding receptacle on the cartridge 300.

In some embodiments, the USB connector 512 extends from a periphery or side of the conduit connector 500. In other words, the USB connector 512 can be laterally spaced from a central axis of the inspiratory conduit 120 extending into the conduit connector 500. As shown, the USB connector 512 extends from the conduit connector 500 along an axis parallel to but offset laterally from a lumen defined within the inspiratory conduit 120. In some configurations, the USB connector 512 has a generally bisecting plane that extends through the central axis of the portion of the conduit connector 500 that joins to the conduit. The USB connector 512 and the portion of the conduit connector 500 that joins to the inspiratory conduit 120 also extend along axes parallel to the probe 302 extending into the outlet port 412.

In the illustrated embodiment, the USB connector 512 extends beyond the end of the conduit connector 500. In other embodiments, the USB connector 512 can be set back from the end of the conduit connector 500 so that the end of the conduit connector 500 extends beyond the USB connector 512. The conduit connector 500 can be configured so that the pneumatic connection of the inspiratory conduit 120 to the elbow connector 460 via the conduit connector 500 is made before the electrical connection of the USB connector 512 to the cartridge 300. Such a configuration results in a single axis connection between the electrical connector 512 and the cartridge 300.

In some embodiments, the conduit connector 500 and/or the elbow connector 460 can include mating features, including any of those described above. The mating features can help promote correct alignment of the conduit connector 500 to the elbow connector 460 so that the USB connector 512 is properly aligned with the corresponding receptacle on the cartridge 300 to ensure the electrical connection is made. In addition, one or more configurations, a locking coupling can be provided to secure the conduit connector 500 to the elbow connector 460.

In some configurations, for example as shown in FIG. 22, the inspiratory conduit 120 can be permanently attached directly to the elbow connector 460 of the humidification chamber 104. In the illustrated embodiment, the electrical connector 512 extends from the elbow connector 460. The electrical connector 512 can extend from the back or a side of the elbow connector 460. The electrical connector 512 and the corresponding receptacle on the cartridge 300 can be configured so that the electrical connection is made when the humidification chamber 104 is installed on the heater base 102. This configuration allows for fewer setup steps because the inspiratory conduit 120 does not need to be separate coupled to the humidification chamber 104 before or after the humidification chamber 104 is installed on the heater base 102.

In the embodiment illustrated in FIG. 23, the elbow connector 460 can be coupled to the inspiratory conduit 120. The inspiratory conduit 120 with the elbow connector 460 can be configured to be coupled to the humidification chamber 104 before the humidification chamber 104 is installed on the heater base 102. The USB connector 512 can be received in the corresponding receptacle on the cartridge 300 and the electrical connection can be made when the humidification chamber 104 is installed on the heater base 102. Once the humidification chamber 104 is installed on the heater base 102, this configuration inhibits or prevents the inspiratory conduit 120 from being removed from the humidification chamber 104 without the humidification chamber 104 being removed from the heater base 102.

Figure 24:
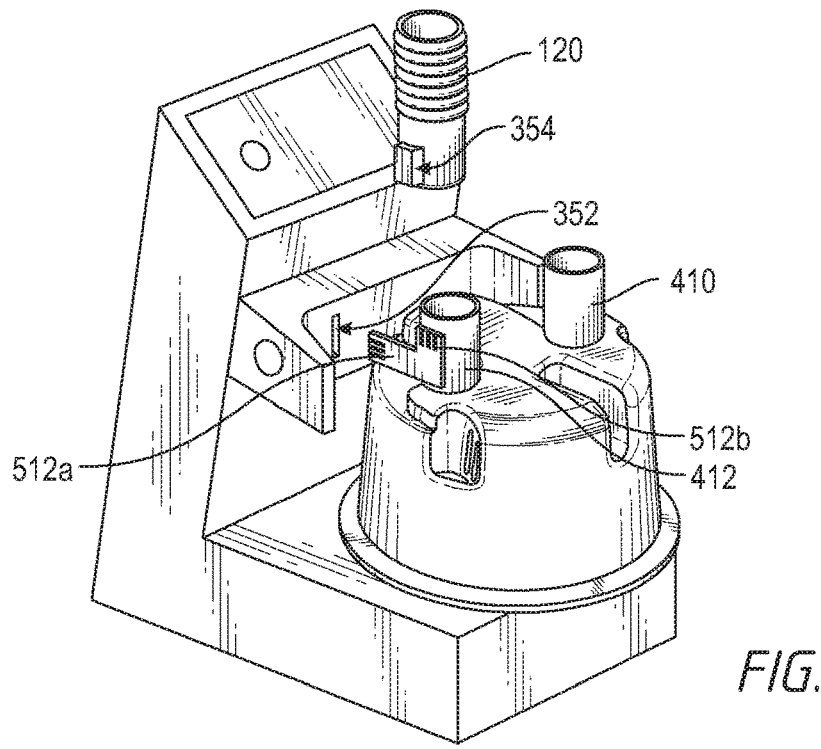

With reference to FIG. 24, in some configurations, the outlet port 412 of the humidification chamber 104 includes two plugs 512a, 512b. The plugs 512a, 512b can be USB connectors, blade connectors, or any other suitable connectors. The plug 512a can be oriented generally horizontally and can be configured to be received in a corresponding receptacle on the cartridge 300, for example, receptacle 352 shown in FIG. 24, when the humidification chamber 104 is installed on the heater base 102. The plug 512a extends along an axis generally parallel to an insertion axis of the humidification chamber 104 on the heater base 102. The plug 512b can be oriented generally vertically and can be configured to be received in a corresponding receptacle 354 on the inspiratory conduit 120 when the inspiratory conduit 120 is physically and pneumatically connected to the humidification chamber 104. In some configurations, the plugs 512a, 512b can be a single, integrally formed component as shown in FIG. 24. In some configurations, the plugs 512a, 512b can be separate components that can be coupled to the outlet port 412.

Figure 25:
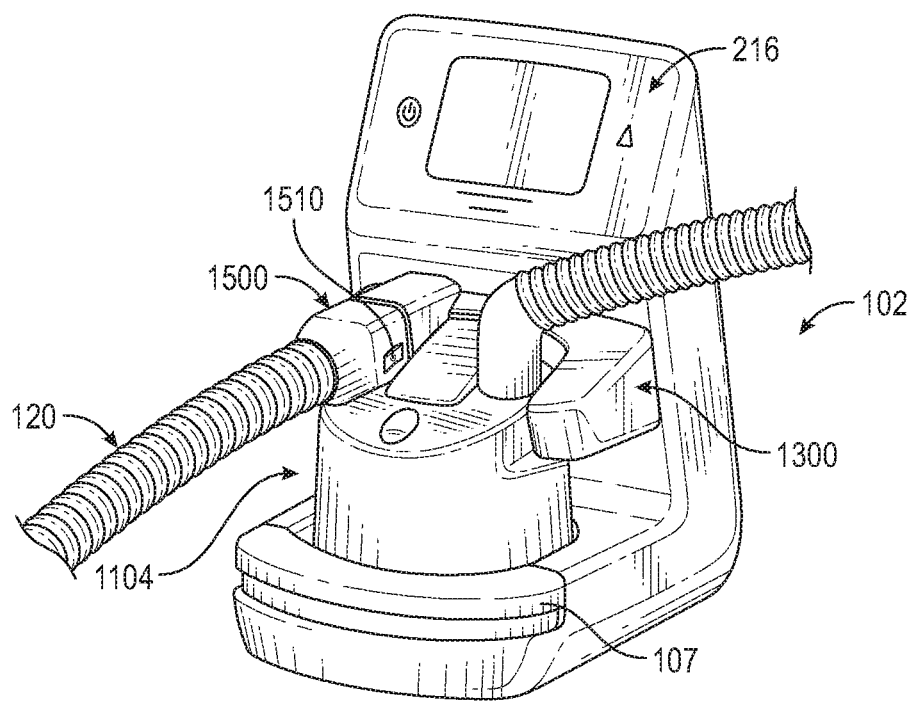
FIGS. 25-26 illustrate an example embodiment of a conduit connector coupled to a humidification chamber and heater base.
Figure 26:
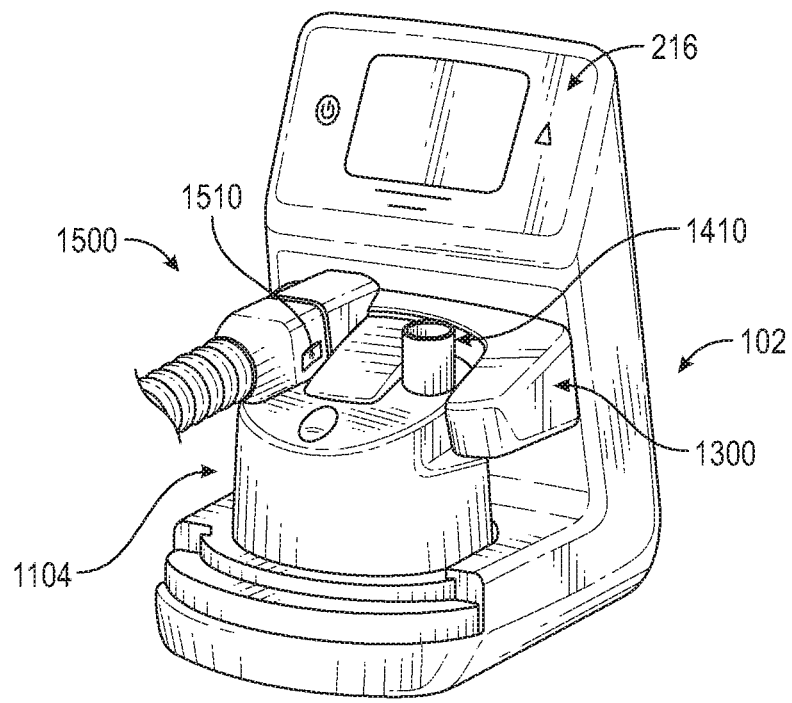
Figure 27:
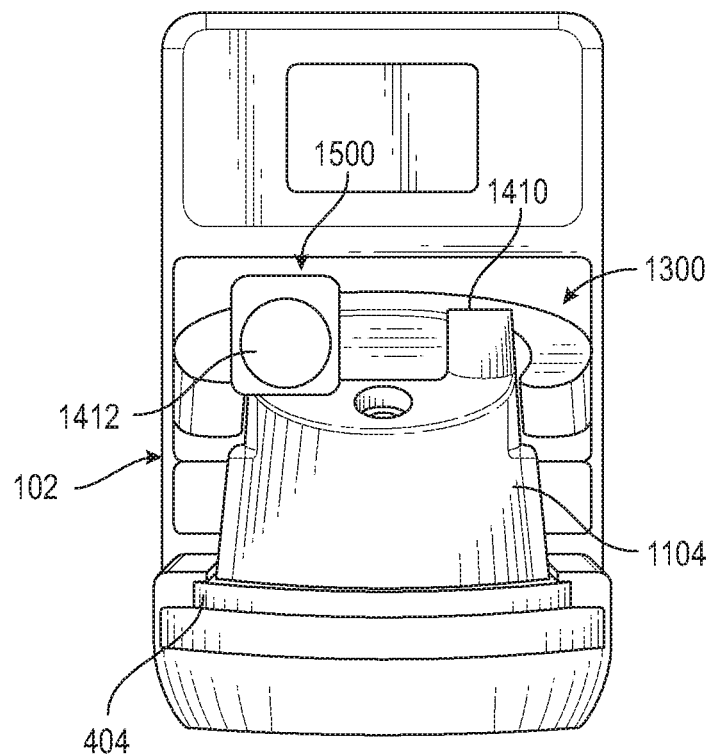
FIG. 27 illustrates the humidification chamber coupled to the heater base of FIGS. 25-26.
Figure 28:
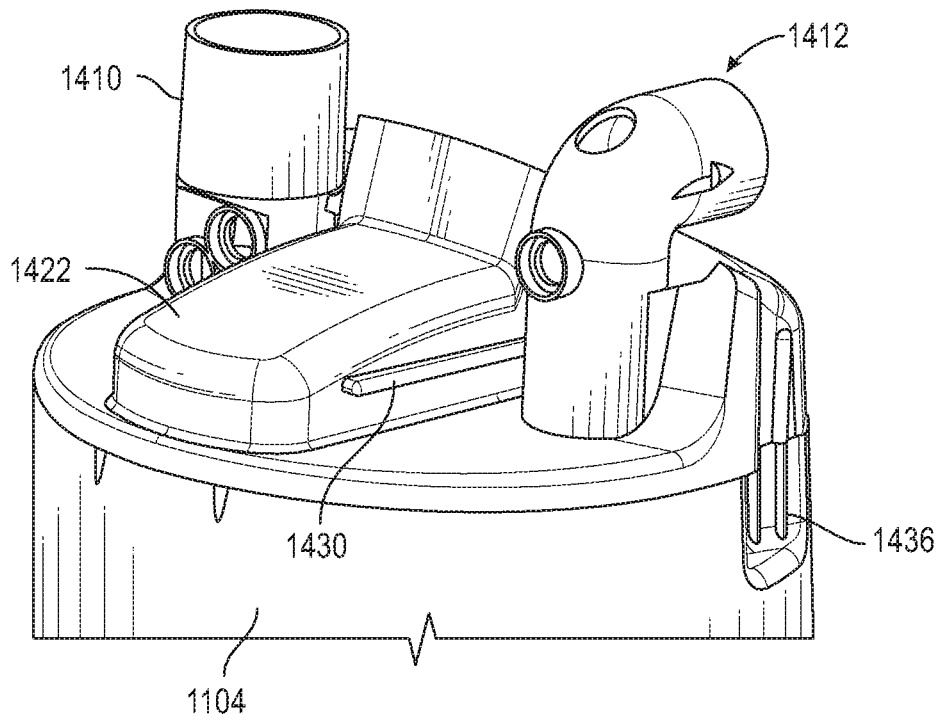
FIGS. 28-34 illustrate various views of the humidification chamber of FIGS. 25-27.
Figure 29:
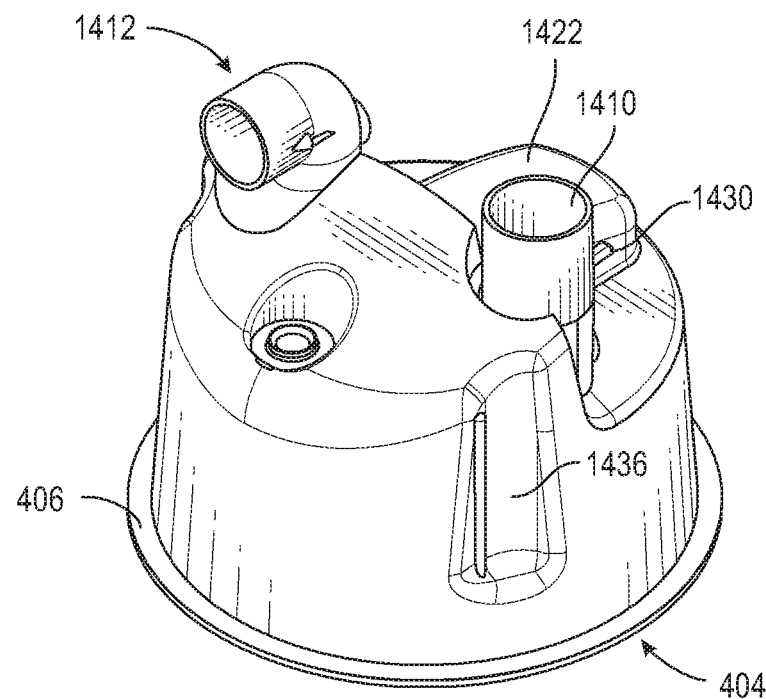

Alternative Horizontal Conduit to Humidification Chamber and Cartridge Connection FIGS. 25-26 illustrate another embodiment of a conduit connector 1500 coupled to the chamber end of the inspiratory conduit 120 and the humidification chamber 1104 and the cartridge 1300. The conduit connector 1500 pneumatically connects the inspiratory conduit 120 to the outlet of the humidification chamber 1104. As shown in FIG. 28, the outlet port 1412 preferably terminates in a substantially horizontal portion that is angled away from the heater base 102 when the humidification chamber 1104 is installed on the heater base 102. The inlet port 1410 of the humidification chamber 1104 is configured to be fluidly connected to a source of pressurised gas. This may be positioned remote from the humidification apparatus or form an integral part thereof, although it may be detachable therefrom. For example, the inlet port 1410 may be pneumatically coupled to a motorised fan in or associated with the heater base 102 that drives gases through the inlet port 1410. In some applications, the humidification system can be used for delivery of gases at relatively high flow rates, for example, up to or greater than about 100 L/min. In some cases, certain features designed to improve humidity delivery at higher flow rates can cause liquid from within the chamber 1104 to splash out through the outlet port 1412. This is not desirable. The angled outlet port 1412 can advantageously help reduce the velocity of gases flowing through the outlet port, which inhibits or reduces the likelihood of liquid splashing out through the outlet port 1412. The angled outlet port 1412 can also help reduce dead space in the outlet port 1412.

The conduit connector 1500 facilitates electrical connection to the heater base 102 via the cartridge 1300. The cartridge 1300 may be integrally formed with the heater base 102 or be a separate, replaceable module or cartridge. The ability to change modules can advantageously be used to enable mating with different models of the humidification chamber 104 and/or conduit connector. Additionally or alternatively, by comprising control circuitry, the module can be changed to alter the operation of the humidification apparatus. The inspiratory conduit 120 can include one or more resistive heating wires that provide for heating of the conduit wall and/or sensor wires that electrically or otherwise facilitate communication of signals relating to one or more parameters of the system. Thus, the term "electrical connection" is used to distinguish from the term "pneumatic connection" and should not be used in a limiting way. For example, light signals via optical fibres may be communicated. Consequently, the conduit connector 1500 may more generally communicatively and/or electrically connect the inspiratory conduit 120 (and any associated peripheral equipment, such as sensors, for example) to the heater base 102, such as via the cartridge 1300.

The conduit connector 1500 may include at least one button or switch 1510, which may be manually depressed to enable the conduit connector 1500 (and the inspiratory conduit 120) to be disconnected from the humidification chamber 1104. As will become apparent herein below, the conduit connector 1500 and the outlet port 1412 of the humidification chamber 1104 preferably become lockably engaged on connection therebetween with the at least one button or switch 1510 being used to subsequently allow for disengaging the conduit connector 1500 from the humidification chamber 1104. Any suitable connection can be used.

As shown in FIGS. 28-34, the configuration of the outlet port 1412 of the humidification chamber 1104 is oriented so as to be substantially parallel to the direction of motion of the humidification chamber 1104 as it is slid on or off of the heater base 102, at least at the end of the outlet port 1412 distal from the humidification chamber 1104. By configuring the apparatus in this way, it is then possible to assemble the conduit connector 1500, the humidification chamber 1104, and the heater base 102 by either engaging the humidification chamber 1104 with the heater base 102 and then attaching conduit connector 1500 to the outlet port 1412 of the humidification chamber 1104, or attaching the conduit connector 1500 to the outlet port 1412 of the humidification chamber 1104 and then engaging the humidification chamber 1104 with the heater base 102. The latter assembly option is made simpler to follow because the conduit connector 1500 and the outlet port 1412 are configured to lockably engage, since this prevents separation of the conduit connector 1500 from the outlet port 1412 while the humidification chamber 1104 is slid onto the heater base 102. Additionally, with the latter assembly, the inspiratory conduit 120 and the humidification chamber 1104 can be preassembled for shipping, thereby eliminating one step from the setup process. Irrespective of the order of assembly, electrical or other connections between the inspiratory conduit 120 and/or conduit connector 1500 to the cartridge 1300 and/or the heater base 102 can be made as the conduit connector 1500 engages the cartridge 1300. With the latter assembly, the probes 302, 304, 306 can be inserted in the apertures 416, 414a, 414b as the chamber is installed upon the heater base 102 and the electrical and/or other connections of the conduit connector 1500 to the cartridge 1300 and/or heater base 102 also can be made with one motion (i.e., the motion of inserting the combined conduit connector 1500 and humidification chamber 1104 on the heater base 102). In the illustrated configuration, there is an electrical connection made between the heater base 102 and the conduit connector 1500 and there is an insertion of the probes 302, 304, 306 into the apertures 416, 414a, 414b; both of these connections occur in a single motion as the humidification chamber 1104 is installed on the heater base 102.

Similarly, disassembly can be performed in different sequences. More particularly, the conduit connector 1500 can firstly be removed from the outlet port 1412 of the humidification chamber 1104, followed by removal of the humidification chamber 1104 from the heater base 102. Alternatively, the humidification chamber 1104 can be removed from the heater base 102 while the conduit connector 1500 is still attached to the outlet port 1412 of the humidification chamber 1104. The latter option can advantageously help reduce the likelihood of a spill of fluids during disassembly and disposal of the consumables from the heater base 102.

Alignment and Engagement Features

To facilitate engagement of the conduit connector 1500, the humidification chamber 1104, and the heater base 102 on assembly thereof, various guides may be provided to control the orientation and/or position thereof relative to one another. More particularly, to enable the humidification chamber 1104 to be slid into engagement with the heater base 102 and the cartridge 1300, various orientation features can be provided on the humidification chamber 1104 and/or the cartridge 1300 such that, particularly when the conduit connector 1500 is attached to the outlet port 1412, the component parts are brought readily and easily into alignment. For example, the humidification chamber 1104 is able to be brought into full engagement with the heater base 102 such that the conduit connector 1500 is also brought into engagement with the cartridge 1300. As will be disclosed later, the conduit connector 1500 and/or the cartridge 1300 may additionally or alternatively include orientation features to help ensure that the conduit connector 1500 is connected to the humidification chamber 1104 with the conduit connector 1500 properly oriented to allow for easy coupling of the conduit connector 1500 and the humidification chamber 1104 to the heater base 102 and the cartridge 1300.

Alignment and Engagement Features for Humidification Chamber to Cartridge

As shown in FIGS. 28-34, the humidification chamber 1104 preferably includes a central boss, raised portion, or nose portion 1422 and rails or guide wings 1430. These features are configured to engage with a central channel or contoured recess 1322 and horizontal grooves or slots 1330, respectively, in the cartridge 1300, shown in FIGS. 35-38. Further discussion will be made with reference to the following coordinate system in which the Z-axis extends vertically from the heater plate 108, the Y-axis is aligned with the direction of engagement of the humidification chamber 1104 with the heater base 102, and the X-axis is perpendicular to both the Z- and Y-axes. Further, a width of the nose portion 1422 is defined along the X-axis, a length of the nose portion 1422 along the Y-axis and a height of the nose portion 1422 along the Z-axis.

In one embodiment, the nose portion 1422 has a smaller width at a first end than at a second end of the nose portion 1422, the first end of the nose portion 1422 being configured to be received first in the recess 1322. This provides some tolerance as to the position of the humidification chamber 1104 along the X-axis (as well as rotationally about the Z-axis), in order for the nose portion 1422 to be initially received in the recess 1322. Further, the wider second end of the nose portion 1422 can serve to refine the location of the nose portion 1422 along the X-axis (and rotationally about the Z-axis) (and hence also the humidification chamber 1104) in that the spacing or tolerance between the nose portion 1422 and the recess 1322 becomes reduced, thereby reducing the extent of relative movement.

In the embodiment shown, the recess 1322 is configured such that the inclined sidewalls of the nose portion 1422 abut corresponding and similarly inclined sidewalls of the recess 1322. Having the sidewalls of the nose portion 1422 and the sidewalls of the recess 1322 configured in this manner not only controls the position of the humidification chamber 1104 along the X-axis but also rotationally about the Y- and/or Z-axes since movement of the nose portion 1422 along the X-axis in at least two locations along the length of the nose portion 1422 is substantially inhibited, and also along the height of the nose portion 1422.

It is, however, possible to achieve some of these benefits where the sidewalls of the nose portion 1422 do not abut the sidewalls of the recess 1322. For example, if the nose portion 1422 is configured as shown but the sidewalls of the recess 1322 are substantially parallel along their length and spaced apart by a distance greater than the greatest width of the nose portion 1422 at the second end thereof, the configuration will still assist with initial insertion of the nose portion 1422 into the recess 1322 and at least significantly restrict movement of the nose portion 1422 along the X-axis at the second end of the nose portion 1422, although some rotational movement about the Z-axis may be possible. A similar result is achieved if the sidewalls of the nose portion 1422 are substantially parallel and the recess 1322 narrows along its length along the Y-axis from its opening to a width at least as great as that of the nose portion 1422.

The nose portion 1422 in combination with the recess 1322 may additionally or alternatively provide tolerance along at least the Z-axis with regard to the initial placement of the humidification chamber 1104. Further, according to particular embodiments, they may cooperate to refine the location of the humidification chamber 1104 along the Z-axis and/or rotationally about the X- and/or Y-axes.

Figure 36:
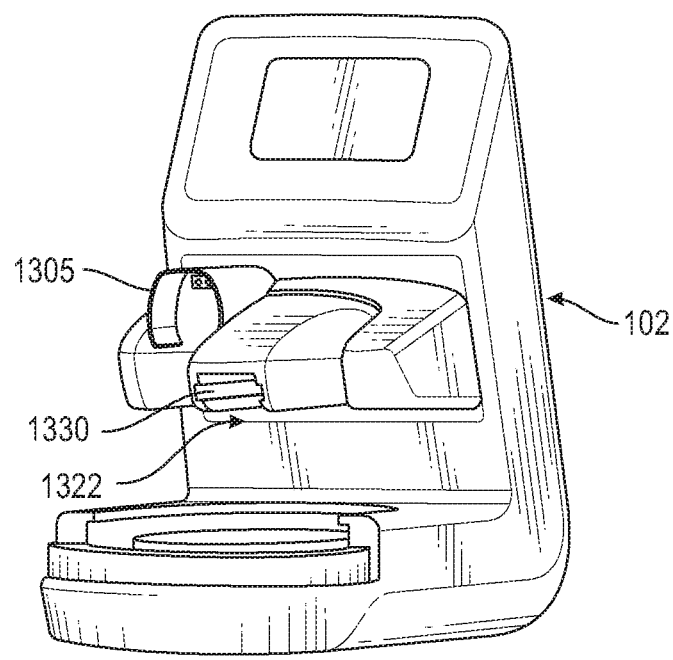

This tolerance is provided in a similar manner to the tolerance in the X-direction. As shown for example in FIG. 31, the height of the nose portion 1422 is lower at the first end than at the second end, the height being measured from the base plate 404. As shown in FIG. 36, the recess 1322 is similarly contoured, thereby providing for easy initial insertion followed by the refinement of position along the Z-axis on continued insertion of the humidification chamber 1104 into full engagement with the heater base 102. Similar to the description regarding width-wise tolerance along the X-axis, the opposing walls of the substantially downwardly facing underside of the recess 1322 may not abut along the length thereof with the upwardly facing topside of the nose portion 1422. For example, one or the other may be orientated to be substantially parallel to the heater plate 108 with similar drawbacks to those mentioned previously. More particularly, while initial insertion may be facilitated, the degree of refinement of the position of the humidification chamber 1104 along the Z-axis may be reduced and there may be less control to ensure that the base plate 404 is parallel to the heater plate 108. In some embodiments, the engagement of the guide wings 1430 with the grooves 1330 and/or other alignment features on the nose portion 1422 provide sufficient movement restriction to reduce the need for alignment and engagement of the base plate 404 of the humidification chamber 1104 with the heater plate 108 via the rim edge 220 of the top surface 208 of the heater base 102 and/or the rim edge 224 of the inner chassis 222. In some configurations, the heater base 102 does not include a rim edge 220. In some configurations, at least one of the rim edge 220 and the rim edge 224 may be omitted.

The nose portion 1422 may be provided in the absence of the guide wings 1430. However, the use of the guide wings 1430 is preferred, at least in embodiments in which the heater plate 108 is spring mounted so as to improve control of the positioning of the humidification chamber 1104 along at least the Z-axis and/or to ensure that the heater plate 108 is substantially parallel to the base plate 404. Conversely, the guide wings 1430 may be provided in the absence of the nose portion 1422 but such a configuration is not preferred because the nose portion 1422 can be more readily configured to assist in the initial locating of the humidification chamber 1104 and also to perform the initial coarse adjustment thereof to refine the position, with the possibility of the guide wings 1430 then being used to further refine the position of the humidification chamber 1104 along the Z-axis and controlling the orientation about at least the X- and Y-axes. Where the nose portion is omitted, the guide wings 1430 may, for example, be mounted on a substantially rigid mount that extends vertically from the humidification chamber 1104, with the guide wings 1430 extending laterally therefrom. The substantially rigid mount is preferably substantially planar, forming a generally T-shaped cross-section. However, to increase strength and rigidity, the mount may comprise more substantial element(s) having a thickness, but a thickness that does not generally bring the mount into direct contact with the cartridge 1300.

Figure 30:
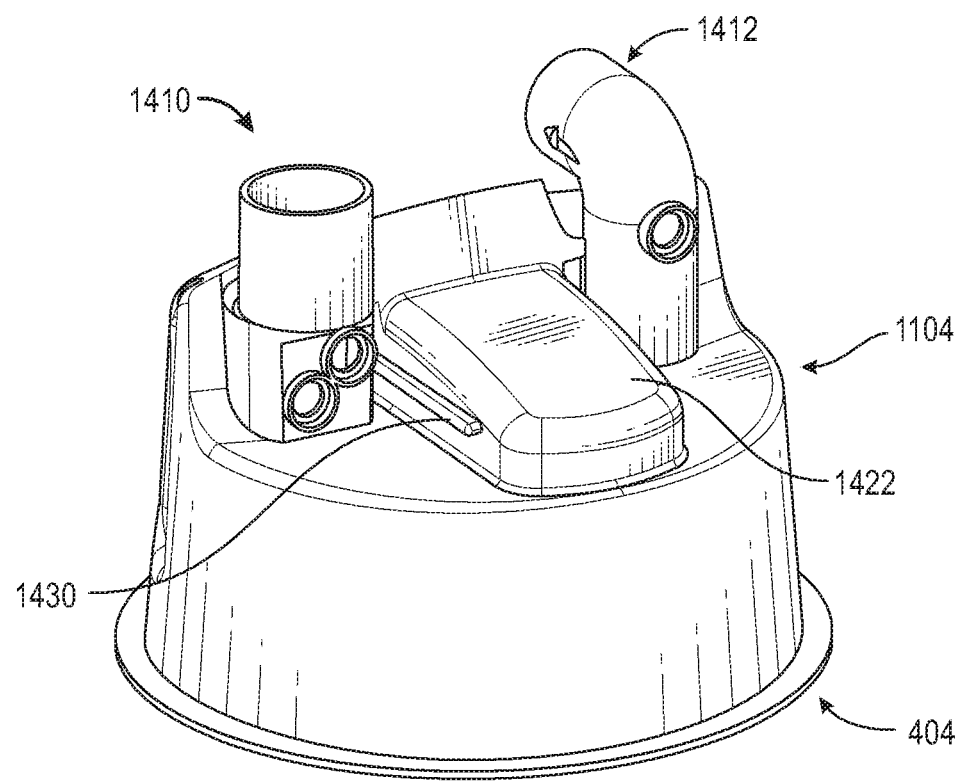
Figure 31:
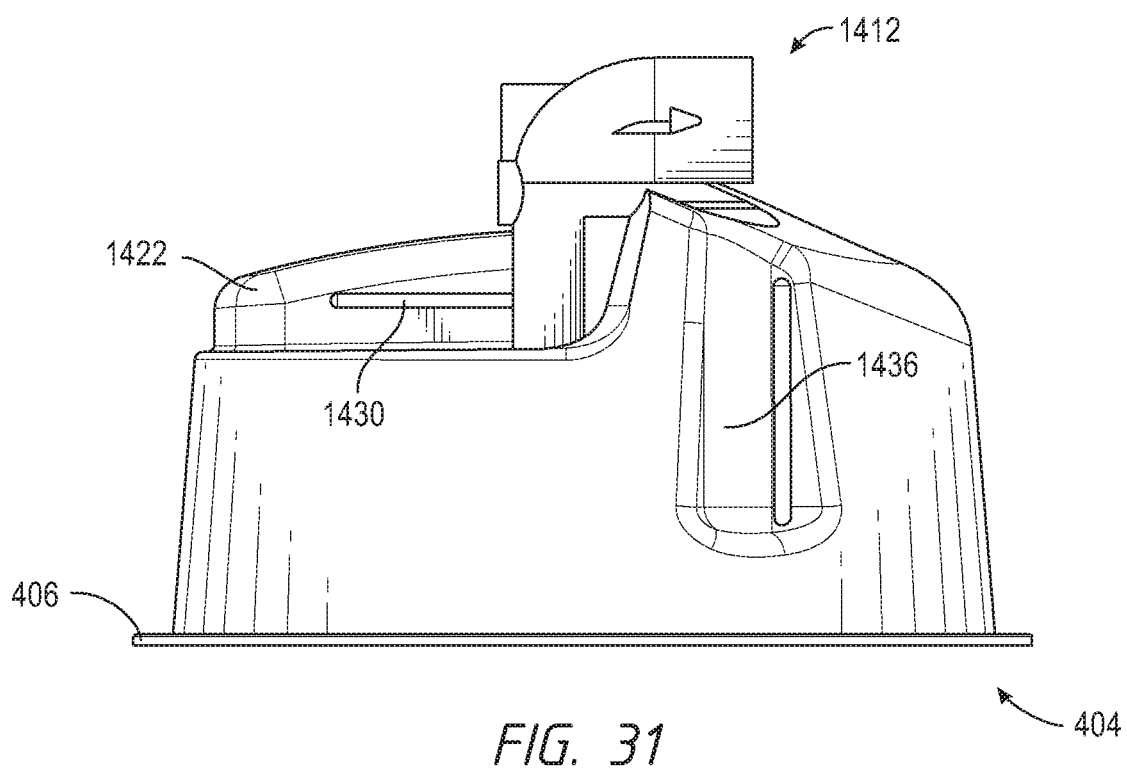
Figure 32:
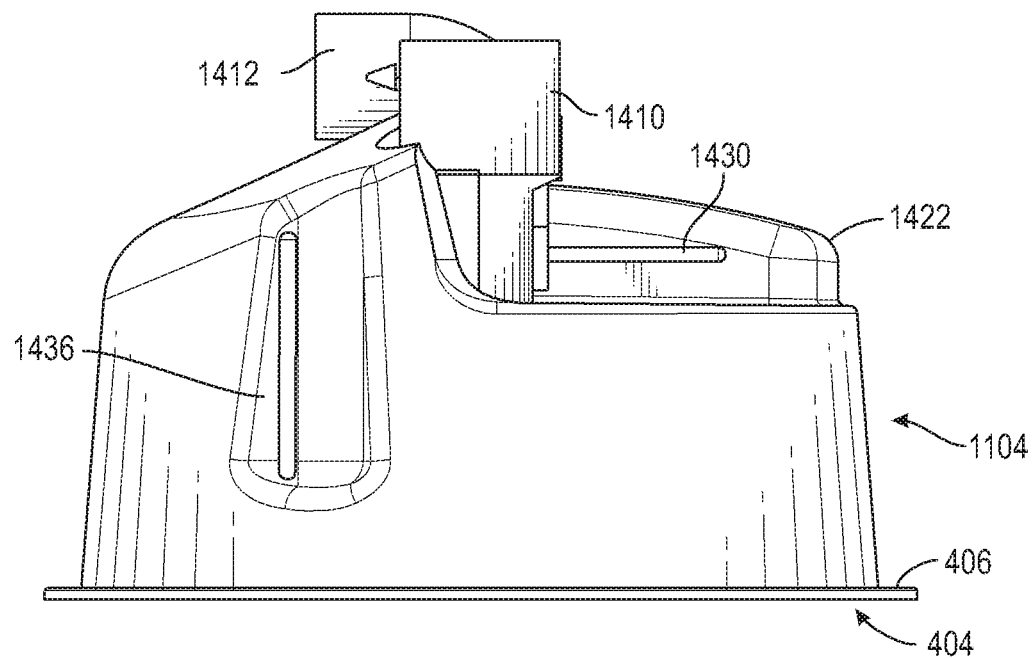
Figure 33:
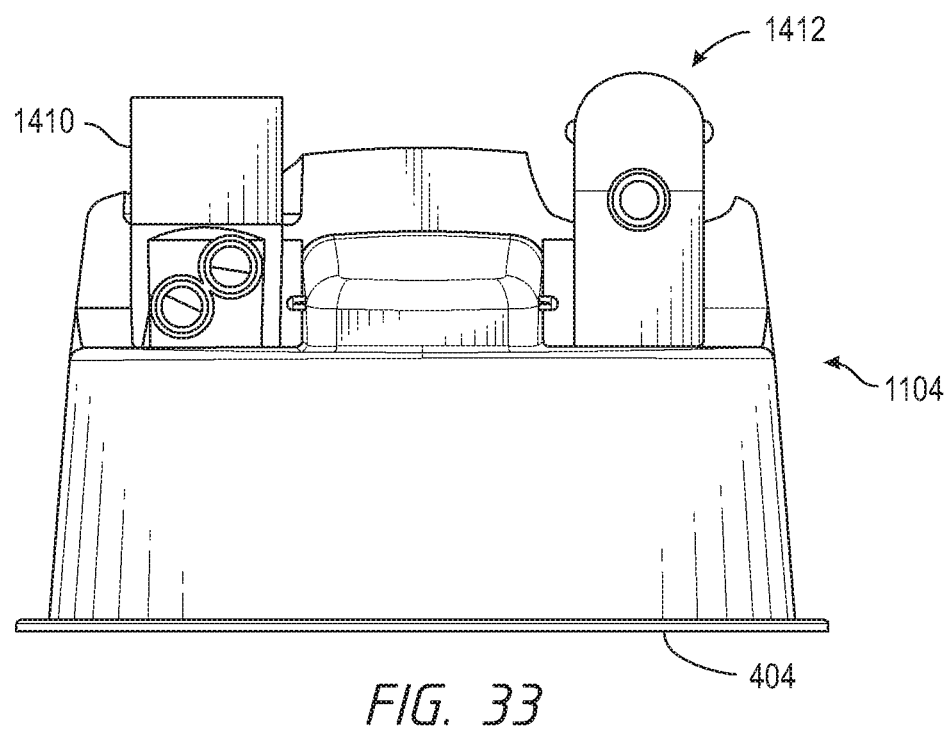
Figure 34:
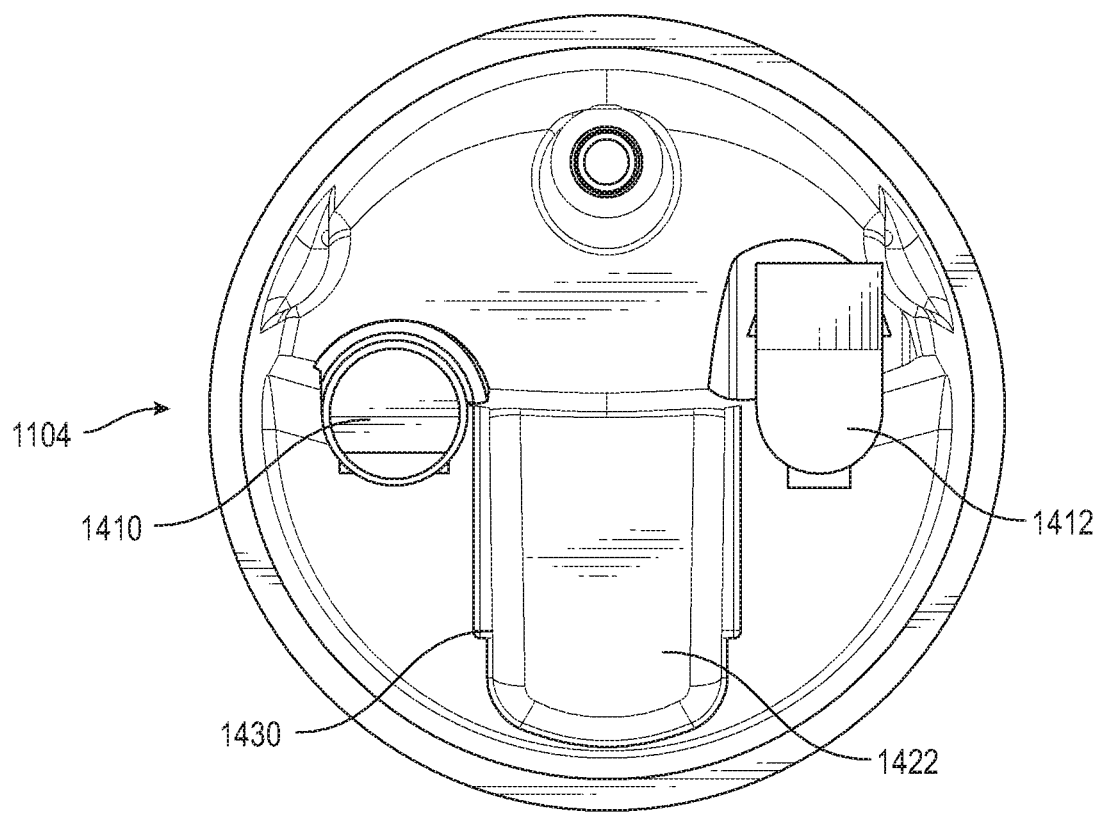
Figure 35:
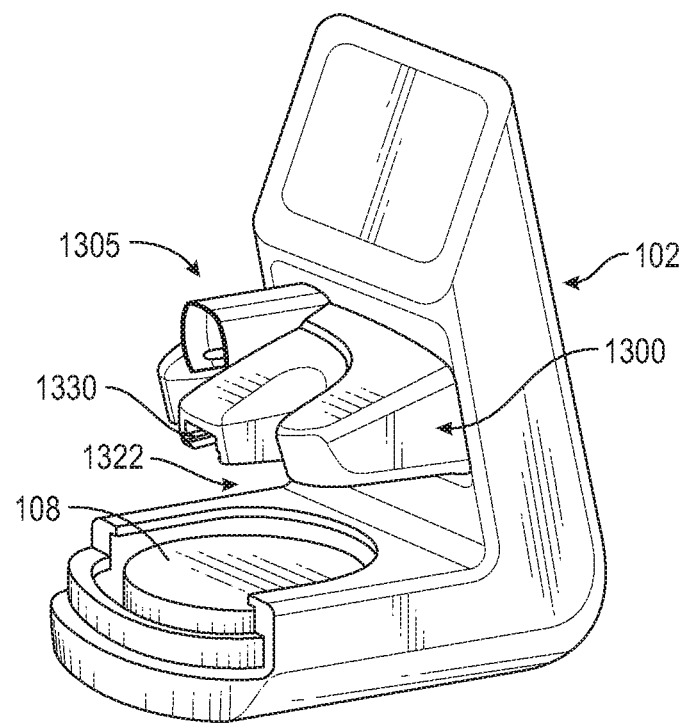
FIGS. 35-36 illustrate the heater base of FIGS. 25-27.

For example, as shown in FIG. 30, the guide wings 1430 do not extend to the first end of the nose portion 1422. Instead, they are spaced therefrom, thereby enabling initial engagement between the nose portion 1422 and the recess 1322 without engagement of the guide wings 1430 with the grooves 1330, this only occurring on continued engagement of the humidification chamber 1104 with the heater base 102 after the relative positions between the two have been refined.

As will be apparent, alternative guide means may be substituted. For example, the nose portion 1422 may be in the form of a contoured recess and vice versa such that a contoured recess of the humidification chamber 1104 receives a nose portion or projection of the cartridge 1300. Similarly the guide wings 1430 may be substituted with grooves that receive wings or other projections on the cartridge 1300. Other arrangements that perform the same function also can be used.

In some embodiments, for example as shown in FIG. 60, the cartridge 1300 includes a protrusion 1390 positioned generally below the first probe 1302. In some configurations, the protrusion 1390 has a generally horseshoe shape. In some configurations, the protrusion 1390 has a generally horseshoe shape with an opening defined in the lower portion. In configurations using the protrusion 1390, the outlet port 1412 can include a corresponding post 1490 positioned beneath the aperture 1416. The post 1490 and the protrusion 1390 are configured to engage each other to help inhibit, reduce the likelihood of, or prevent the humidification chamber 1104 rotating about the vertical or Z axis. In some configurations, engagement of the post 1490 and the protrusion 1390 helps to inhibit, reduce the likelihood of, or prevents rotation of the humidification chamber on the X axis. While the protrusion 1390 is shown formed on the cartridge 1300, in other embodiments the protrusion 1390 can formed on the chamber 1104 or on a combination of the chamber 1104 and cartridge 1300. In some configurations, the protrusion 1390 is formed such that an axial center of the outlet port 1412 intersects at least a portion of the protrusion 1390. The protrusion 1390 or post 1490 or both can be formed as a simple flat structure in some configurations. In some configurations there may be no post 1490 or protrusion 1390. The protrusion 1390 or post 1490 (where present) can limit how far back toward the spine 204 the outlet port 1412 can otherwise translate or travel. In other words, when the circuit connector 1500 is pushed onto the outlet port 1412, the chamber 1104 is susceptible to movement without any resisting structure. The protrusion 1390 limits how far back the outlet port 1412 can go so that the circuit connector 1500 can be secured to the outlet port 1412 (due to interaction of a ridge 1482 and a latching ring 1540) before the edge card 901 bottoms within the receiver 1388.

Figure 37:
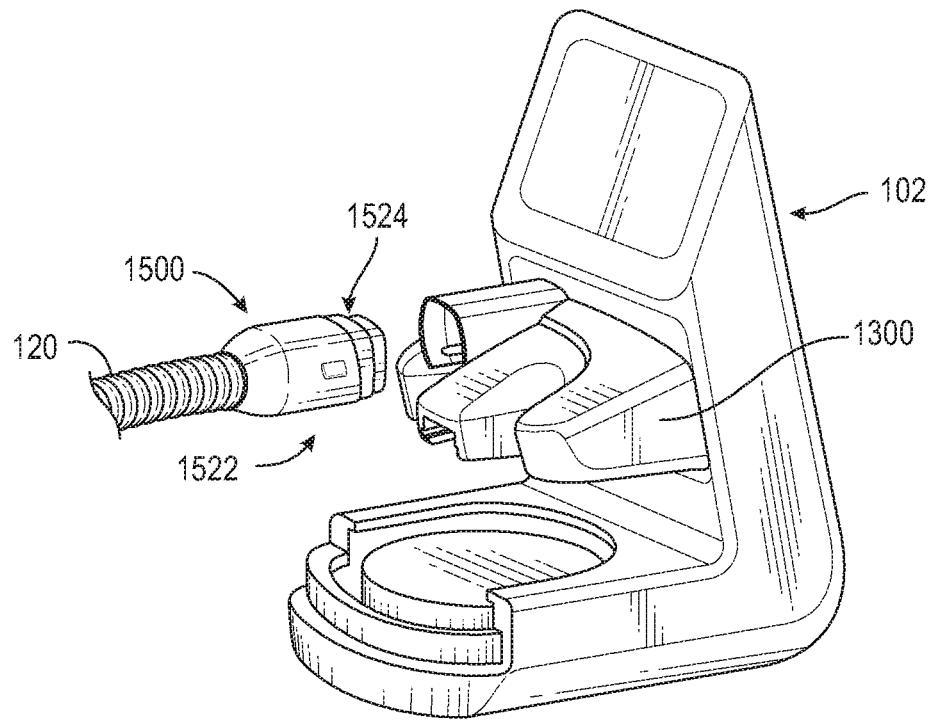
FIG. 37 illustrates the conduit connector and heater base of FIGS. 25-26.
Figure 70:
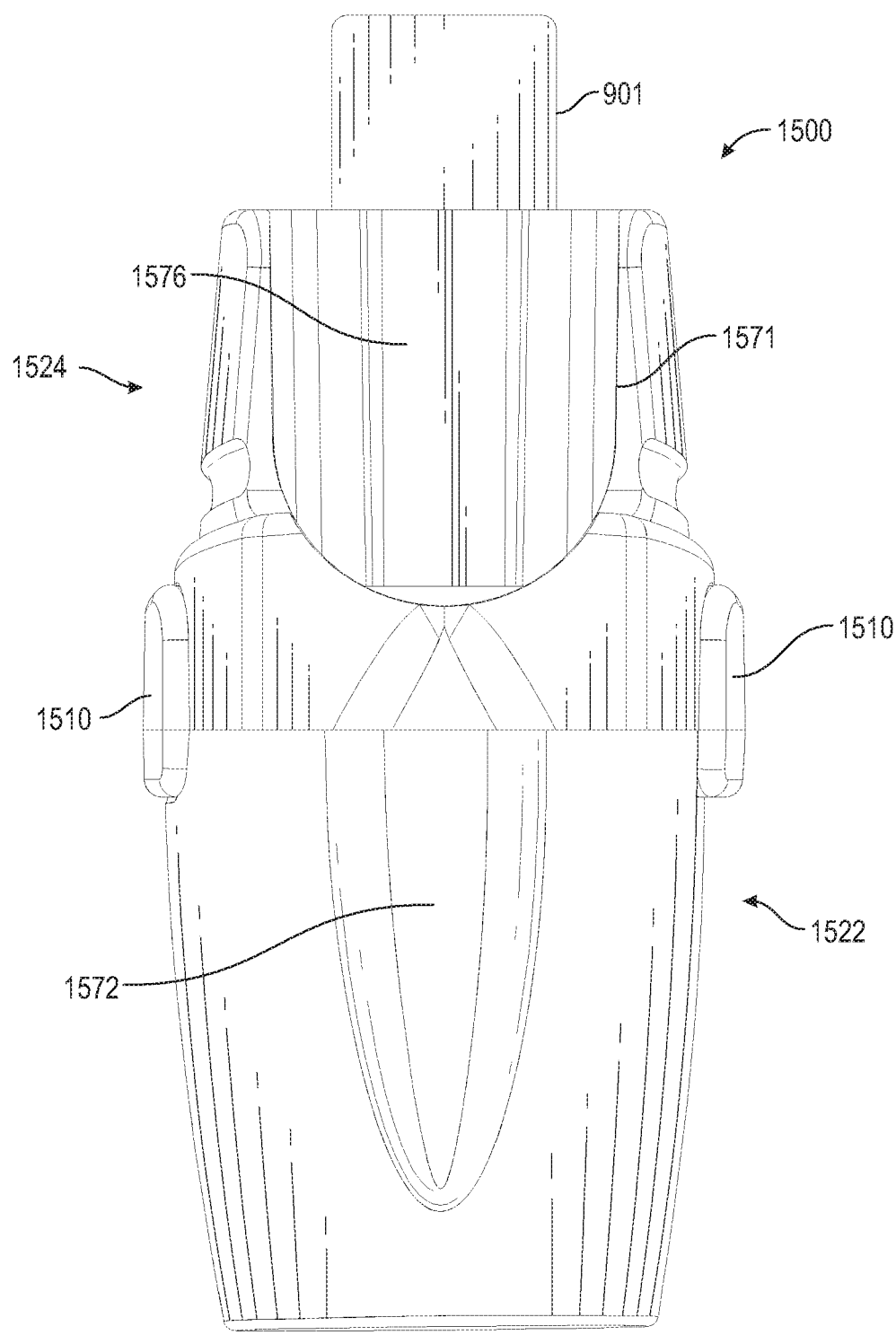
FIG. 70 illustrates a bottom view of the conduit connector of FIGS. 62-63.
Figure 72:
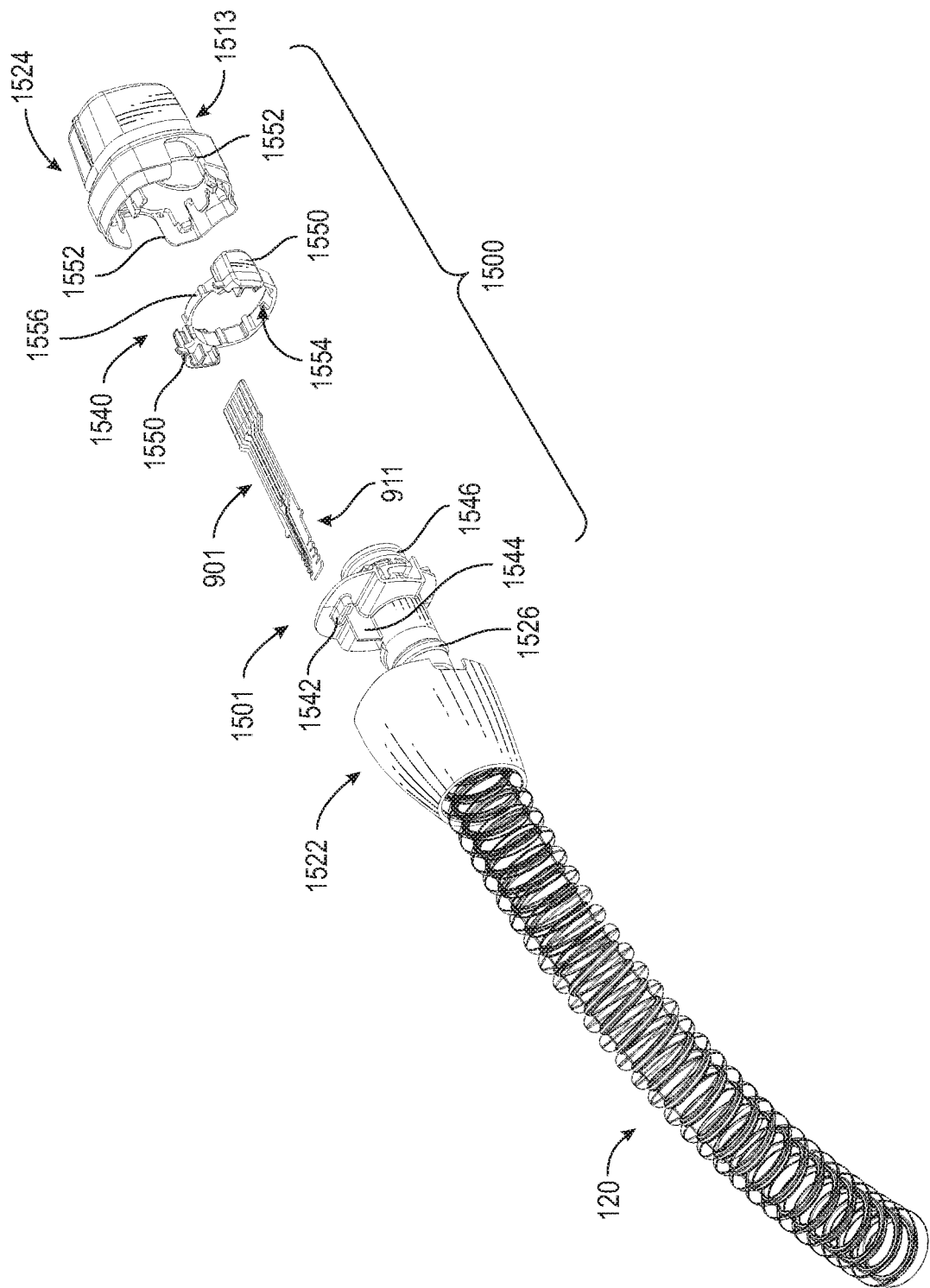
FIG. 72 illustrates an exploded view of the conduit and conduit connector of FIGS. 62-63 and 70-71.

Additionally or alternatively, guide means may be incorporated in the heater plate 108 and/or the base plate 404 of the humidification chamber 1104. For example, a ridge in the heater plate 108 may be configured to be received in a slot in the base plate 404 of the humidification chamber 1104, or vice versa Alignment and Engagement Features of Conduit Connector to Humidification Chamber In some embodiments, for example as shown in FIG. 37, the conduit connector 1500 includes a main body 1522 and an extending portion 1524. FIG. 72 is an exploded perspective view of the conduit connector 1500. As illustrated, the connector comprises the main body 1522 and the extending portion 1524. The main body 1522 and the extending portion 1524 can be snap-fit together or secured together in any suitable manner. As illustrated in FIG. 70, the extending portion 1524 can incorporate a cutout region 1571. The cutout region 1571 can be generally arcuate in shape as shown in FIG. 70. Thus, the extending portion 1524 may not form a complete cylinder. The cutout region 1571 accommodates the outlet port 1412 of the humidification chamber 1104 when the conduit connector 1500 is connected thereto while projecting over top of at least a portion of the outlet port 1412.

When connected, the main body 1522 and the extending portion 1524 generally enclose a majority of an edge card 901 as well as an inner plug portion 1501 and the latching ring 1540. As such, the main body 1522 and the extending portion 1524 define an outer shell for the conduit connector 1500.

The inner plug portion 1501 connects to the inspiratory conduit 120 in any suitable manner. In some configurations, the inner plug portion 1501 of the conduit connector 1500 includes a spiraling ridge 1526. The spiraling ridge 1526 is designed and configured to receive the spiral of the inspiratory conduit 120. The spiraling ridge 1526 allows the inner plug portion 1501 to be threaded into the end of the inspiratory conduit 120.

The inner plug portion 1501 includes a passage 1542 that receives the edge card 901. In particular, a mounting region 911 of the edge card 901 can be inserted through the passage 1542. The mounting region 911 can be supported by a fin 1544, for example but without limitation. With the edge card 901 in position relative to the inner plug portion and the inner plug portion 1501 inserted into the conduit, the wires of the conduit can be connected to the mounting region 911 and the conduit and mounting region can be sealed to reduce or eliminate the likelihood of leaks and to provide electrical insulation.

The inner plug portion 1501 can include an outer groove 1546 near a distal end of the inner plug portion 1501. The outer groove 1546 can receive a seal member (not shown). The seal member (not shown) can have any suitable configuration. In some configurations, the seal member is generally T-shaped with a wide band from which a single rib extends radially outward. In some configurations, the rib extends radially outward from an axial center of the wide band. Other sealing members, such as o-rings, V-shaped seals, double lip seals or the like also can be used. The sealing member (not shown) will seal against the inside of the outlet port 1412 when the conduit connector 1500 is connected to the humidification chamber 1104.

In the illustrated configuration, the extending portion 1524 houses the latching ring 1540. Other configurations can be used and the latching ring 1540 can be positioned within the extending portion 1524 or the main body 1522 or a combination of the two. In the illustrated configuration, the latching ring 1540 includes two buttons 1550 that protrude outward from the extending portion 1524 via corresponding openings 1552. The buttons 1550 can be on opposing sides of the latching ring 1540.

The latching ring 1540 can include an orientation feature 1554 to assist with proper orientation and assembly of the latching ring 1540 to the extending portion 1524. With the orientation feature 1554 oriented in the proper direction, the latching ring 1540 can be inserted into an end of the extending portion 1524. The latching ring 1540 is generally trapped within a passage inside of the extending portion 1524 around about the sides and bottom of the latching ring 1540 such that compression of the buttons 1550 results in deflection of the top of the latching ring 1540. In other words, squeezing the buttons 1550 together results in an upper portion 1556 deflecting upwardly away from an axial center of the conduit connector 1500. Other portions of the ring can be configured to deflect in other configurations of systems.

With the edge card 901 extending through a distal end of the extending portion 1524, the extending portion 1524 can be secured to the inner plug portion 1501. In some configurations, the edge card 901 can be positioned within the extending portion 1524 so that a portion of the edge card 901 is exposed through an opening in the wall of the extending portion 1524. The main body 1522 can be secured to the inner plug portion 1501 such that the extending portion 1524 and the main body 1522 are secured together using the inner plug portion 1501. In the illustrated configuration, each of these connections uses snap-fit constructions but other configurations also can be used.

Figure 61B:
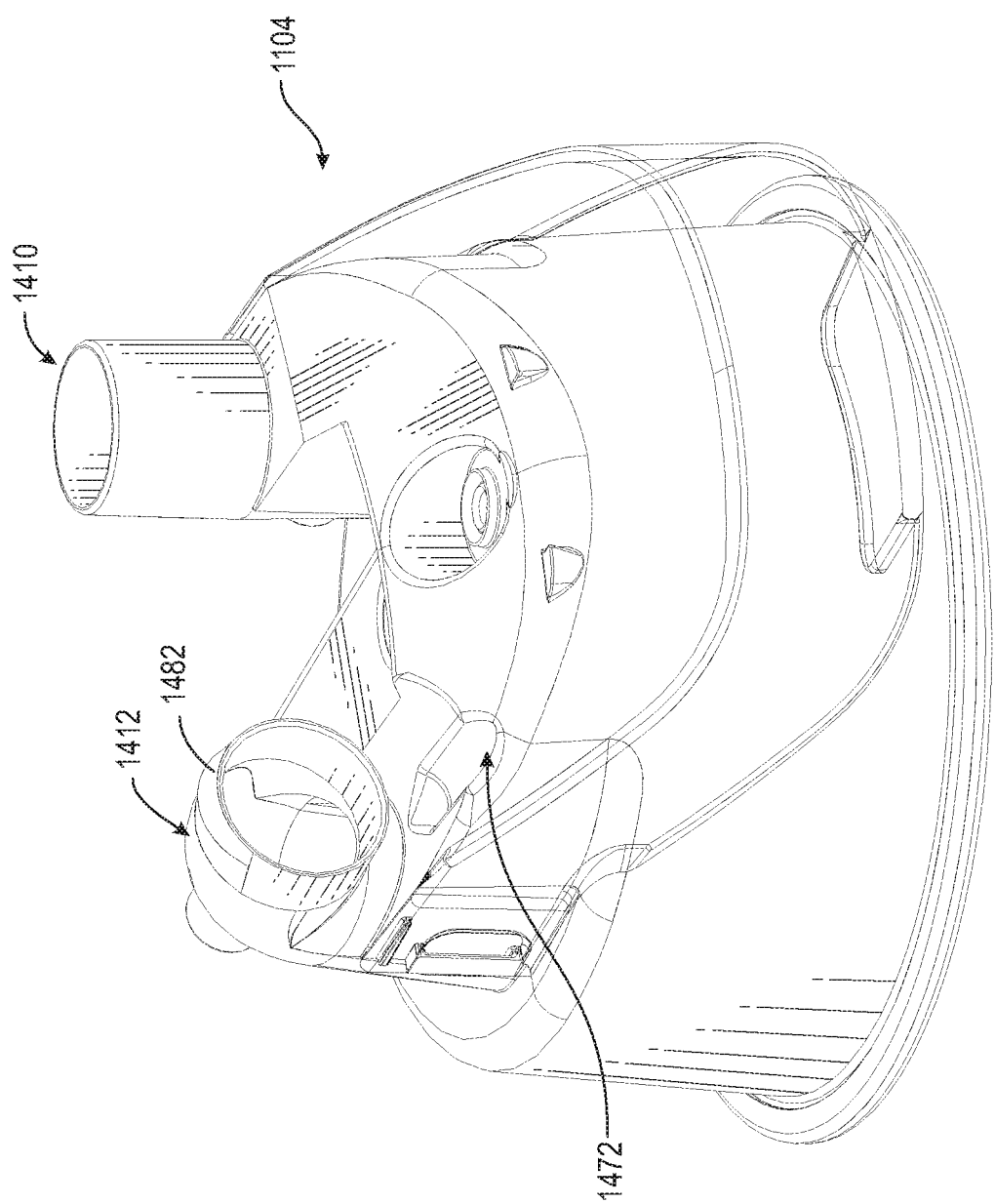

When assembled, the latching ring 1540 overlies the distal end of the inner plug portion 1501. In some configurations, the latching ring 1540 generally overlies the portion of the inner plug portion 1501 that receives the sealing member. Thus, when the conduit connector 1500 is fitted to the outlet port 1412, the latching ring 1540 deflects over the ridge 1482 (see FIGS. 61 and 61B) and the latching ring 1540 is secured behind the ridge 1482 while the sealing member seals within the opening of the outlet port 1412 to establish both a mechanical coupling and a pneumatic seal between the humidification chamber 1104 and the conduit connector 1500. As shown in FIG. 70, a lower surface of the extending portion 1524 can include a groove or clearance 1576 to accommodate the ridge 1482 (shown in FIG. 61B) as the conduit connector 1500 slides into position on the outlet port 1412. In FIG. 70, the groove 1576 is shown extending along the center of the extending portion 1524. In some configurations, the groove or clearance 1576 approximates the shape of the ridge 1482.

In the illustrated configuration, the ridge 1482 extends only around a portion of the opening of the outlet port 1412. The ridge 1482, because it is engaged by the latching ring 1540, which only deflects in the upper portion 1556, only need extend a portion of the circumference of the outlet port 1412. In the illustrated configuration, the ridge 1482 extends less than the circumferential span of the deflectable portion of the latching ring 1540. Other configurations are possible.

Figure 39:
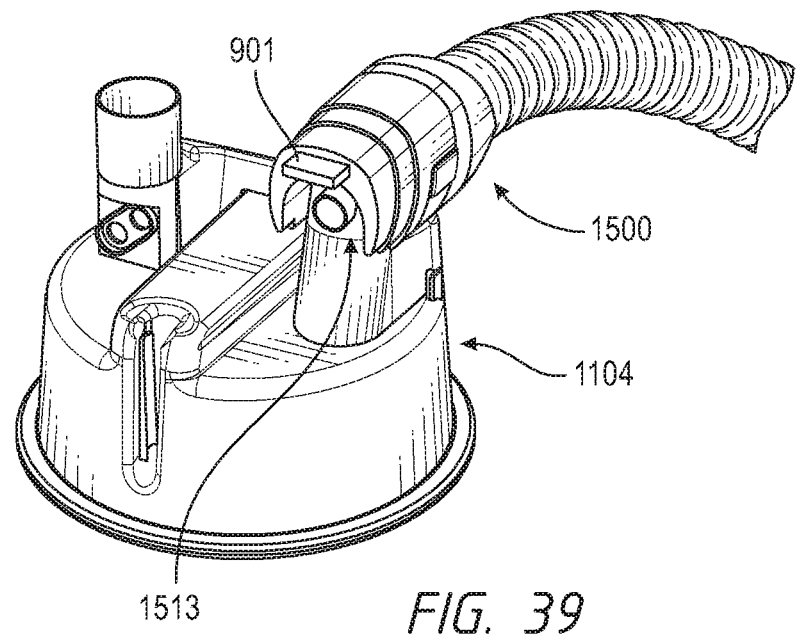
FIG. 39 illustrates the conduit connector coupled to the humidification chamber of FIGS. 25-26.
Figure 47:
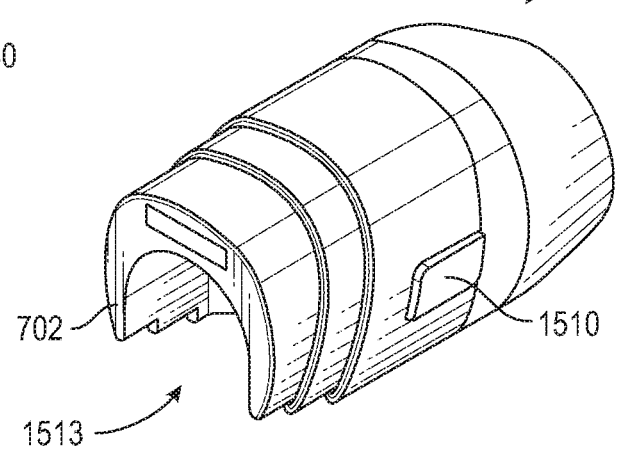
FIGS. 47-54 illustrate another example embodiment of a conduit connector.
Figure 48:
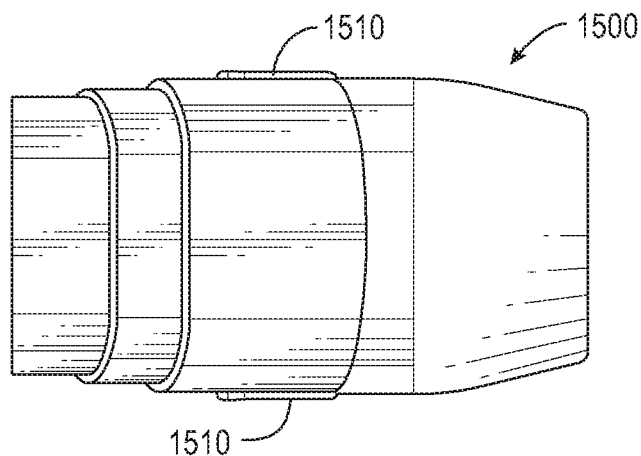

As shown in FIGS. 39 and 47, the conduit connector 1500 preferably includes a cutout 1513 configured to accommodate a substantially vertical portion of the outlet port 1412. Again, this helps to ensure that the conduit connector 1500 is correctly oriented as it is inserted onto the end of the outlet port 1412 since full insertion is only possible with correct alignment. Further, this arrangement provides for a stronger coupling and allows for electrical connection as will be described below. Again, at least an initial portion of the cutout 1513 may be angled or curved such that the first part of the cutout 1513 that receives the vertical portion of the outlet port 1412 is wider than the outlet port 1412, providing some tolerance as to the required initial alignment. However, where the outlet port 1412 is generally of a circular cross-section, this may not be required as some tolerance is inherently provided due to the circular shape of the outlet port 1412.

Figure 40:
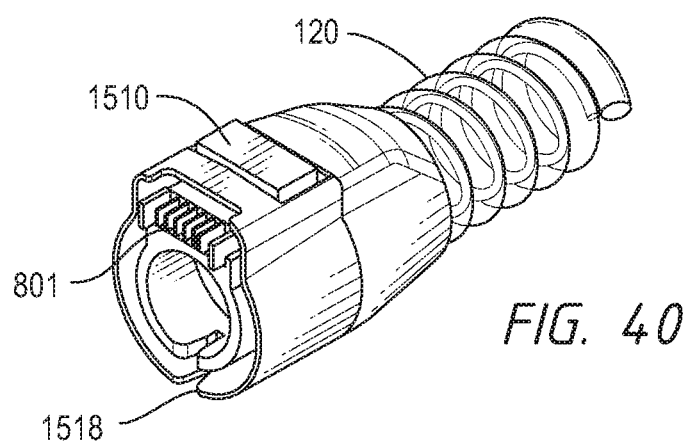
FIGS. 40-41 illustrate an example embodiment of a conduit connector.
Figure 42:
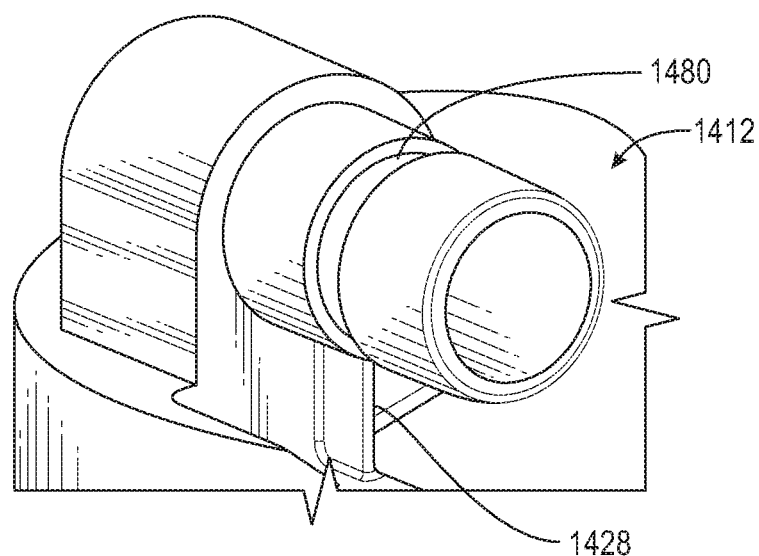
FIG. 42 illustrates an example embodiment of an outlet port of a humidification chamber configured to receive the conduit connector of FIGS. 40-41.

Referring to FIGS. 40 and 42, the conduit connector 1500 may additionally or alternatively include an angled groove or cutout 1518 that receives a similarly angled protrusion 1428 on the outlet port 1412. This serves to obtain and secure orientation of the conduit connector 1500 and the outlet port 1412 relative to one another. The angled protrusion 1428 also serves to strengthen the outlet port 1412 by increasing the amount of material connecting the outlet port 1412 to the top of the humidification chamber 1104.

Figure 49:
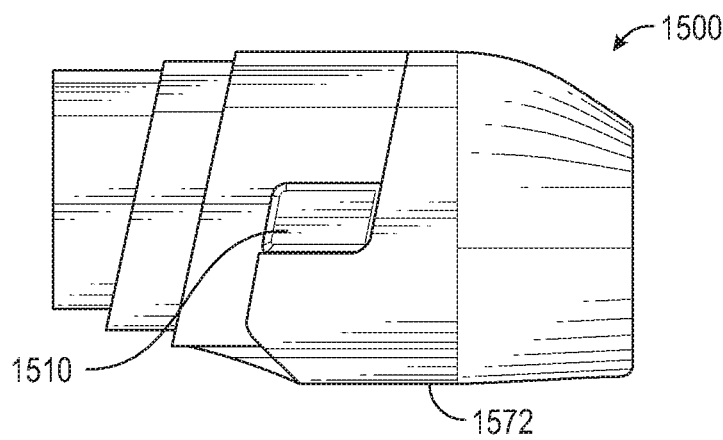
Figure 50:
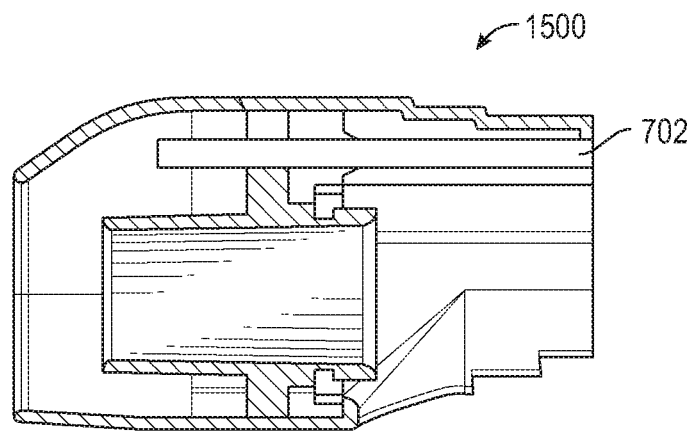
Figure 51:
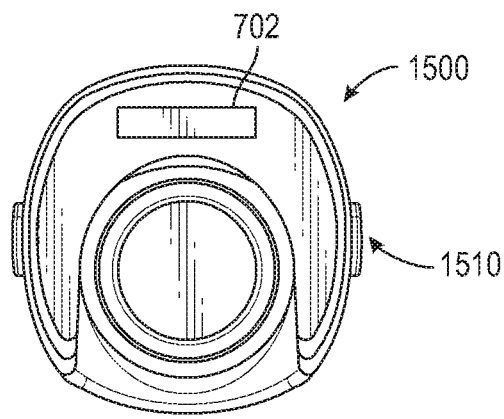
Figure 71:
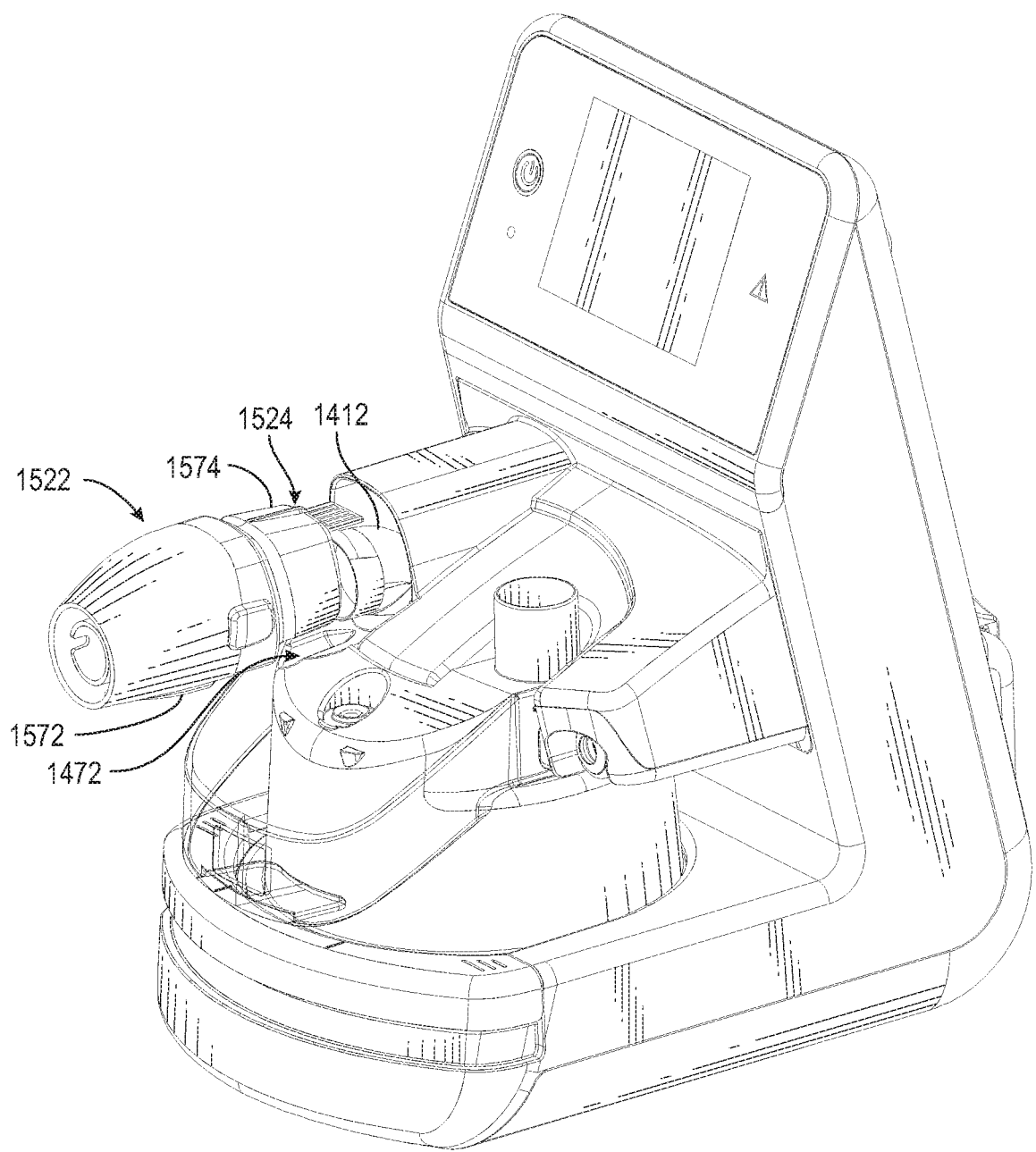
FIG. 71 illustrates the conduit connector of FIGS. 62-63 and 70 being installed on the humidification chamber of FIGS. 61 and 61B and the heater base of Figure and cartridge of FIGS. 60 and 65-66.

In some embodiments, for example as shown in FIGS. 49, 70 and 71, a bottom surface of the main body 1522 of the conduit connector 1500 includes a ridge 1572 configured to engage or mate with a corresponding groove 1472 positioned on the top of the humidification chamber 1104 forward of the outlet port 1412 to help inhibit or prevent rotating of the conduit connector 1500 and therefore the inspiratory conduit 120. The combination of the groove 1472 and the ridge 1572 combine to help orient the conduit connector 1500 during coupling as well. As shown in FIG. 70, the ridge 1572 can be generally diamond-shaped. In the illustrated embodiment, the ridge 1572 is asymmetrical; the bottom portion of the ridge 1572 shown in FIG. 70, which is the portion farther away from the heater base 102 when the conduit connector 1500 is coupled to the cartridge 1300, is longer than the top portion of the ridge 1572.

Figure 41:
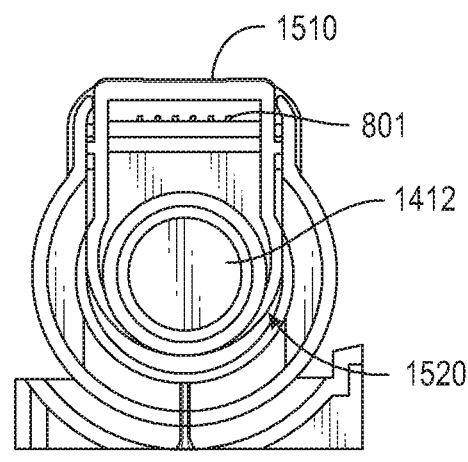
Figure 43:
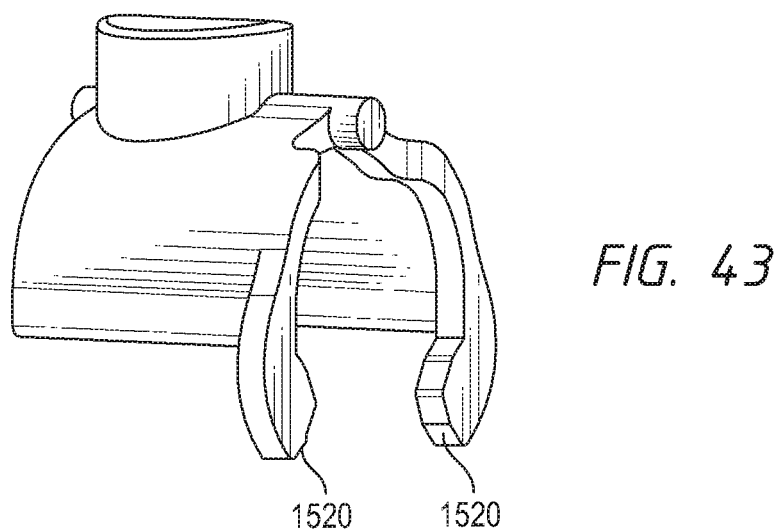
FIGS. 43-44 illustrate another example embodiment of a conduit connector.
Figure 44:
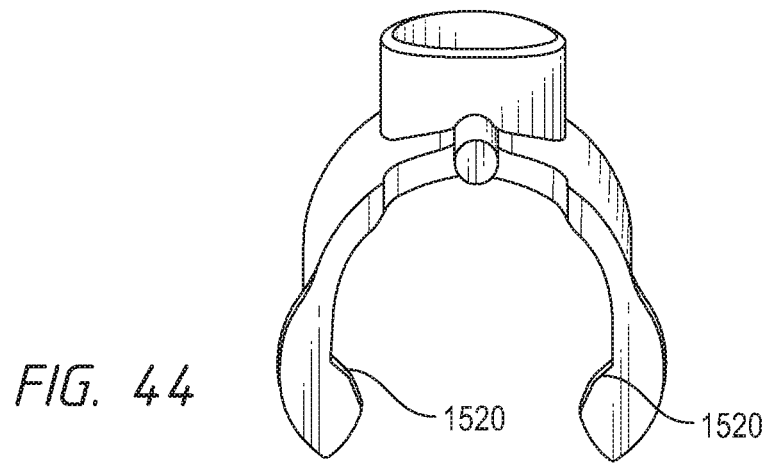

FIGS. 40-42 show an embodiment of a lockable but releasable coupling between the conduit connector 1500 and the outlet port 1412. The conduit connector 1500 includes the button 1510 that may be manually actuated such as by a thumb and/or finger to enable the conduit connector 1500 to be removed from the outlet port 1412. In the illustrated configuration, the button 1510 is formed from a resiliently elastic material and has a portion configured to be received in a recess 1480 formed in the outer wall of the outlet port 1412. Depression of the button 1510 disengages an engaging portion of the button 1510 from the recess 1480. FIGS. 43 and 44 show an alternative embodiment where the button 1510 is formed from a substantially rigid material but may be spring mounted. Depression of the button 1510 acts against the spring and disengages engaging portion 1520 of the button 10 from recesses in an outer wall of the outlet port 1412.

Figure 45:
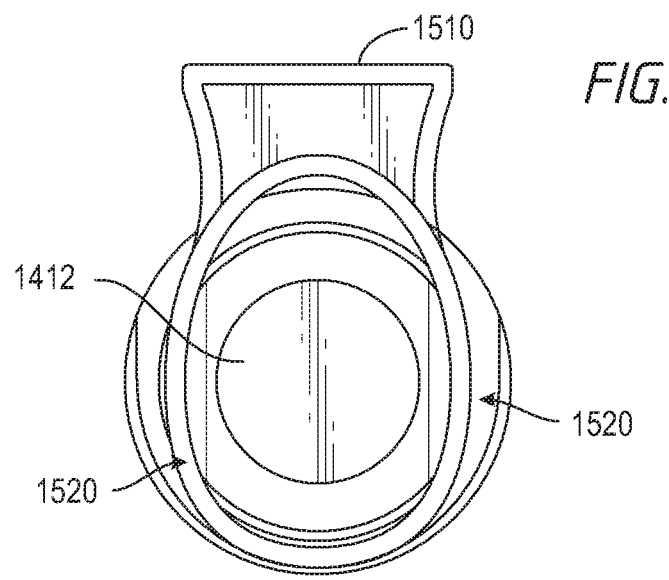
FIG. 45 illustrates another example embodiment of a conduit connector.
Figure 46:
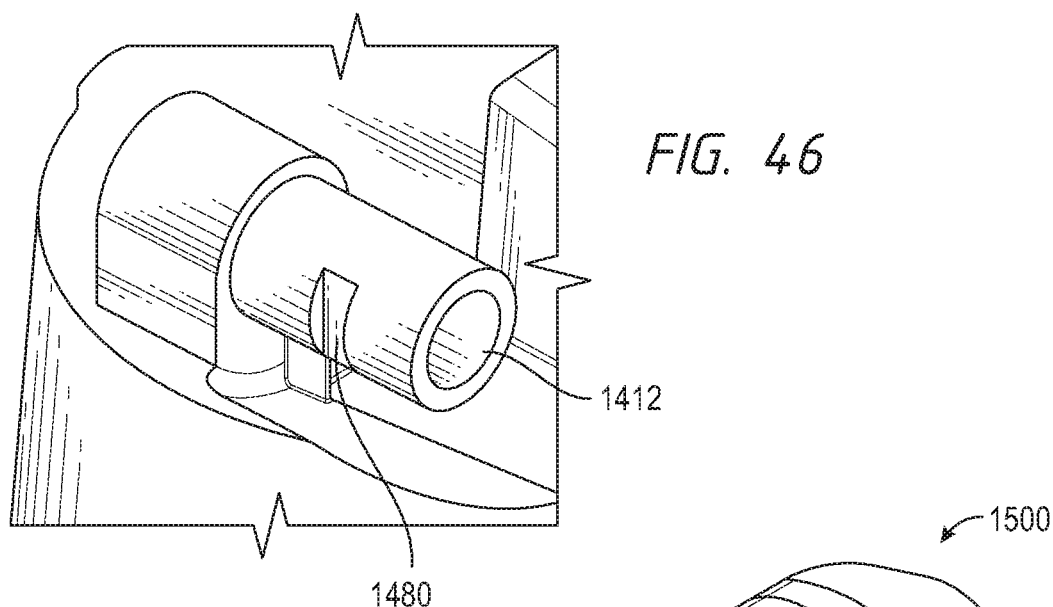
FIG. 46 illustrates an example embodiment of an outlet port of a humidification chamber configured to receive the conduit connector of FIG. 45.

FIGS. 45-46 show an alternative embodiment where the button 1510, or at least the engaging portion 1520 thereof is resiliently elastic whereby at least a portion of the button 1510 deforms to disengage the engaging portions 1520 from recesses 1480 in the outlet port 1412.

Figure 52:
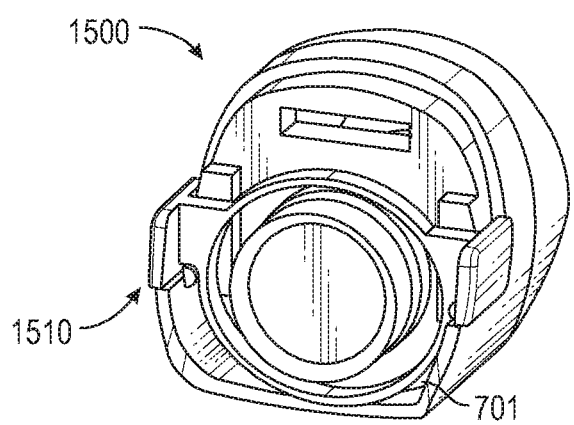
Figure 53:
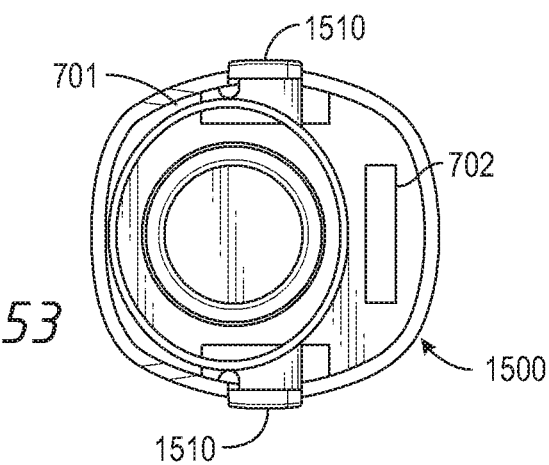
Figure 54:
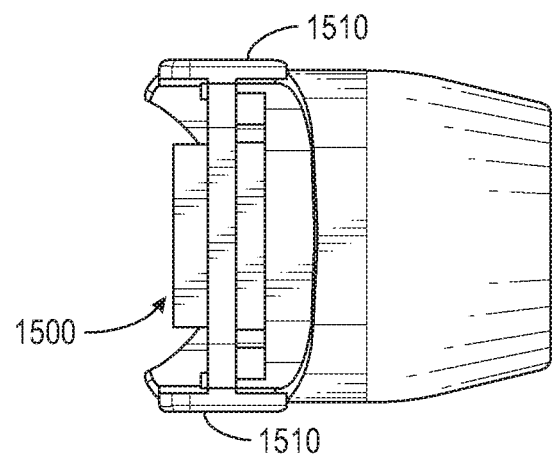

FIGS. 47-54 show an alternative embodiment of a conduit connector 1500. In FIGS. 52-54, part of the conduit connector 1500 is removed to show additional detail. According to this embodiment, the buttons 1510 are positioned on sides of the conduit connector 1500 as this can be more convenient in being placed at natural contact points for a user when attempting to disconnect the conduit connector 1500 from the outlet port 1412. The buttons 1510 are integral with or operably coupled to an elastically deformable ring 701. Depression of the buttons 1510 disengages the ring 701 from recesses formed in at least one of the upper and lower outer surfaces of the outlet port 1412, allowing the conduit connector 1500 to be removed.

Figure 55:
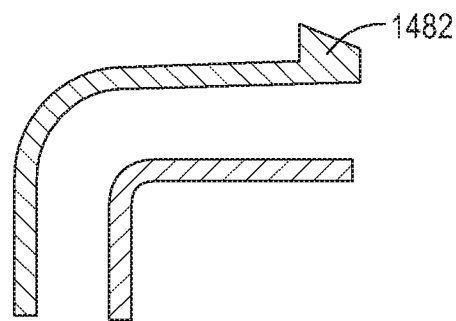
FIG. 55 illustrates a section view of another example embodiment of an outlet port of a humidification chamber.

As an alternative to recesses, the ridge 1482 may be used in the outlet port 1412 as shown in cross-section in FIG. 55. This applies to this and other embodiments disclosed herein. In some such embodiments, when the conduit connector 1500 is coupled to the outlet port 1412, the top of the ring 701 rests behind (or closer to the heater base 102 than) the ridge 1482. To disengage the conduit connector 1500 from the outlet port 1412, the buttons 1510 are depressed to deform the ring 701 such that the top of the ring 701 rises above the level of the ridge 1482 and the conduit connector 1500 can be removed from the outlet port 1412.

Figure 58:
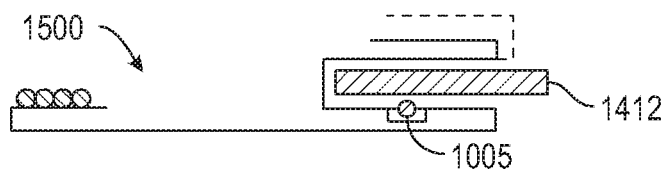
FIG. 58 illustrates another example embodiment of a conduit connector coupled to an outlet port.
Figure 58:
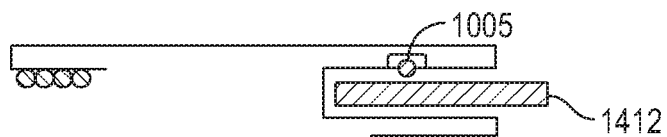

FIG. 58 is a cross-sectional view of a conduit connector 1500 engaged with an outlet port 1412 of the humidification chamber 1104. In this embodiment, the conduit connector 1500 has a male connection such that at least a portion of the conduit connector 1500 is received inside the outlet port 1412. An o-ring 1005 or other seal is used to seal between the male parts and the inside wall of the outlet port 1412.

Figure 59:
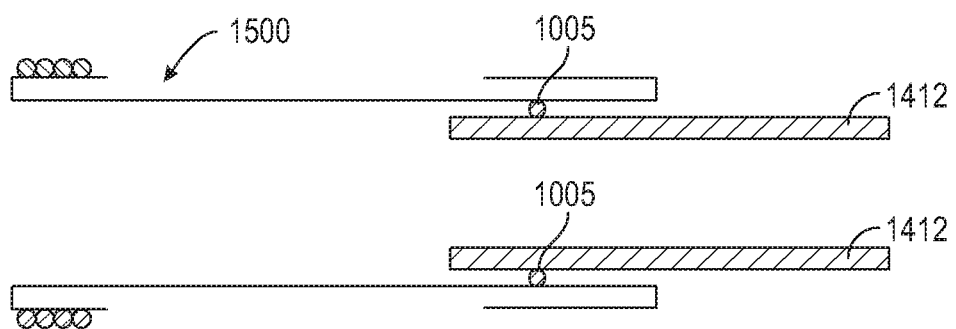
FIG. 59 illustrates another example embodiment of a conduit connector coupled to an outlet port.

FIG. 59 shows a view similar to that of FIG. 58 but modified such that the outlet port 1412 is configured as the male part that mates with the inner wall of the inlet of the conduit connector 1500. Again, an o-ring 1005 or other seal may be used to reduce or eliminate the likelihood of leakage.

Electrical Connections

Figure 38:
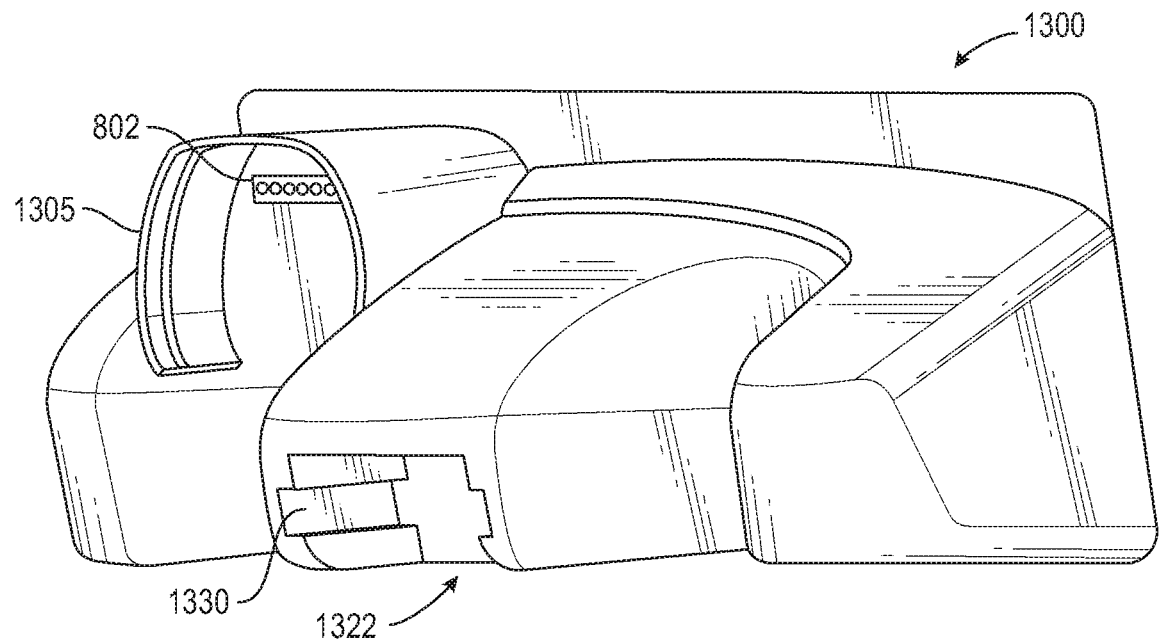
FIG. 38 illustrates an example embodiment of a cartridge.

Example electrical connections 801 are shown in FIGS. 40 and 41. The electrical connections can be provided in the extending portion 1524 of the conduit connector 1500 such that they extend beyond the pneumatic connection and electrically and/or communicatively couple to a cooperative connector 802 on the cartridge 1300 as shown in FIG. 38. In other embodiments, the pneumatic connection extends beyond the electrical connections, or the electrical and pneumatic connections extend the same amount. As shown in FIGS. 40 and 41, the electrical and other connections may be formed by blade contacts on the conduit connector 1500 that are received in respective recesses in the cartridge 1300 that house contacts for connecting thereto. In other embodiments, the electrical connections may be formed by blade contacts on the conduit connector 1500 that are can be positioned touching blade contacts located in a shroud 1305 that forms a portion of the cartridge 1300. Other connectors such as pins may alternatively be used but blade contacts are advantageous in providing some tolerance in the exact relative positioning of the blades in the recesses. In the embodiment shown, some vertical tolerance is provided for.

Figure 56:
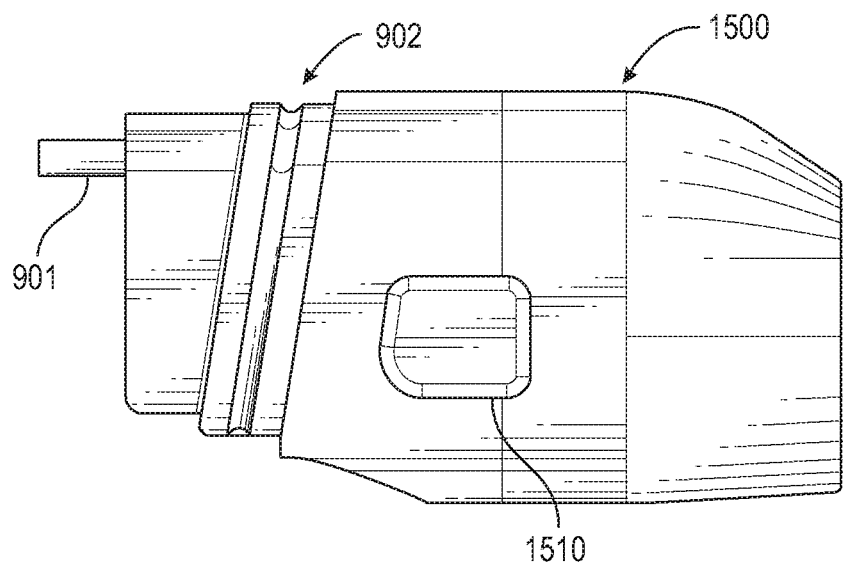
FIGS. 56-57 illustrate an example embodiment of a conduit connector.
Figure 57:
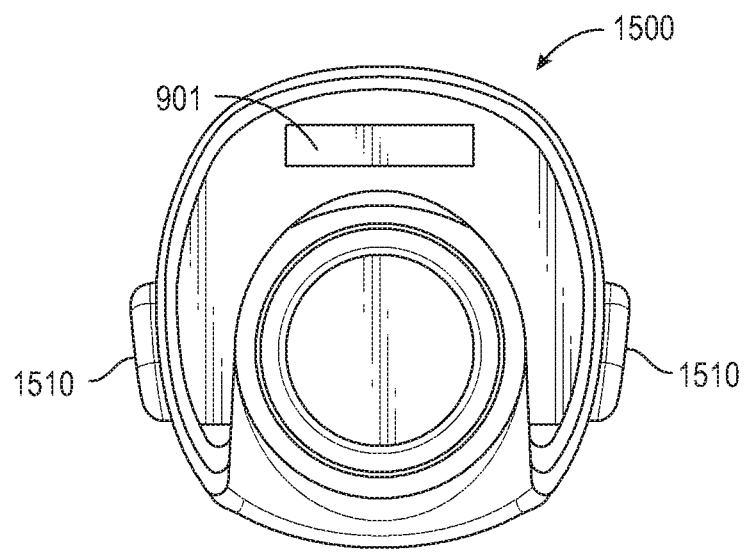

In the embodiment shown in FIGS. 47-54, the conduit connector 1500 includes a cavity 702 for housing electrical or other connections. A further embodiment is shown in FIGS. 56-57 wherein the electrical terminal is in the form of the edge card 901.

According to an alternative embodiment, the electrical contacts comprise one or more pogo or spring pin contacts that include spring-mounted pins housed in passages that allow them to vary the extent to which they protrude from the housing, thereby providing tolerance in the relative positions of the conduit connector 1500 and the cartridge 1300 along the axes of the pins. Further, the ability for the pins to become depressed can make insertion of the pins into the apertures that house cooperating or mating connectors easier.

According to another alternative embodiment, the electrical connections comprise edge card connectors or card edge connectors, wherein a first part of the connector has one or more conductive tracks provided on a printed circuit board and configured to make contact with one or more pins of a second part of the connector.

Figure 62:
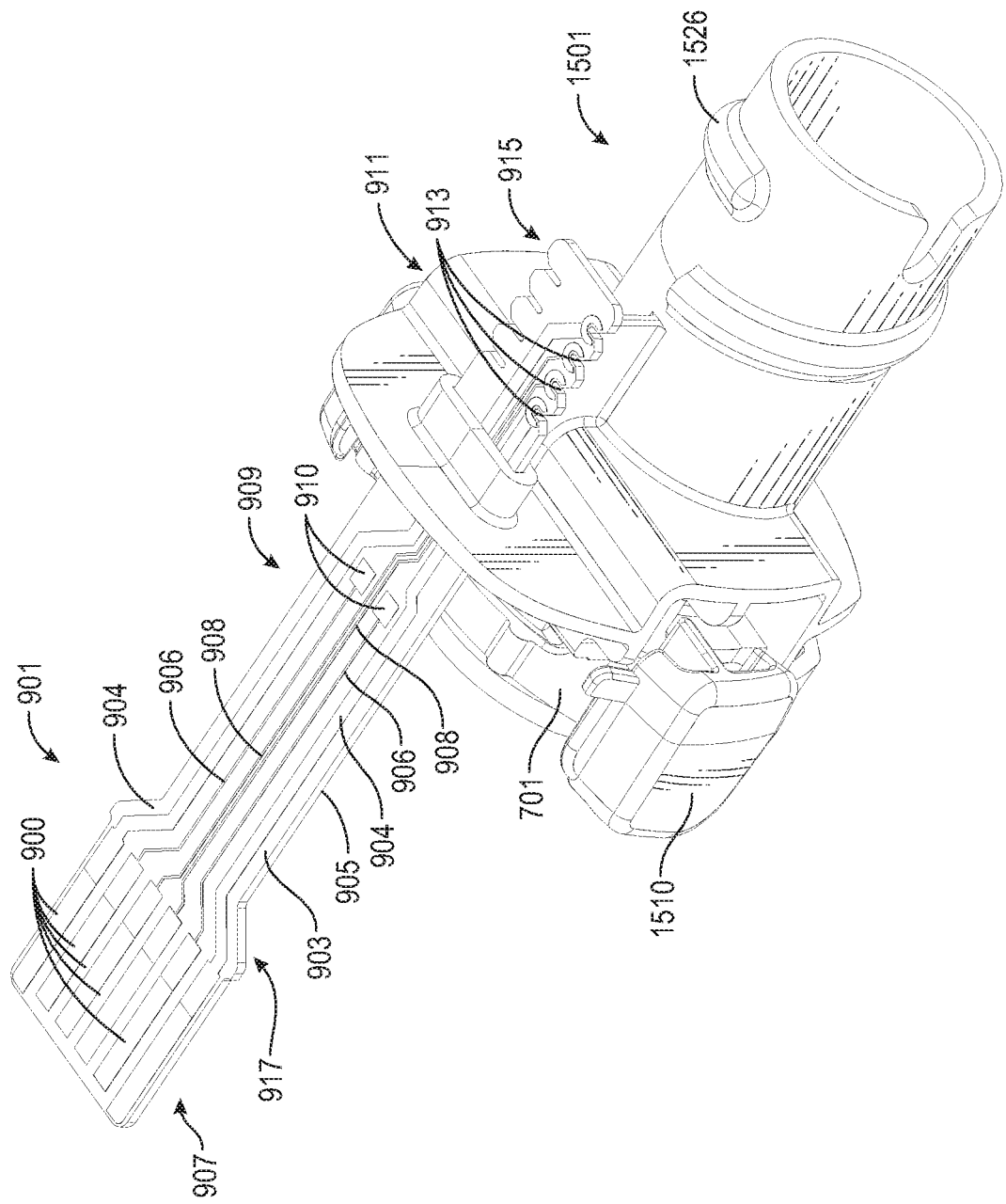
FIG. 62 illustrates a partially disassembled view of a conduit connector.

FIG. 62 illustrates an example embodiment of the edge card 901. The placement of the edge card 901 in the connector relative to the placement of the pneumatic seal can allow for control of the order of the electrical contact and pneumatic seal during connection. In some configurations, the pneumatic connection occurs before the electrical connection. In some configurations, the two connections may occur substantially simultaneously. In some configurations, it may be desired to allow the electrical connection to occur before the pneumatic connection.

With reference to FIG. 62, the edge card 901 is a generally planar component. The edge card 901 in some configurations is a printed circuit board. The edge card 901 can have a top surface 903 and a bottom surface 905. The edge card 901 has an enlarged head region 907, a smaller main body region 909, and the mounting region 911. In some embodiments, the head region 907 meets the mounting region 911 with little or no intervening main body region 909. Each of the regions 907, 909, 911 can be separated from the adjacent regions by a flare (see, e.g., a flare 917) or a step or shoulder. The flares, steps, or shoulders can be used to locate the edge card 901 during assembly of the conduit connector 1500.

The head region 907 can include contact pads 900 for the tracks that will be described. The contact pads 900 have an extended length to accommodate axial (i.e., in the general direction of the tracks and the pads) deviations in positioning while maintaining electrical contact with the cartridge 1300.

The main body region 909 includes a variety of tracks that will be described below as well as a pair of mounting pads 910 for a resistor, which will be described below. In some embodiments, the pair of mounting pads 910 are located on a different portion of the edge card 901, such as the mounting region 911.

The mounting region 911 comprises a plurality of slots 913 and a comb 915. The slots 913 can receive wires to be soldered or otherwise suitably connected to the edge card 901 while the comb 915 assists in repeatable positioning of the wires and in allowing tension to be applied to the wires during the soldering operation. In another embodiment (not shown), the slots 913 alternate on either side of the mounting region 911 to increase their separation from each other.

In the illustrated embodiment, the edge card 901 includes six electrical tracks that extend from the contact pads 900. In some configurations, all of the electrical tracks extend along the top surface 903 of the edge card 901. In some configurations, the entirety of each of the tracks extends along only the top surface 903 of the edge card 901. In some configurations, no portion of the electrical tracks extends along the bottom surface 905 of the edge card 901.

The two outer tracks 904 provide the electrical connection for the heater wire(s) in the inspiratory conduit 120. The two inner tracks 908 provide the electrical connection for the sensor wires. The two intermediate tracks 906 extend to mounting pads 910 for a resistor. The resistor can be an identification resistor as described above. The intermediate tracks 906 therefore provide an electrical connection between the identification resistor and the cartridge 1300 to allow the cartridge 1300 and/or the heater base 102 to identify the inspiratory conduit 120 attached.

In the illustrated configuration, the contact pads 900 associated with the two outer tracks 904 extend further toward the front edge of the PCB than the contact pads 900 associated with the middle four tracks. In addition, the two outer tracks 904 are configured to connect to higher voltage components than the middle four tracks. As such, the outer tracks 904 are wider than the inner tracks 906, 908.

In some embodiments, the difference in length between the contact pads 900 associated with the outer tracks 904 and the contact pads 900 associated with the intermediate and inner tracks 906, 908 allows for control of the order in which the various connections are made and/or broken. For example, the connection of contact pads 900 associate with the high voltage outer tracks 904 can be made before the connection of the contact pads 900 associated with the intermediate tracks 906 that provide the connection to the identification resistor 910. Such a configuration advantageously allows the higher voltage connections to be established before power is supplied from the heater base 102 in configurations where identification (e.g., via the resistor 910) and/or the presence of the sensor wires (e.g., via the inner tracks 908) is required before power is applied to the heater wires that connect to the outer tracks 904. In some configurations, it is possible to terminate power to the high voltage outer tracks 904 upon disconnection of the lower voltage tracks.

Alignment and Engagement Features of Conduit Connector to Cartridge

Figure 66:
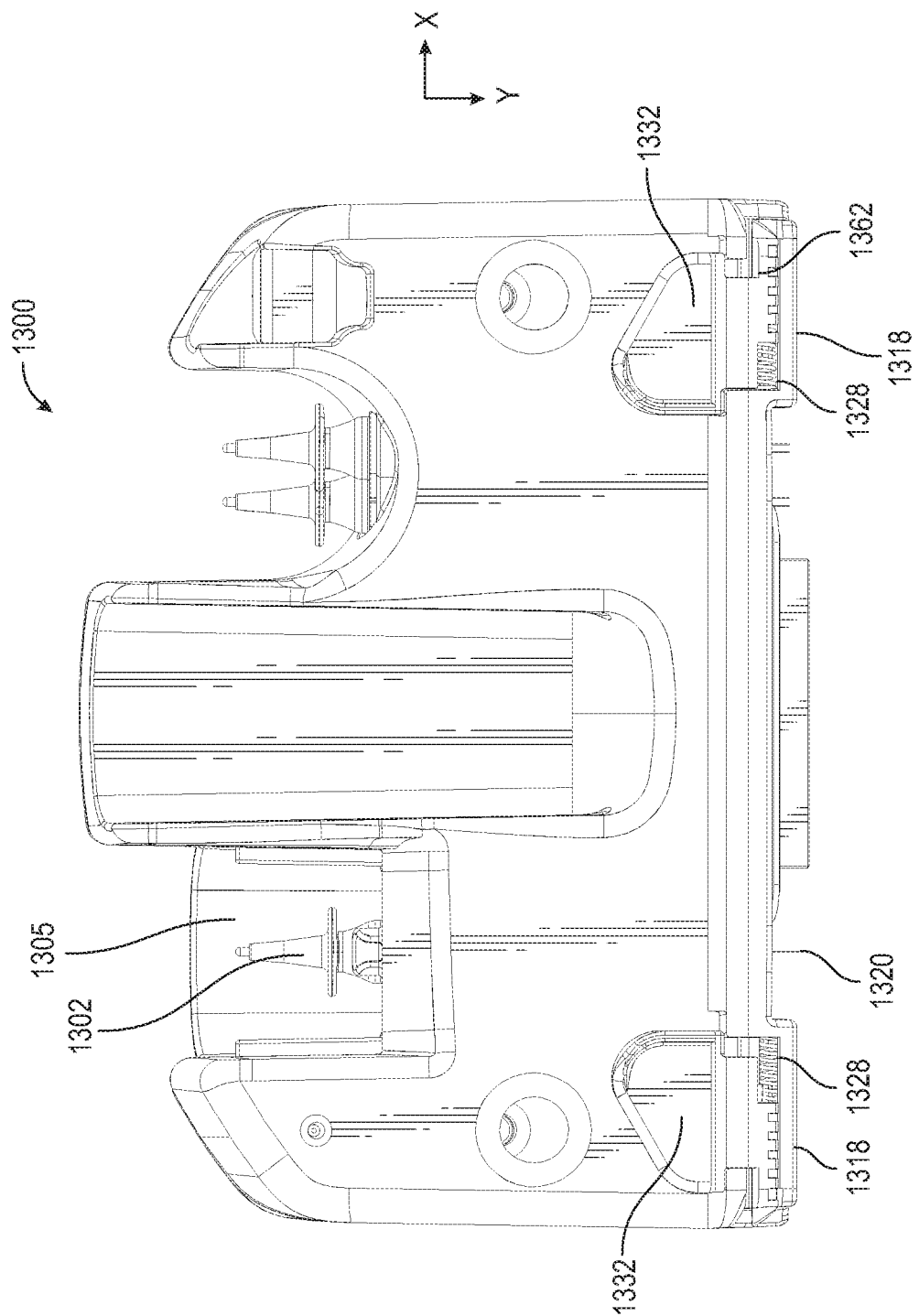
FIG. 66 illustrates a bottom view of the cartridge of FIGS. 60 and 65.

The cartridge 1300 is shown in FIG. 66 including the shroud 1305 which receives and covers the extending portion 1524. This can help to reduce or eliminate the likelihood of any spilled liquid coming into contact with electrical components of the conduit connector 1500 and also serves to strengthen and rigidify the coupling. Further, the shroud 1305 can assist in bringing the conduit connector 1500 into engagement with the outlet port 1412 of the humidification chamber 1104 and/or into engagement with the heater base 102. More particularly, the shroud 1305 provides a visual indication as to where the conduit connector 1500 should be positioned. Further, the shroud 1305 may provide some physical control over the location of the conduit connector 1500. For example, in the embodiment shown, at least the extending portion 1524 of the conduit connector 1500 is received against a portion of the wall of the shroud 1305 opposing the heater plate 108. The shroud 1305 can therefore inhibit or prevent the edge card 901 (or other electrical connection component) from escaping; that is, if the conduit connector 1500 is rotated about the X-axis to too great an extent and the leading end is higher than the trailing end (the end coupled to the inspiratory conduit 120), the edge card 901 cannot slide above the corresponding socket 802 because the shroud 1305 blocks it. This may occur particularly where the heater plate 108 is spring mounted so as to bias the heater plate 108 towards the shroud 1305. Thus, at least the height (i.e., along the Z-axis) of the conduit connector 1500 may be controlled. Having the shroud 1305 provide a curved opposing wall can assist in locating the conduit connector 1500 along the X-axis since the conduit connector 1500 will be urged towards the center of the arc forming the shroud 1305. The physical locating function of the shroud 1305 is yet further improved by having it define a wall that at least partially encloses the conduit connector 1500 so as to control not only an upper limit for the position of the conduit connector 1500 but an actual location thereof.

The shroud 1305 can also protect the first probe 1302. For example, the shroud 1305 can protect the first probe 1302 from damage that may occur if the first probe 1302 were to come into contact with other components or objects during assembly, use, cleaning or the like. As illustrated in FIG. 66, the first probe 1302 can be recessed within the shroud 1305. In other words, the first probe 1302 is hidden from view from the top by the shroud 1305. Moreover, the surrounding surfaces of the cartridge 1300 extend further forward than the first probe 1302, which provides protection against inadvertent contact with the first probe 1302.

Figure 68:
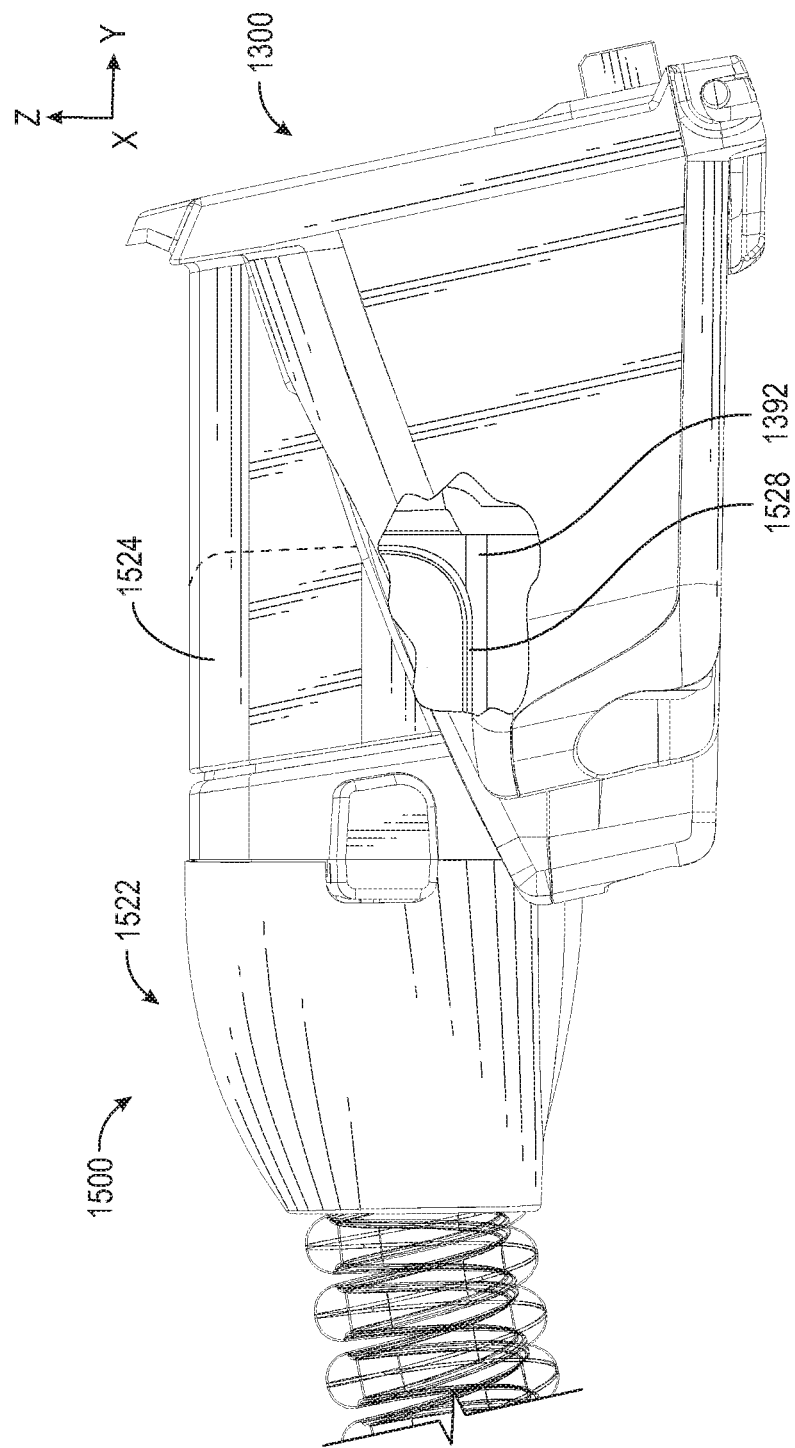
FIG. 68 illustrates the conduit connector of FIGS. 62-63 installed on the cartridge of FIG. 60.

In some embodiments, the shroud 1305 includes rails 1392. The rails 1392 can be positioned within a lower portion of the shroud 1305. The rails 1392 can be configured to engage or support the bottom of the conduit connector 1500 (that is, the bottom of the conduit connector 1500 rests against the top of the rails 1392 when the conduit connector 1500 is engaged with the cartridge 1300) to help inhibit or prevent upward rotation of the conduit. As shown in FIG. 68, a bottom surface 1528 of the extending portion 1524 of the conduit connector 1500 contacts or rests against the top of the rails 1392 when the conduit connector 1500 is coupled to the cartridge 1300. In some embodiments, for example as shown in FIGS. 60 and 68, the rails 1392 ramp upwardly toward the back of the rails 1392 and shroud 1305; in other words, the rails 1392 are tapered toward the front of the rails 1392 and shroud 1305. The ramped or tapered shape of the rails 1392 can help to guide initial alignment of the conduit connector 1500 as it engages with the cartridge. The rails 1392 and contact between the conduit connector 1500 and the rails 1392 can advantageously help reduce or eliminate the likelihood of the conduit connector 1500 rotating about the X-axis.

Figure 63:
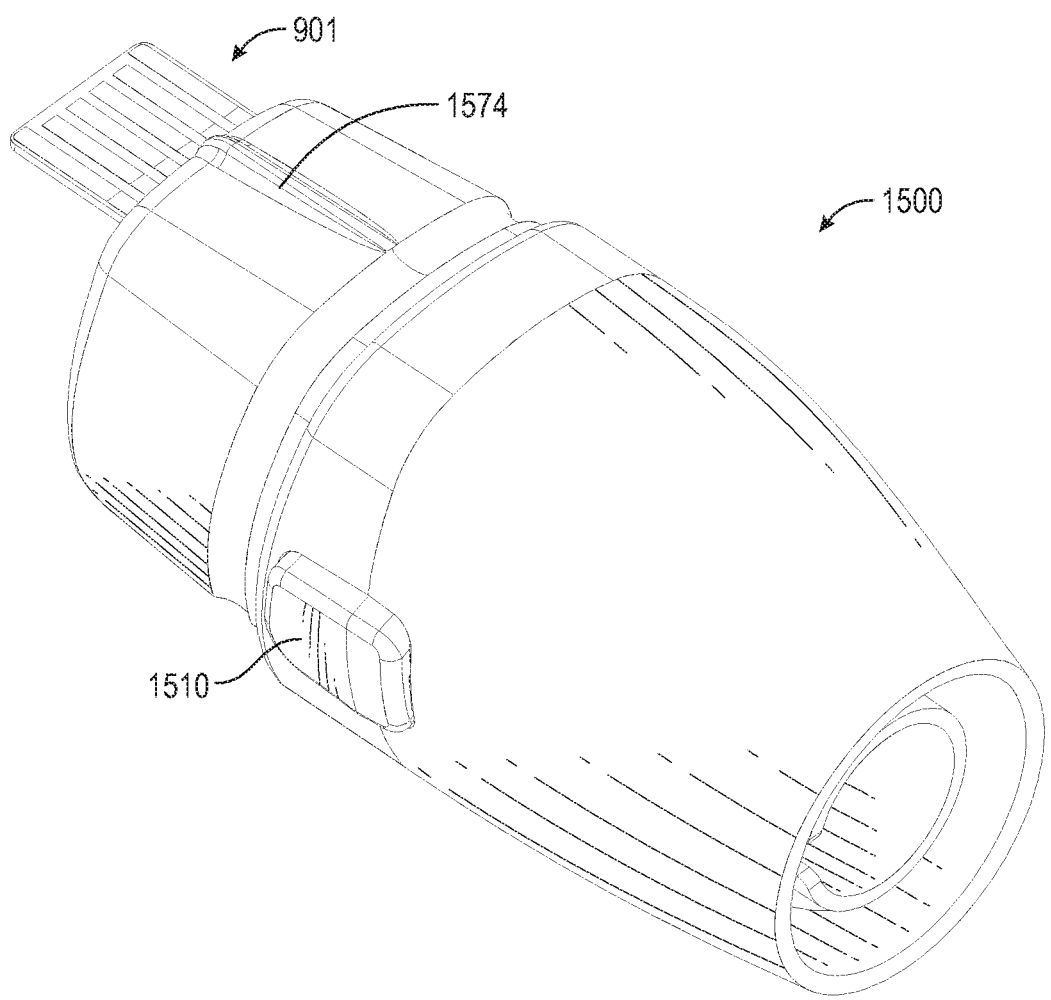
FIG. 63 illustrates an assembled view of the conduit connector of FIG. 62.

In some embodiments, the top of the conduit connector 1500 includes a ridge or rib 1574 as shown in FIG. 63. The rib 1574 is configured to contact the inside of the top of the shroud 1305 such that the shroud 1305 can place additional downward pressure on the conduit connector 1500 to maintain the correct position of the conduit connector 1500.

In some embodiments, the humidification chamber 1104 includes a vertically extending slot 1408 along a rear surface or side of the humidification chamber 1104, for example as shown in FIG. 61. The slot 1408 is formed by a portion of the body 1402 of the humidification chamber 1104 extending inwardly toward the interior of the humidification chamber 1104. The inwardly-extending portion can form part of the intended flow path of gases through the interior of the humidification chamber 1104 from the inlet port 1410 to the outlet port 1412. For example, the inwardly-extending portion can form a baffle inside the humidification chamber 1104 to help direct the flow of gases through the humidification chamber 1104. In some situations, if the user attempts to install the humidification chamber 1104 on the heater base 102 with the humidification chamber 1104 tilted or at an angle, it may be possible for the slot 1408 to become caught on portions of the cartridge 1300, for example, the fins 324, 326 or part of the shroud 1305. To reduce or eliminate the likelihood of this occurring, in some embodiments, the humidification chamber 1104 includes a generally horizontal shelf 1492 (shown in FIG. 61) extending across the slot 1408 at or near the top of the slot 1408. In some configurations, the shelf 1492 can be positioned in other locations along the slot 1408. In some configurations, multiple shelves 1492 can be used. In some configurations, the slot 1408 can be removed or otherwise covered. In use, if the user is attempting to install the humidification chamber 1104 on the heater base 102 at an improper angle, the shelf 1492 can contact portions of the cartridge 1300 to reduce or eliminate the likelihood of the slot 1408 engaging and catching on such portions.

Exchangeable Cartridges

In some embodiments, the cartridge 300 is permanently coupled to or integrally formed with the spine 204 or another portion of the heater base 102. In other embodiments, the cartridge 300 can be configured to be removably coupled to the spine 204 or another portion of the heater base 102. When the cartridge 300 is removably coupled, rather than permanently coupled to the heater base 102, different types or models of the cartridge 300 can be produced for use with different models of the humidification chamber 104, different models of the breathing circuit 123, and/or different therapies. Such a modular configuration advantageously allows a single model of the heater base 102 to be compatible with a variety of consumables and used for a variety of patients and therapy techniques. Having a variety of removable and replaceable cartridges also allows for a range of functionality with a single model of the heater base 102.

Figure 64:
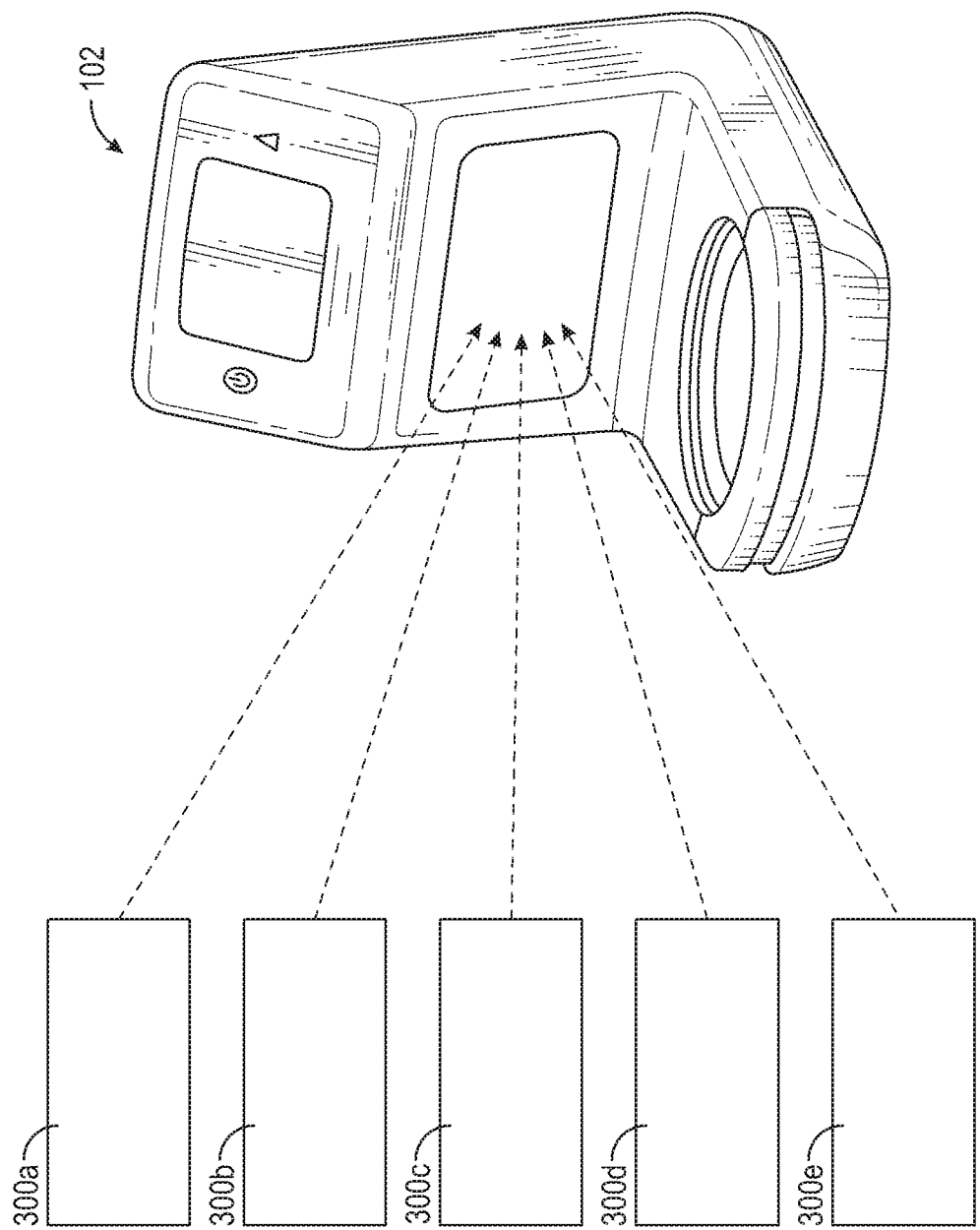
FIG. 64 schematically illustrates exchangeable cartridges for a heater base.

For example, as schematically illustrated in FIG. 64, the sensor cartridge models can include a first cartridge model 300a (e.g., a dual limb cartridge, which interacts with both inspiratory and expiratory conduits), a second cartridge model 300b (e.g., a single limb cartridge, which interacts with only one conduit, for example, only an inspiratory conduit), a third cartridge model 300c (e.g., an infant low flow cartridge, which interacts with a conduit for low flow therapy and/or a smaller volume chamber), a fourth cartridge model 300d (e.g., an adult tall chamber cartridge, which interacts with a standard volume and/or tall chamber), and/or a fifth cartridge model 300e (e.g., a backwards compatible cartridge, which interacts with one or more prior model(s) of chambers, sensors, and/or conduit, or which can be used with prior or other model(s) of chamber(s) and/or conduit(s) without interacting with the chamber and/or conduit). Of course, these are only examples, and various other sensor cartridge models can be developed. The cartridge can interact with chambers, sensors, and/or conduits directly or indirectly, for example, via electrical leads connected to the cartridge. In some embodiments, the cartridge does not interact with or engage any system components other than the heater base. In some such embodiments, the cartridge may only provide electrical feature(s), such as data storage and transfer as described in greater detail below, without providing any sensors or engagement features. By replacing the cartridge, a single heater base can be used with several different consumable packages and the single heater base, therefore, can be used to perform several different therapy regimens. Accordingly, by providing different cartridges, the flexibility of the heater base can be dramatically increased when compared to the prior heater base constructions.

Structural Features

The different cartridge models 300a-300e can include different numbers, types, and/or arrangements of sensors. For example, some of the cartridge models 300a-300e may not include any sensors and can be compatible with humidification chambers that do not include apertures for sensors (e.g., a backwards compatible cartridge). Others of the cartridge models 300a-300e can include pressure, humidity, liquid level, and/or other types of sensors. Some of the cartridge models 300a-300e can also include a receiver for a corresponding electrical connector on another component of the humidification system. For example, the cartridge 300 of FIG. 7A includes the mating electrical connector 350 that corresponds to an inspiratory conduit chamber end connector.

In some embodiments, for example as shown in FIG. 2, the cartridge 300 can include a socket 348. In the illustrated embodiment, the socket 348 is located on an outer surface of one of the sidewalls 320. However, the socket 348 can be located elsewhere on the cartridge 300. The socket 348 can be configured to receive a plug or lead. For example, the socket 348 can receive a lead configured to be coupled to the inspiratory conduit 120 or an inspiratory conduit connector to provide power and/or an electrical connection to a heater wire in the inspiratory conduit 120. In some embodiments, the lead for the heater wire is permanently coupled to the socket 348. In some embodiments, the socket 348 or another socket in the cartridge 300 can provide a connection point for a heater wire in the expiratory conduit 122 and/or one or more sensors. Other cartridge models may not include a socket 348. For example, a socket 348 may not be needed if the expiratory conduit 122 is not used and/or the inspiratory conduit 120 includes a connector that provides a connection for heater wire(s) in the conduit.

Different cartridge models 300a-300e can also include different lead-in and/or engagement features for coupling to different chambers and/or conduits. An operator can select an appropriate cartridge model for the particular patient, therapy, and/or consumables to be used (e.g., the humidification chamber 104 and/or breathing circuit 123) and couple the selected cartridge to the heater base 102.

Electrical Features

In some embodiments, each of the cartridge models 300a-300e includes a memory, such as an EEPROM, or other suitable storage device. When one of the cartridge models 300a-300e is installed on the heater base 102, the memory can be electrically connected to the processor and/or memory of the heater base 102.

The memory of each of the cartridge models 300a-300e can store various information or data. For example, the memory of each of the cartridge models 300a-300e can store data identifying the particular type or model of cartridge and/or the number and types of sensors mounted on the cartridge. In some embodiments, when one of the cartridge models 300a-300e is coupled to the heater base 102, the base processor can read identifying data stored in the cartridge memory and select operational data such as therapy parameters, PID coefficients, thresholds for gases properties such as temperature or flow, algorithms, sensor calibration data, and/or executable code from the memory 112 appropriate for the particular cartridge in use. In some embodiments, the memory of each of the cartridge models 300a-300e stores the appropriate operational data particular to that cartridge model or even particular to each individual cartridge. This data can be uploaded to the base processor and/or memory when the cartridge is coupled to the heater base 102. In some embodiments, sensor calibration data stored in the cartridge memory can allow for increased sensor accuracy. In other words, the system can be calibrated using data on the removable/replaceable cartridge that can be used to correct for variations between sensors from one cartridge to another.

If updates are desired or required, new cartridge models 300a-300e can be produced instead of needing to reprogram the heater base 102. For example, new cartridge models 300a-300e can be produced if new models of the humidification chamber 104, new components of breathing circuit 123, and/or new therapies are developed. Similarly, cartridge models 300a-300e can be made to allow older models of the humidification chamber 104 and/or conduits to be used with a newer model of the heater base 102. Removable and replaceable cartridge models 300a-300e can therefore allow the heater base 102 to have forwards and backwards compatibility with various consumables such as the humidification chamber 104 and conduits. Conversely, a software update of the heater base 102 can include an update of the software of the cartridge model 300a-300e if the software version on the cartridge model 300a-300e is older than the updated version on the heater base 102.

In some embodiments, the base processor 114 can identify the particular cartridge 300, the humidification chamber 104, and/or conduits attached to the heater base 102. The processor 114 can cause a warning message to appear on the display 116 and/or save an error code in the memory 112 if an incompatible component is coupled to the system.

In some embodiments, each of the cartridge models 300a-300e can trigger a result if new software is available for the base. For example, each of the cartridge models 300a-300e can cause the display 116 to prompt the user if new software is available for the base. For example, the memory of the cartridge can be programmed with and store information regarding the latest software version available for the heater base 102 when the cartridge was produced. When the cartridge is coupled to the heater base 102, the processor 114 can compare the software version information stored on the cartridge with the software version being used by the processor 114 or stored in the base memory 112. If the versions do not match, the processor 114 can cause the display 116 to show a message indicating a software update is available. In some embodiments, the cartridge can store the latest software available when the cartridge was produced, and the processor 114 can upload the new software from the cartridge when the cartridge is connected.

In some embodiments, each of the cartridge models 300a-300e can also include a processor. The cartridge processor can be configured to communicate with the base processor when the cartridge is coupled to the base. The cartridge and base processors can coordinate so that different functions can be implemented by either or both of the processors. In some embodiments, configuration-specific functionality configured to be implemented by the cartridge processor can override generic or default functionality implemented by the base processor.

In some embodiments, each of the cartridge models 300a-300e is configured to have a shorter life span or shorter intended duration of use than the heater base 102. For example, each of the cartridge models 300a-300e can include probes and/or other components that should be replaced periodically to ensure sensor reliability and accuracy. Including these probes and/or other components on the removable and replaceable cartridge models 300a-300e advantageously allows these components to be periodically replaced without having to replace the heater base 102. Furthermore, by positioning these components on the removable cartridge models 300a-300e, replacement of the sensors can be dramatically simplified compared to having to individually replacing the sensors. Periodic replacement of the cartridge models 300a-300e can also allow for periodic software updates for the base as discussed above. The cartridge models 300a-300e can be configured to cause the display 116 to prompt the user when the cartridge is approaching and has reached the end of its recommended life span.

As discussed above, each of the cartridge models 300a-300e can be differentiated from each other in form and/or function. For example, the form of the cartridge models 300a-300e can be varied depending upon the other components with which the cartridge is designed to interact. In addition, the function of the cartridge models 300a-300e can be varied depending upon the therapies used with the cartridge and the associated components.

For example, a series of cartridges can be configured to support operation of the humidification system 100 in several configurations, such as by use with individual cartridges that are configured to provide one or more of the following functionalities/system configurations: only an inspiratory conduit and not an expiratory conduit, both an inspiratory conduit and an expiratory conduit, an inspiratory conduit with a heater wire along its length, and/or an inspiratory conduit capable of providing dual zone heating. These variations can correspond to cartridge hardware variations among the various cartridge styles including: different sensor wire connectors, heater wire connectors, and/or directly mounted probes. The variations can also correspond to cartridge software variations among the various cartridge styles including: measurement of ID resistors or other types of identification components, measurement of different types of sensors, control of different types of heater wires, and control of other components such as the heater plate. The sensors can include sensors that measure gas flow rate, pressure, temperature, and/or mixture (e.g., $O_2$ concentration), as well as chamber liquid level, heater plate temperature, and others. Of course, these functional and structural variations are provided for exemplary purposes only and are not intended to be limiting or mutually exclusive. By providing a range of cartridges, different functionalities and structures can be easily provided to the heater base. Accordingly, the variety of cartridges can include configurations that are designed for use in connection with therapies and/or components (e.g., consumable components) that are currently in use within the medical community and new cartridges can be provided that include configurations that will be designed for use in connection with newly discovered therapies and/or newly developed components.

Cartridge to Base Connection

In some embodiments in which the cartridge 300, 1300 is removable from the heater base 102, the cartridge 300, 1300 and the heater base 102 include various features for coupling the cartridge 300, 1300 to the heater base 102.

Figure 67:
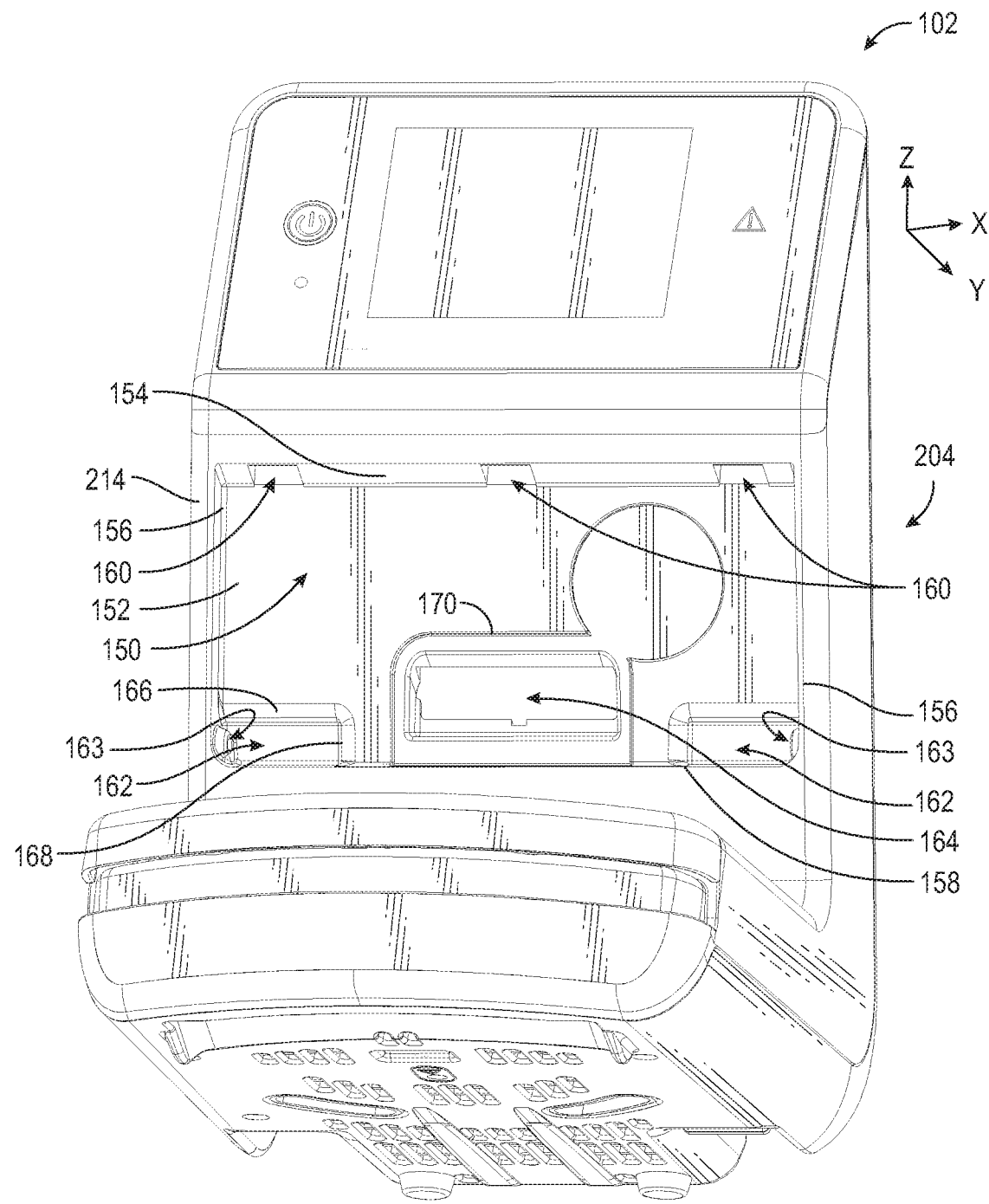
FIG. 67 illustrates an example embodiment of a heater base configured to receive the cartridge of FIGS. 60 and 65-66.

With reference to FIG. 67, the heater base 102 can comprise a recess 150. The recess 150 can be positioned along the spine 204. In the illustrated configuration, the recess 150 is disposed within the front surface 214 of the spine 204.

The recess 150 is sized and configured to receive at least a portion of the cartridge 1300. The recess 150 has a width, a height and a depth that can receive at least a portion of the cartridge 1300. As such, in the illustrated configuration, the recess 150 comprises a back wall 152, an upper wall 154, a pair of side walls 156 and a bottom wall 158. Together, in the illustrated configurations, the upper wall 154, the pair of side walls 156 and the bottom wall 158 generally define a frame that encircles the back wall 152. At least the bottom wall 158 and the side walls 156 extend generally normal to the front surface 214 of the spine 204. In the illustrated configuration, the upper wall 154 of the recess 150 extends at an angle to normal such that the height of the recess 150 decreases with increasing depth in the recess 150. Other configurations are possible.

With reference still to FIG. 67, the heater base 102 can comprise one or more upper recesses 160. In the illustrated configuration, the upper recesses 160 are positioned along the upper wall 154 and extend into the upper wall 154. Preferably, the upper recesses 160 define closed pockets. In other words, the upper recesses 160 are not merely openings into the inside of the housing but are closed pockets. By forming the upper recesses 160 as closed pockets, liquid cannot infiltrate the inside of the heater base 102 through the upper recesses 160.

The illustrated configuration comprises three upper recesses 160. The upper recesses 160 are spaced apart from each other. In the illustrated configuration, one of the three upper recesses 160 is positioned along a central portion of the upper wall 154 such that this central upper recess 160 would be bisected by a vertical plane that bisects the heater base 102. The other two of the three upper recesses 160 are positioned outer, or to each side of, the central upper recess 160. The outer two upper recesses 160 are positioned closer to the side walls 156 than to the central upper recess 160. Other configurations are possible; however, the illustrated configuration provides three upper recesses 160 that are spaced to provide sufficient reinforcement adjacent to the upper recesses 160 while being adequately spaced apart to offer rigidity and secure coupling between the heater base 102 and the cartridge 300, 1300, as will be explained.

With continued reference to FIG. 67, at least one lower recess 162 can be formed that extends into the back wall 152 of the recess 150. In the illustrated configuration, two lower recesses 162 extend into the back wall 152 of the recess 150. The lower recesses 162 can be positioned adjacent to the bottom wall 158. Each of the lower recesses 162 can be disposed adjacent a corresponding one of the side walls 156. In the illustrated configuration, a socket 163 can be positioned in the side wall 156 within the region bounded by the lower recesses 162. The socket 163 can be a depression into the side wall 156 and/or can include an embossment that extends into the region of the lower recesses 162 from the side wall 156.

The lower recesses 162 can have larger widths than heights. The lower recesses 162 can be bounded by an upper recess wall 166 and a central recess wall 168 as well as the side wall 156 and the bottom wall 158. Other configurations are possible. In the illustrated configuration, neither the lower recesses 162 nor the sockets 163 define openings through the housing. By forming the lower recesses 162 and the sockets 163 as closed components, liquid cannot infiltrate the inside of the heater base 102 through the lower recesses 162 or the sockets 163 of the recess 150.

With continued reference to FIG. 67, an electrical terminal 164 can be disposed within the recess 150. In the illustrated configuration, the electrical terminal 164 is generally centrally disposed between the two side walls 156 of the recess 150. The electrical terminal 164 is positioned closer to the bottom wall 158 than the upper wall 154 of the recess 150. Positioning the electrical connector 1364 lower along the rear surface of the cartridge 1300 allows a lower swing angle during connection of the electrical connector 1364 to the electrical terminal 164 of the heater base 102. Thus, the amount of rotation of the cartridge 1300 relative to the base 102 during which the electrical connection is made can be reduced. Moving the electrical connector 1364 vertically upward on the rear surface of the cartridge 1300 would cause the electrical connection with the electrical terminal 164 to occur over a wider range of movement. In the illustrated configuration, a shallow recess 170 completely encircles the electrical terminal 164. In some configurations, the shallow recess 170 may only partially encircle the electrical terminal 164. Other configurations are possible.

Figure 65:
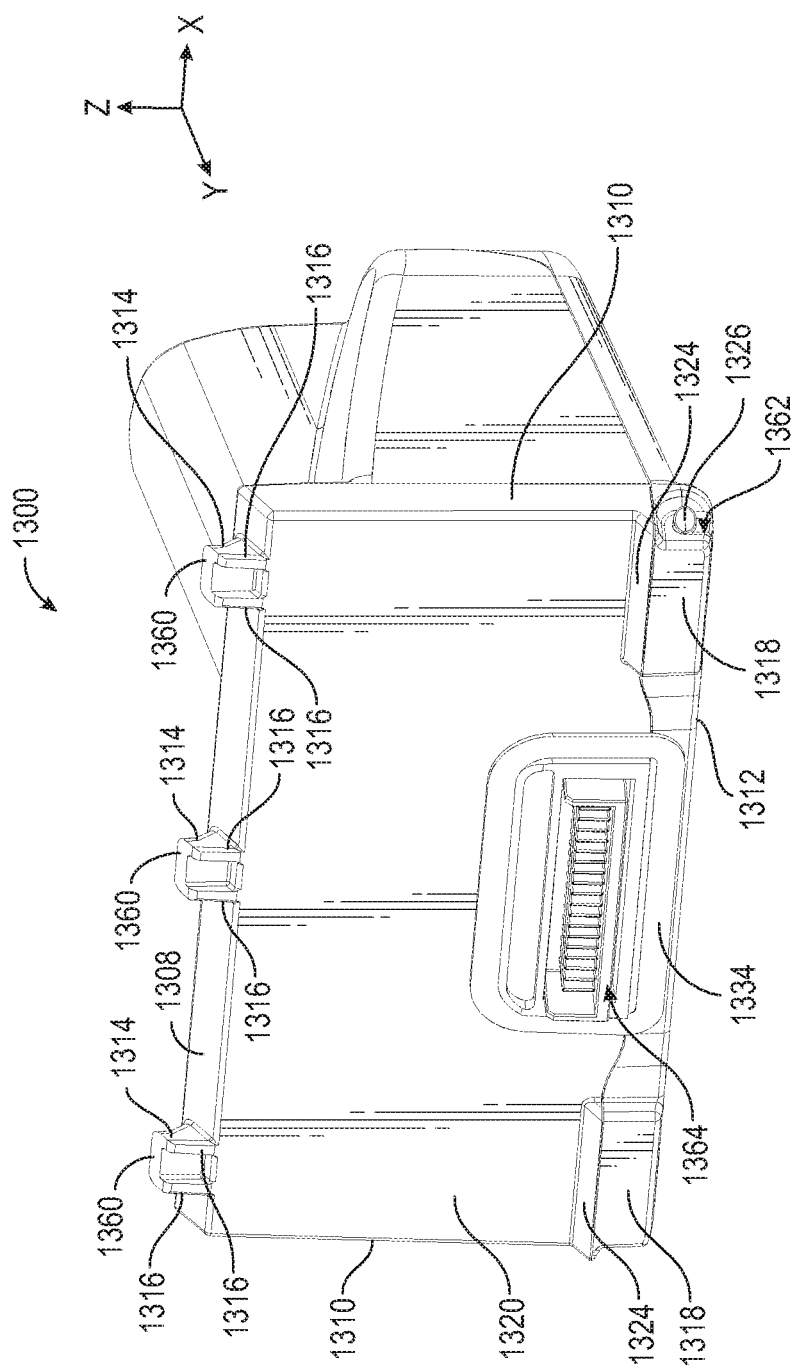
FIG. 65 illustrates a rear perspective view of the cartridge of FIG. 60.

As shown in FIGS. 60 and 65, the cartridge 1300 has a top surface 1308 that generally corresponds to the upper wall 154 of the recess 150. The top surface 1308 generally slopes downward in a rearward direction. The slopes of the top surface 1308 and the upper wall 154 generally correlate to each other, and the sloping surfaces are desired for reasons that will be explained shortly. The cartridge 1300 also includes two side surfaces 1310 and a bottom surface 1312 that correspond to the side walls 156 and the bottom wall 158 of the recess 150.

The top surface 1308 of the cartridge 1300 includes one or more tabs 1360. The tabs 1360 extends upward from the top surface 1308. In the illustrated configuration, the tab 1360 includes a cam surface 1314. The cam surface 1314 is disposed on a forward facing surface. In some configurations, opposite of the cam surface 1314, the tab 1360 includes a pair of ribs 1316 that define a groove. In the illustrated configuration, the uppermost portion of the tab 1360 also slopes rearwardly and downward (i.e., in the same direction as the top surface 1308). Other configurations also are possible.

With continued reference to FIG. 65, the cartridge 1300 includes three tabs 1360. The three tabs 1360 correspond in location to the three upper recesses 160. As with the upper recesses 160, although three tabs spaced across the top surface 1308 are shown in the illustrated embodiment, more or fewer than three tabs are also possible. The tabs 1360 are configured to be received in the corresponding upper recesses 160 in the heater base 102, shown in FIG. 67.

In the illustrated configuration, the cartridge 1300 includes at least one slidable bolt 1362. The bolts 1362 are disposed within protrusions 1318. The protrusions 1318 extend rearward of a rear wall 1320 of the cartridge 1300. In the illustrated configuration, the protrusions 1318 are generally correlated in size and configuration with the lower recesses 162 in the recess 150 of the heater base 102. As such, the protrusions 1318 have a height that is less than the width of the protrusions 1318, as shown in FIG. 65. The protrusions 1318 generally are bounded by the correlating side surface 1310 and the bottom surface 1312. An upper surface 1324 of the protrusions 1318 can be sloping (i.e., not extending normal to the rear wall 1320). As illustrated, the upper surface 1324 can slope such that the protrusions 1318 have a greater height adjacent to the rear wall 1320 and a smaller height further away from the rear wall 1320.

As described above, the cartridge 1300 includes at least one slidable bolt 1362. The bolt 1362 extends laterally outward from the cartridge 1300 beyond the side surface 1310. In some configurations, the bolt 1362 does not extend laterally outward beyond the side surface 1310 but does extend laterally outward beyond the immediately adjacent surfaces.

The bolt 1362 can include a sloped tip 1326. The sloped tip 1326 is sloped or otherwise shaped such that it can ride along a surface of the heater base 102 to cause the bolt 1362 to depress when it contacts a surface. In other words, the sloped tip 1326 can be ramped such that forces applied by an adjacent surface can cause axial movement of the bolt 1362. When the bolt 1362 is properly positioned relative to the socket 163, a biasing member or spring 1328, which will have been compressed during the axial movement of the bolt 1362, will restore the bolt 1362 to a position that is secure within the socket 163. In some configurations, the bolts 1362 can be manually moved without a biasing member or spring 1328.

The bolts 1362 can be joined to, connected to, or integrally formed with, grips, handles or pads 1332. The pads 1332 are shown in FIG. 66. The pads 1332 provide surfaces that can be used to urge the bolts 1362 inwardly (i.e., toward a vertical bisecting plane of the heater base 102) against the force of the springs 1328. By moving the bolts 1362 inwardly, the bolts 1362 can be withdrawn from the sockets 163 to facilitate removal of the cartridge 1300 from the recess 150.

To install the cartridge 1300 on the heater base 102, the user can insert the tabs 1360 upwardly into the upper recesses 160. With the tabs 1360 positioned in the upper recesses 160, the top surface 1308 of the cartridge 1300 moves toward the upper wall 154 of the recess 150. When the top surface 1308 and the upper wall 154 generally abut, the cartridge 1300 can be pivoted downward about the top surface 1308 and the upper wall 154 until the sloped tips 1326 of the bolts 1362 contact the sockets 163. While being pivoted into position, the side walls 156 of the recess 150 interact with the side surfaces 1310 of the cartridge 1300 to guide the cartridge 1300 into a proper position for mating of the electrical connector 1364 of the socket and the electrical terminal 164 of the heater base 102. With the sloped tips 1326 in contact with the sockets 163, further rotation will cause the ramped surfaces of the sloped tips 1326 to compress the springs 1328 until the bolts 1362 align with the openings in the sockets 163, at which time the springs 1328 will move the bolts 1362 outwards into a locked position. In this position, the electrical connector 1364 and the electrical terminal 164 are mated for use.

To remove the cartridge 1300 from the heater base 102, the user slides the bolts 1362 toward one another using the pads 1332 to release the bolts 1362 from the sockets 163. With the bolts 1362 retracted from the sockets 163, the cartridge 1300 can be pivoted outward until the tabs 1360 can be withdrawn downwardly out of the upper recesses 160.

As described above, the cartridge 1300 includes the electrical connector 1364, shown in FIG. 65, configured to establish an electrical connection to the heater base 102. The electrical connector 1364 is configured to be received in or coupled to the corresponding electrical terminal 164 in the heater base 102, shown in FIG. 67. In the illustrated configuration, the electrical terminal 164 is the only opening in the recess 150 that extends into the inner chamber of the heater base 102, which houses electronics and other electrical connections. As described above, the upper recesses 160 and the lower recesses 162 are recesses and are not openings that open into or communicate with the interior of the heater base 102 where electrical components are housed. This advantageously reduces or eliminates the likelihood of liquid being able to enter the interior of the heater base 102. In some embodiments, a ring or gasket 1334 (made of, for example, rubber) is disposed around the electrical connector 1364 to create a seal around the region surrounding the electrical connector 1364 and the electrical terminal 164 to inhibit or prevent liquid ingress into the heater base 102. Advantageously, the gasket 1334 can be provided in the region defined by the shallow recess 170 in the recess 150, which was described above. Furthermore, by positioning the gasket 1334 on the cartridge 1300, the gasket 1334 will be replaced with each change of the cartridge 1300. Other configurations are possible.

As shown in FIG. 60, the cartridge 1300 comprises a receiver 1388, which receives the edge card 901 (see FIG. 62). The edge card 901 inserts into the receiver 1388 by translation along the Y-axis (i.e., the direction of chamber insertion). In some embodiments, the receiver 1388 and/or edge card 901 are configured or positioned to allow for making of both the pneumatic seal with the humidification chamber 1104 and the electrical connection with the cartridge 1300 with a single motion and/or direction of movement. Thus, the cartridge 1300 comprises the receiver 1388 configured to receive a mating component in an Y direction, one or more tabs 1360 extending above the top surface 1308 in a Z direction and one or more bolts 1362 positioned at least partially rearward of the rear wall 1320 of the cartridge 1300 and movable in the X direction. In some configurations, the cartridge 1300 comprises one or more tabs 1360 extending above the top surface 1308 in a Z direction and one or more bolts 1362 positioned at least partially rearward of an adjoining wall and being moveable in the X direction. In some configurations, the cartridge 1300 comprises one tab 1360 that extends in the Z direction above adjoining surfaces at an upper portion of the cartridge 1300 and one bolt 1362 that extends and retracts in the X direction, wherein at least a portion of the one bolt 1362 is rearward of a rearmost portion of the one tab 1360. In some configurations, the cartridge 1300 comprises two bolts 1362 with a recess defined between the two bolts 1362 in at least a portion of the region spanning between the two bolts 1362. In some configurations, the electrical connector 1364 is positioned within the recess. In some such configurations, the recess spans the entire distance between the two bolts 1362 and the electrical connector 1364 is positioned within the recess. In some configurations, at least a portion of the bolt 1362 is positioned rearward in a direction normal to a rear plane defined by the rear wall 1320 of the cartridge 1300 of at least one of a rearmost surface of the tab 1360. In some configurations, at least a portion of the pad 1332 that is attached to the bolt 1362 is positioned forward of the tab 1360. In some configurations, at least a portion of the pad 1332 is forward of a plane that is forward of the forwardmost portion of the uppermost portion of the tab 1360 and parallel to the back wall 152 of the recess 150 of the heater base 102. In some configurations, the electrical connector 1364 extends rearward the most relative to the remainder of the cartridge 1300.

It should be emphasized that many variations and modifications may be made to the embodiments described herein, the elements of which are to be understood as being among other acceptable examples. All such modifications and variations are intended to be included herein within the scope of this disclosure and protected by the following claims. Further, nothing in the foregoing disclosure is intended to imply that any particular component, characteristic or process step is necessary or essential.

What is claimed is:

1. A circuit connector for a humidification system, the circuit connector comprising:
    an inlet at a first end of the circuit connector, the inlet configured to provide a fluid connection from an outlet of a humidification chamber;
    an outlet at a second end of the circuit connector, the outlet configured to provide a fluid connection from the inlet of the circuit connector to a conduit, the conduit configured to direct a gas away from the humidification chamber, wherein the first end and the second end are aligned along a longitudinal axis;

an electrical terminal comprising electrical contacts; and
an orientator contoured to tolerate an incorrect rotational orientation of the circuit connector on initial engagement and correct the incorrect rotational orientation on continued engagement as the circuit connector is pushed towards the outlet of the humidification chamber, and the orientator orientates the circuit connector relative to the outlet of the humidification chamber and orientates the electrical terminal relative to a base unit;
wherein the circuit connector is configured to be releasably and lockably connected to the outlet of the humidification chamber to provide fluid connection between the outlet of the humidification chamber and the inlet of the circuit connector; and
wherein the circuit connector is configured to provide an electrical connection between the electrical terminal and the base unit when the base unit is engaged with the humidification chamber.

2. The circuit connector of claim 1, wherein the circuit connector is configured to be connected to the outlet of the humidification chamber both before and after the humidification chamber is engaged with the base unit.

3. The circuit connector of claim 1, wherein the humidification chamber and the circuit connector are configured to be removed from the base unit with the circuit connector remaining in fluid connection with the outlet of the humidification chamber.

4. The circuit connector of claim 1, wherein the electrical terminal is substantially parallel to the inlet of the circuit connector to enable both electrical and fluid connections to be effected in a single motion.

5. The circuit connector of claim 1, wherein the orientator comprises a recess configured to slidably engage a projection on the outlet of the humidification chamber in a single orientation.

6. The circuit connector of claim 5, wherein the recess is keyhole shaped.

7. The circuit connector of claim 1, wherein the orientator comprises a projection configured to slidably engage a recess in the outlet of the humidification chamber in a single orientation.

8. A humidification system comprising:
a humidification chamber, wherein an outlet of the humidification chamber comprises a first portion that extends substantially vertically from the humidification chamber and a second portion that extends substantially horizontally from the first portion, the second portion being downstream of the first portion; and
the circuit connector of claim 1, wherein the inlet of the circuit connector is configured to provide a fluid connection to the second portion of the circuit connector, and
the orientator is configured to accommodate the first portion.

9. The circuit connector of claim 1, wherein the orientator comprises a wider opening end than a termination end.

10. The circuit connector of claim 1, wherein the electrical contacts are configured to contact with one or more tracks of a printed circuit board associated with the base unit.

11. The circuit connector of claim 1, wherein the electrical terminal comprises a printed circuit board comprising one or more tracks configured to make contact with one or more electrical contact elements associated with the base unit.

12. The circuit connector of claim 1, further comprising an edge card configured to be received in an edge card receptacle on the base unit.

13. The circuit connector of claim 12, wherein the humidification chamber is configured to be inserted on the base unit along a first axis, wherein the edge card is configured to be received in the edge card receptacle along a second axis, and wherein the second axis is parallel to the first axis.

14. The circuit connector of claim 1, wherein the electrical terminal is electrically connected to one or more heater wires and/or one or more sensor wires.

15. The circuit connector of claim 1, further comprising a recess or projection configured to be engaged by a latch on a wall of the outlet of the humidification chamber, wherein the latch provides a releasable and lockable connection of the circuit connector to the outlet of the humidification chamber.

16. The circuit connector of claim 1, further comprising a latch configured to engage a recess or projection of a wall of the outlet of the humidification chamber, wherein the latch provides a releasable and lockable connection of the circuit connector to the outlet of the humidification chamber.

17. The circuit connector of claim 16, wherein the latch comprises one or more buttons protruding outward from the latch, and an upper portion of the latch configured to deflect away from an axial center of the circuit connector when inward force is applied to the one or more buttons.

18. The circuit connector of claim 17, wherein the upper portion of the latch is configured to engage the recess or projection of the wall of the outlet of the humidification chamber.

19. The circuit connector of claim 18, wherein the upper portion of the latch is configured to disengage the recess or projection of the wall of the outlet of the humidification chamber when an inward force is applied to the one or more buttons.

20. The circuit connector of claim 18, wherein the upper portion of the latch is configured to disengage the recess or projection of the wall of the outlet of the humidification chamber when the upper portion deflects away from the axial center of the circuit connector.

21. The circuit connector of claim 16, further comprising an activator configured to disengage the latch from the recess or protrusion to allow removal of the circuit connector from the outlet of the humidification chamber.

22. The circuit connector of claim 21, wherein the activator comprises at least one manually depressible button or switch.

23. The circuit connector of claim 1, wherein at least a portion of the circuit connector is receivable inside the outlet of the humidification chamber.

24. The circuit connector of claim 1, further comprising an inner plug portion comprising an outer groove near a distal end of the inner plug portion, and a seal disposed in the outer groove.

25. The circuit connector of claim 24, wherein the seal is generally T-shaped.

26. The circuit connector of claim 24, wherein the seal is generally V-shaped.

27. The circuit connector of claim 1, wherein when the electrical terminal is received in a receptacle on the base unit, a processor of the base unit is configured to determine a model of the circuit connector, and the processor is configured to select operational, control, and/or therapy parameters based on the model that has been determined.

28. The circuit connector of claim 27, wherein the processor of the base unit determines the model based on a measurement of a resistor having a first resistance value in a first range of values, wherein the circuit connector comprises at least one heater wire having a second resistance value in a second range of values, and wherein the first range of values does not overlap with the second range of values.

29. A humidification system comprising the circuit connector of claim 1.

30. The circuit connector of claim 1, wherein the humidification chamber is configured to be inserted on the base unit along a first axis, wherein the circuit connector is configured to be coupled to the outlet of the humidification chamber along a second axis, and wherein the first axis is parallel to the second axis.

31. The circuit connector of claim 1, further comprising a seal configured to seal against an inside of the outlet of the humidification chamber when the circuit connector is connected to the outlet.

32. The circuit connector of claim 1, further comprising an identification component configured to be measured by the base unit when the electrical terminal is received in a receptacle on the base unit, wherein a processor of the base unit is configured to determine a model of the circuit connector based on a measurement of the identification component, and the processor is configured to select operational, control, and/or therapy parameters based on the model that has been determined.

33. The circuit connector of claim 1, wherein the base unit measures a resistance when the electrical terminal is received in a receptacle on the base unit, wherein a processor of the base unit is configured to determine a model of the circuit connector based on a measurement of the resistance, and the processor is configured to select operational, control, and/or therapy parameters based on the model that has been determined.

34. A circuit connector configured for use with a humidification system comprising a base unit and a humidification chamber engageable with the base unit, the circuit connector comprising:
 an outer body comprising:
  an inlet at a first end of the circuit connector, the inlet configured to provide a fluid connection from an outlet of the humidification chamber;
  an outlet at a second end of the circuit connector, the outlet configured to provide a fluid connection from the inlet of the circuit connector to a conduit, the conduit configured to direct a gas away from the humidification chamber, wherein the first end and the second end are aligned along a longitudinal axis;
  an angled cutout to rotationally orientate the circuit connector relative to the outlet of the humidification chamber, the angled cutout extending axially into the outer body from the first end of the circuit connector; and
 an electrical terminal comprising electrical contacts, the electrical terminal configured to provide an electric connection to the base unit;
 wherein the electrical terminal and the angled cutout are at least partially aligned along an axis perpendicular to a longitudinal axis of the outer body.

35. The circuit connector of claim 34, wherein the electrical terminal is substantially parallel to the inlet of the circuit connector to enable both electrical and fluid connections to be effected in a single motion.

36. The circuit connector of claim 34, wherein the angled cutout forms a part of a recess.

37. The circuit connector of claim 36, wherein the recess is configured to receive a projection disposed on the outlet of the humidification chamber to orientate the circuit connector relative to the outlet of the humidification chamber.

38. The circuit connector of claim 34, wherein the outer body comprises a projection configured to engage a recess in the outlet of the humidification chamber to orientate the circuit connector relative to the humidification chamber.

39. The circuit connector of claim 34, wherein the electrical contacts are configured to make contact with one or more tracks of a printed circuit board associated with the base unit.

40. The circuit connector of claim 34, wherein the electrical terminal comprises a printed circuit board comprising one or more tracks configured to make contact with one or more electrical contact elements associated with the base unit.

41. The circuit connector of claim 34, wherein the electrical terminal comprises an edge card configured to be received in an edge card receptacle associated with the base unit.

42. The circuit connector of claim 34, wherein the electrical terminal comprises an edge card receptacle configured to receive an edge card associated with the base unit.

43. A humidification system comprising:
 the base unit;
 the humidification chamber engageable with the base unit; and
 the circuit connector of claim 34.

44. The circuit connector of claim 34, wherein the angled cutout is wider at the first end of the circuit connector.

\* \* \* \* \*